United States Patent
Cui

(10) Patent No.: US 11,965,177 B2
(45) Date of Patent: Apr. 23, 2024

(54) METHOD OF MANUFACTURING DUAL SPECIFIC T-CELLS FOR USE IN CANCER IMMUNOTHERAPY

(71) Applicant: VERSITI BLOOD RESEARCH INSTITUTE FOUNDATION, INC., Milwaukee, WI (US)

(72) Inventor: Weiguo Cui, Brookfield, WI (US)

(73) Assignee: VERSITI BLOOD RESEARCH FOUNDATION, INC., Milwaukee, WI (US)

(*) Notice: Subject to any disclaimer, the term of this patent is extended or adjusted under 35 U.S.C. 154(b) by 632 days.

(21) Appl. No.: 17/160,952

(22) Filed: Jan. 28, 2021

(65) Prior Publication Data
US 2021/0189338 A1 Jun. 24, 2021

Related U.S. Application Data

(63) Continuation of application No. 15/777,399, filed as application No. PCT/US2016/062831 on Nov. 18, 2016, now Pat. No. 10,941,381.

(60) Provisional application No. 62/257,429, filed on Nov. 19, 2015.

(51) Int. Cl.
| | |
|---|---|
| C12N 5/0783 | (2010.01) |
| A61K 9/00 | (2006.01) |
| A61K 35/17 | (2015.01) |
| A61K 39/00 | (2006.01) |
| A61P 35/00 | (2006.01) |

(52) U.S. Cl.
CPC .......... *C12N 5/0638* (2013.01); *A61K 9/0019* (2013.01); *A61K 35/17* (2013.01); *A61K 39/0011* (2013.01); *A61K 39/00119* (2018.08); *A61K 39/001192* (2018.08); *A61P 35/00* (2018.01); *C12N 5/0636* (2013.01); *A61K 2039/5156* (2013.01); *A61K 2039/5158* (2013.01); *A61K 2039/522* (2013.01); *A61K 2039/523* (2013.01); *A61K 2039/55594* (2013.01); *A61K 2039/572* (2013.01); *A61K 2039/585* (2013.01); *C12N 2501/2302* (2013.01); *C12N 2501/2307* (2013.01); *C12N 2501/2315* (2013.01); *C12N 2501/50* (2013.01); *C12N 2510/00* (2013.01); *Y02A 50/30* (2018.01)

(58) Field of Classification Search
None
See application file for complete search history.

(56) References Cited

U.S. PATENT DOCUMENTS

| | | |
|---|---|---|
| 5,830,755 A | 11/1998 | Nishimura et al. |
| 7,723,111 B2 | 5/2010 | Hwu et al. |
| 8,211,422 B2 | 7/2012 | Eshhar et al. |

FOREIGN PATENT DOCUMENTS

| | | |
|---|---|---|
| WO | 2015121454 A1 | 8/2015 |
| WO | 2015142675 A2 | 9/2015 |

OTHER PUBLICATIONS

Baitsch et al., Exhaustion of Tumor-Specific CD8+ T Cells in Metastases from Melanoma Patients, Journal of Clinical Investigation, 2011, 121(6):2350-2360.
Cui et al., Redirected Adoptive Cell Transfer (ReACT)—A Multi-Pronged Strategy to Treat Solid Tumors, Journal of Immunology, 2016, 196(1 Supplement): 143-121 [Filed with PCT International Search Report].
Feuerer et al., Therapy of Human Tumors in NOD/SCID Mice with Patient-Derived Reactivated Memory T Cells from Bone Marrow, Nature Medicine, 2001, 7(4):452-458.
Gladow et al., Dual T Cell Receptor T Cells with Two Defined Specificities Mediate Tumor Suppression via Both Receptors, European Journal of Immunology, 2004, 34(7):1882-1891.
Kershaw et al., Dual-Specific T Cells Combine Proliferation and Antitumor Activity, Nature Biotechnology, 2002, 20(12):1221-1227.
Rosenberg et al., Adoptive Cell Transfer: A Clinical Path to Effective Cancer Immunotherapy, Nature Reviews Cancer, 2008, 8(4):299-308.
Rossig et al., Epstein-Barr Virus-Specific Human T Lymphocytes Expressing Antitumor Chimeric T-cell Receptors: Potential for Improved Immunotherapy, Blood, 2002, 99(6):2009-2016.
Wang et al., Manufacture of Tumor- and Virus-Specific T Lymphocytes for Adoptive Cell Therapies, Cancer Gene Therapy, 2015, 22(2):85-94.
Xin et al., Pathogen Boosted Adoptive Cell Transfer Immunotherapy to Treat Solid Tumors, Proceedings of the National Academy of Sciences, 2017, 114(4):740-745.
PCT International Search Report and Written Opinion, PCT/US2016/062831, dated Feb. 16, 2017, 15 pages.
European Patent Office, Extended Search Report, Application No. 16879674.6, dated Jul. 3, 2019, 7 pages.
European Patent Office, Communication, Application No. 16879674.6, dated Sep. 21, 2020, 5 pages.
An et al., Construction of a New Anti-CD19 Chimeric Antigen Receptor and the Anti-Leukemia Function Study of the Transduced T Cells, Oncotarget, 2016, 7(9):10638-10649.
Barnas et al., T Cells and Stromal Fibroblasts in Human Tumor Microenvironments Represent Potential Therapeutic Targets, Cancer Microenvironment, 2010, 3(1):29-47.

(Continued)

*Primary Examiner* — Robert M Kelly
(74) *Attorney, Agent, or Firm* — Quarles & Brady LLP

(57) ABSTRACT

The present invention relates to autologous dual-specific lymphocytes, methods of making and uses for the treatment of tumors. In particular, the invention relates to methods producing autologous dual-specific lymphocytes comprising an endogenous receptor for at least one tumor associated antigen and an exogenous receptor for a strong antigen

19 Claims, 36 Drawing Sheets
Specification includes a Sequence Listing.

(56) References Cited

OTHER PUBLICATIONS

Bellone et al., Ways to Enhance Lymphocyte Trafficking into Tumors and Fitness of Tumor Infiltrating Lymphocytes, Frontiers in Oncology, 2013, vol. 3, Article 231, pp. 1-15.
Chandra et al., Myeloid-Derived Suppressor Cells have a Central Role in Attenuated Listeria Monocytogenes-Based Immunotherapy Against Metastatic Breast Cancer in Young and Old Mice, British Journal of Cancer, 2013, 108 (11):2281-2290.
Curiel, Tregs and Rethinking Cancer Immunotherapy, Journal of Clinical Investigation, 2007, 117(5):1167-1174.
Frassanito et al., Identification of Meth A Sarcoma-Derived Class I Major Histocompatibility Complex-Associated Peptides Recognized by a Specific CD8+ Cytotoxic T Lymphocyte, Cancer Research, 1995, 55(1):124-128.
Gabrilovich et al., Coordinated Regulation of Myeloid Cells by Tumours, Nature Reviews Immunology, 2012, 12(4):253-268.
Gajewski et al., Molecular Profiling to Identify Relevant Immune Resistance Mechanisms in the Tumor Microenvironment, Current Opinion in Immunology, 2011, 23(2):286-292.
Gajewski et al., Innate and Adaptive Immune Cells in the Tumor Microenvironment, Nature Immunology, 2013, 14(10):1014-1022.
Ganss et al., Tumor Microenvironment Can Restrict the Effectiveness of Activated Antitumor Lymphocytes, Cancer Research, 1998, 58(20):4673-4681.
Ganss et al., Combination of T-cell Therapy and Trigger of Inflammation Induces Remodeling of the Vasculature and Tumor Eradication, Cancer Research, 2002, 62(5):1462-1470.
Garbe et al., Systematic Review of Medical Treatment in Melanoma: Current Status and Future Prospects, The Oncologist, 2011, 16(1):5-24.
Garbi et al., CpG Motifs as Proinflammatory Factors Render Autochthonous Tumors Permissive for Infiltration and Destruction, Journal of Immunology, 2004, 172(10):5861-5869.
Grupp et al., Chimeric Antigen Receptor-Modified T Cells for Acute Lymphoid Leukemia, New England Journal of Medicine, 2013, 368(16):1509-1518.
Haverkamp et al., In vivo Suppressive Function of Myeloid-Derived Suppressor Cells is Limited to the Inflammatory Site, European Journal of Immunology, 2011, 41(3):749-759.
Heemskerk et al., Reprogramming of Virus-Specific T Cells into Leukemia-Reactive T Cells Using T Cell Receptor Gene Transfer, Journal of Experimental Medicine, 2004, 199(7):885-894.
Jin et al., Safe Engineering of CAR T Cells for Adoptive Cell Therapy of Cancer Using Long-Germ Episomal Gene Transfer, EMBO Molecular Medicine, 2016, 8(7):702-711.
Kalia et al., Prolonged Interleukin-2Rα Expression on Virus-Specific CD8+ T Cells Favors Terminal-Effector Differentiation In Vivo, Immunity, 2010, 32(1):91-103.
Ko et al., Sunitinib Mediates Reversal of Myeloid-Derived Suppressor Cell Accumulation in Renal Cell Carcinoma Patients, Clinical Cancer Research, 2009, 15(6):2148-2157.
Le et al., Regulatory T-cell Modulation Using Cyclophosphamide in Vaccine Approaches: A Current Perspective, Cancer Research, 2012, 72(14):3439-3444.
Liang et al., β-Catenin Mediates Tumor-Induced Immunosuppression by Inhibiting Cross-Priming of CD8+ T Cells, Journal of Leukocyte Biology, 2014, 95(1):179-190.
Louis et al., Antitumor Activity and Long-Term Fate of Chimeric Antigen Receptor-Positive T Cells in Patients with Neuroblastoma, Blood, 2011, 118(23):6050-6056.
Lu et al., Tumor-Infiltrating Myeloid Cells Induce Tumor Cell Resistance to Cytotoxic T Cells in Mice, Journal of Clinical Investigation, 2011, 121(10):4015-4029.
Maude et al., Chimeric Antigen Receptor T Cells for Sustained Remissions in Leukemia, New England Journal of Medicine, 2014, 371(16):1507-1517.
Maus et al., Antibody-Modified T Cells: CARs Take the Front Seat for Hematologic Malignancies, Blood, 2014, 123(17):2625-2635.
McGray et al., Immunotherapy-Induced CD8+ T Cells Instigate Immune Suppression in the Tumor, Molecular Therapy, 2014, 22(1):206-218.
Mikucki et al., Non-Redundant Requirement for CXCR3 Signalling During Tumoricidal T-cell Trafficking Across Tumour Vascular Checkpoints, Nature Communications, 2015, 6(1):1-14.
Mock et al., Automated Manufacturing of Chimeric Antigen Receptor T Cells for Adoptive Immunotherapy Using CliniMACS Prodigy, Cytotherapy, 2016, 18(8):1002-1011.
Murphy et al., Antitumor Activity of Dual-Specific T Cells and Influenza Virus, Cancer Gene Therapy, 2007, 14(5):499-508.
Overwijk et al., Tumor Regression and Autoimmunity After Reversal of a Functionally Tolerant State of Self-Reactive CD8+ T Cells, The Journal of Experimental Medicine, 2003, 198(4):569-580.
Petrausch et al., Cancer Immunotherapy: The Role Regulatory T Cells Play and What Can Be Done to Overcome Their Inhibitory Effects, Current Molecular Medicine, 2009, 9(6):673-682.
Pipkin et al., Interleukin-2 and Inflammation Induce Distinct Transcriptional Programs that Promote the Differentiation of Effector Cytolytic T Cells, Immunity, 2010, 32(1):79-90.
Restifo et al., Adoptive Immunotherapy for Cancer: Harnessing the T Cell Response, Nature Reviews Immunology, 2012, 12(4):269-281.
Rosenberg et al., Adoptive Cell Transfer as Personalized Immunotherapy for Human Cancer, Science, 2015, 348(6230):62-68.
Sadelain et al., The Basic Principles of Chimeric Antigen Receptor Design, Cancer Discovery, 2013, 3(4):388-398.
Stark et al., Intracellular Bacterial Vectors that Induce CD8+ T Cells with Similar Cytolytic Abilities but Disparate Memory Phenotypes Provide Contrasting Tumor Protection, Cancer Research, 2009, 69(10):4327-4334.
Turtle et al., Engineered T Cells for Anti-Cancer Therapy, Current Opinion in Immunology, 2012, 24(5):633-639.
Urbanska et al., Targeted Cancer Immunotherapy via Combination of Designer Bispecific Antibody and Novel Gene-Engineered T Cells, Journal of Translational Medicine, 2014, 12:347, 12 pages.
Wood et al., Attenuated Listeria Monocytogenes: A Powerful and Versatile Vector for the Future of Tumor Immunotherapy, Frontiers in Cellular and Infection Microbiology, 2014, vol. 4, Article 51, pp. 1-22.
European Patent Office, Communication, Application No. 16879674.6, dated Jul. 26, 2021, 3 pages.
Joyce et al., T Cell Exclusion, Immune Privilege, and the Tumor Microenvironment, Science, 2015, 348(6230):74-80.
Monjezi et al., Enhanced CAR T-cell Engineering Using Non-Viral Sleeping Beauty Transposition from Minicircle Vectors, Leukemia, 2017, 31:186-194.
Oldham et al., Lentiviral Vectors in Cancer Immunotherapy, Immunotherapy, 2015, 7(3):271-284.
Redelman-Sidi et al., The Mechanism of Action of BCG Therapy for Bladder Cancer—A Current Perspective, Nature Reviews Urology, 2014, 11:153-162.
Ren et al., Modification of Cytokine-Induced Killer Cells with Chimeric Antigen Receptors (CARs) Enhances Antitumor Immunity to Epidermal Growth Factor Receptor (EGFR)-Positive Malignancies, Cancer Immunology, Immunotherapy, 2015, 64:1517-1529.
Vigneron et al., Database of T Cell-Defined Human Tumor Antigens: The 2013 Update, Cancer Immunity, 2013, vol. 13, p. 15, 6 pages.

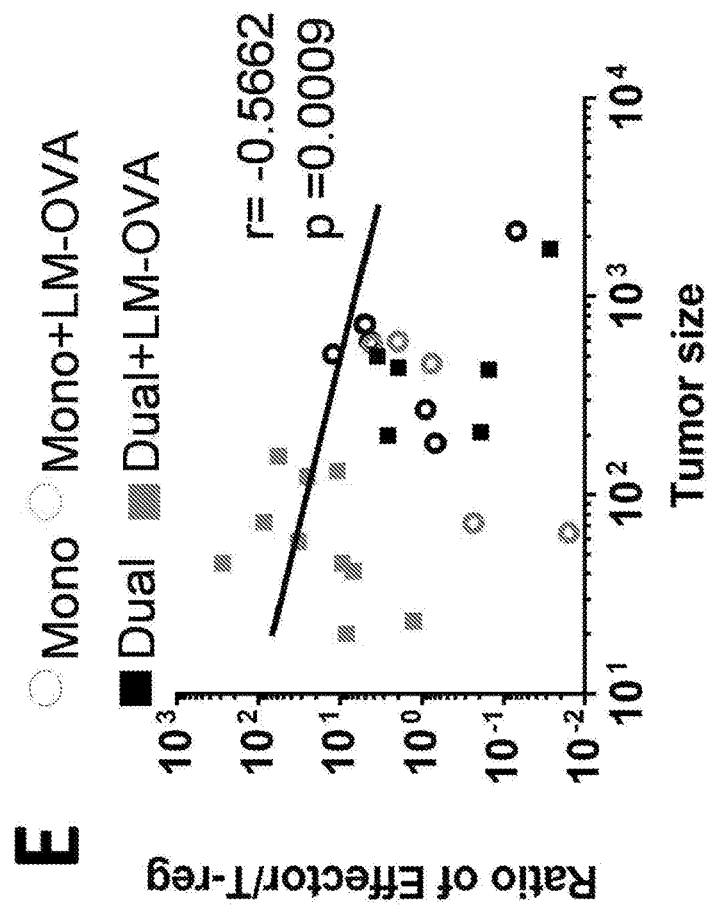
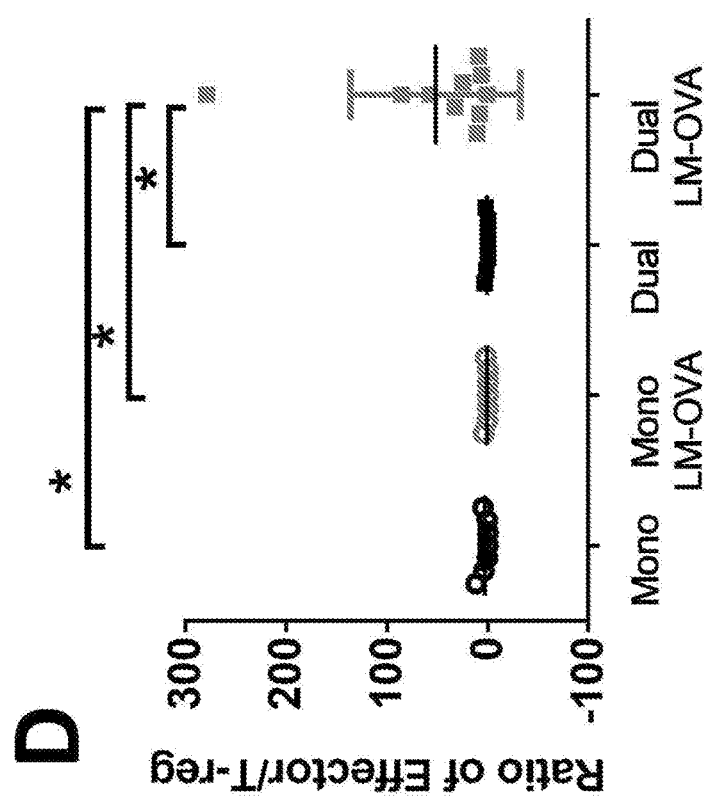
FIGS. 5A-5J continued

METHOD OF MANUFACTURING DUAL SPECIFIC T-CELLS FOR USE IN CANCER IMMUNOTHERAPY

CROSS-REFERENCE TO RELATED APPLICATIONS

This application is a Continuation of U.S. patent application Ser. No. 15/777,399 filed May 18, 2018, which is a 371 Application of PCT/US2016/062831 filed Nov. 18, 2016, which claims the benefit of U.S. Provisional Patent Application Ser. No. 62/257,429 filed on Nov. 19, 2015 entitled "Method of Manufacturing Dual Specific T-Cells for Use in Cancer Immunotherapy," the contents of which are incorporated by reference in their entirety.

STATEMENT REGARDING FEDERALLY SPONSORED RESEARCH

N/A

SEQUENCE LISTING

A Sequence Listing accompanies this application and is submitted as an ASCII text file of the sequence listing named "160180_00152_ST25_txt" which is 742 bytes in size and was created on Jan. 28, 2021. The sequence listing is electronically submitted via EFS-Web with the application and is incorporated herein by reference in its entirety.

BACKGROUND OF THE INVENTION

The field of the invention is cancer immunotherapy. More particularly, the invention relates to adoptive cell transfer for the treatment of cancer.

Various types of cancer are often refractory to standard treatments such as chemotherapy or radiation. Adoptive cell transfer (ACT) of genetically engineered T cells has become a promising cancer immunotherapy for hematologic malignancies (1-4). This approach includes engineering and expanding the tumor-infiltrating lymphocytes, which can recognize tumor associated antigens (TAAs), followed by infusing them into patients to induce a tumor specific immune response. Despite the recent success in treating hematopoietic malignancies (Maus, et al.), the efficacy of such an approach is curtailed when treating solid tumors (2,5,6). The primary hurdles that must be overcome for ACT to be effective against solid tumors include: inadequate responses of adoptively transferred T cells, especially in dealing with heterogeneous cancerous cells that bear a wide range of tumor associated antigens (2,6); reduced migration of adoptively transferred T cells into the tumor (7); and, the immunosuppressive microenvironment within tumors that often induces a rapid loss of T cell effector function (8).

Using infectious pathogens that stimulate a patient's immune system and break immunosuppression in the tumor microenvironment is a century old strategy that is now being rejuvenated to enhance cancer immunotherapy (9). *Bacillus* Calmette-Guérin (BCG), a live attenuated strain of *Mycobacterium bovis*, has been widely used in treating bladder cancer and melanoma for decades (10,11). Although effective, BCG only induces transient and non-specific antitumor immune responses. One reason for this is that the inflammatory reaction induced by BCG does not target and immune response to the tumor. To generate a tumor-specific T cell response, recombinant *Listeria monocytogenes* (LM) expressing engineered TAAs have recently been developed and shown promising results in treating multiple cancers, including breast and pancreas (9). Owing to the heterogeneity of tumor cells, it remains challenging for recombinant LM-based immunotherapies targeting a single TAA to provide durable and complete regression of cancer because cancer cells that don't express the targeted TAA are able to evade immunosurveillance (2,6,7,9). Thus, there is a critical need for new strategies that generate robust T cell responses with broad coverage of tumor antigens to improve pathogen-based cancer vaccines.

SUMMARY OF THE INVENTION

The present invention overcomes the aforementioned drawbacks of ACT by providing an innovative approach that not only overcomes immunosuppression, but also recruits robust polyclonal anti-tumor T cell responses to the very site of the tumor. First, autologous lymphocytes (e.g. CD8+ T cells) taken from a patient which are specific to a plurality of tumor associated antigens are genetically engineered to recognize both the tumor associated antigen and a strong antigen that is non-tumor in vitro. These engineered autologous lymphocytes are then transfused back into the patient in combination with injecting or instilling the strong antigen directly into or to the tumor. The dual-specific CD8 T cells expand robustly and migrate to the tumor bed where they recognize the infectious agent. At the same time, the second TCR of these effector CD8 T cells recognize tumor antigens and execute effector function, causing site-specific tumor regression and long-lasting antitumor immunity. Complete and lasting tumor regression was seen in some treated animals. Overall, the present invention harnesses the power of multiple arms of the immune system with promising translational value, which can be used to target many types of solid tumors.

In one aspect, a purified population of dual-specific lymphocytes which have specificity for two or more antigens is provided, wherein a population of lymphocytes is isolated from a patient and wherein each lymphocyte expresses an endogenous receptor for a tumor associated antigen (TAA) and is genetically engineered to express an additional exogenous receptor for a strong antigen. This population of dual-specific lymphocytes can target and be activated by a plurality of TAAs and the strong antigen. In a preferred aspect, the lymphocytes are CD8+ T cells.

In some aspects, the present invention is a composition comprising or consisting essentially of a purified population of dual-specific lymphocytes and a pharmaceutically acceptable carrier.

In a further aspect, a method of producing an autologous population of dual-specific lymphocytes specific for a plurality of tumor associated antigens and at least one strong antigen is provided. The method comprising the steps of:
  (a) isolating lymphocytes from a patient;
  (b) purifying the tumor-specific lymphocytes from the isolated lymphocytes; and
  (c) genetically engineering the purified lymphocytes to express a second receptor specific to at least one strong antigen,
  wherein the resulting population comprises dual-specific lymphocytes.

In some aspects, the method further comprises (d) culturally expanding the dual-specific lymphocytes to increase the number of dual-specific lymphocytes.

In another aspect, a method of treating a patient with a tumor is provided. The method comprises (a) administering to the patient an effective amount of autologous dual-specific lymphocytes, and (b) injecting the patient with a strong antigen. In a preferred aspect, the strong antigen is injected intratumorally.

In yet another aspect, a pharmaceutical composition is provided. The pharmaceutical composition comprises or consists essentially of a population of autologous dual-specific lymphocytes reactive with a plurality of tumor associated antigens specific to a tumor and genetically engineered to express a receptor reactive with a strong antigen; and a pharmaceutically acceptable carrier.

In another aspect, a kit for treating a tumor in a patient is provided, the kit comprising dual-specific lymphocytes autologous to the patient that recognize a plurality of tumor associated antigens and a strong antigen, and a sufficient amount of strong antigen able to be injected into the patient.

In another aspect, a kit for producing a population of dual-specific lymphocytes autologous to a patient is provided. The kit includes (a) a vector encoding a receptor specific to a strong antigen able to be expressed in a cell.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A. The experimental scheme of ReACT (Reenergized Adoptive Cell Transfer). Pmel-1 CD8 T cells are transduced in vitro to express a second TCR (OT-I) to generate T cells that could recognize both a TAA gp100 and a surrogate bacterial antigen $OVA_{257-264}$. These dual-specific CD8 T cells were expanded in vitro and transferred to tumor-bearing mice followed by i.t. LM-OVA infection.

FIG. 1B. Dot plots show the intracellular IFNγ staining in Pmel-1$^+$ or OT-I$^+$ Pmel-1$^+$ CD8 T cells after 6 hours of stimulation with gp100 or OVA peptide, respectively.

FIG. 1C. The B16-F10 tumor-bearing mice received the following combinations of treatments: mono-specific CD8 T cell transfer, mono-specific CD8 T cell transfer accompanied by i.t. injection of LM-OVA, dual-specific CD8 T cell transfer or dual-specific CD8 T cell transfer accompanied by i.t. injection of LM-OVA. In each group, $5 \times 10^5$ CD8 T cells were transferred into each mouse. The individual tumor growth curves following each treatment as stated in (C) were analyzed by Kruskal-Wallis with Dunn's multiple comparison tests. The number on top right represents the responder/total mice ratio.

FIG. 1D. The overall tumor growth is shown as mean volume±s.e.m.

FIG. 2A. C57BL/6 mice with established B16-F10 tumors were treated with ACT of either OT-I cells ($5 \times 10^5$/mouse) alone or mixed Pmel-1 ($2.5 \times 10^5$/mouse) and OT-I cells ($2.5 \times 10^5$/mouse), followed by LM-OVA i.t. injection. The individual tumor growth curves are shown.

FIG. 2B. C57BL/6 mice were injected i.t. with either LM-OVA or LM-GP33 one week after subcutaneous inoculation with B16-OVA tumor cells. Tumor growth in each group was monitored over time, and individual tumor growth curves are shown. In all experiments, mice that eradicated tumors were defined as responders (shown in solid lines), while the remaining mice were defined as non-responders (shown in dashed lines). The number on top right represents the responder/total mice ratio. Data shown are pooled from two to three independent experiments.

FIG. 3A. The schematic for generating polyclonal dual-specific CD8 T cells for ReACT therapy against solid tumors.

FIG. 3B. Four groups of tumor bearing mice received different treatment regimens including: polyclonal mono-specific CD8 T cell transfer ($5 \times 10^5$/mouse) with or without LM-OVA infection and polyclonal dual-specific CD8 T cell transfer ($5 \times 10^5$/mouse) with or without LM-OVA infection. The responders (shown in solid lines) and non-responders (shown in dashed lines) in each were defined as described in FIG. 1. The data were analyzed by Kruskal-Wallis with Dunn's multiple comparison tests.

FIG. 3C. The individual growth curves of breast cancer E0771 tumors after receiving four different treatments as stated in (B) are shown.

FIG. 3D. Mice that eradicated their primary B16-F10 tumors were re-inoculated with $1 \times 10^4$ B16-F10 cells (shown in left) and previously unencountered breast cancer cells (E0771, shown in right). As a reference, B16-F10 tumor growth in naive mice is also shown. The number of tumor free mice are shown, and were analyzed by Log-rank test. Data were pooled from two independent experiments.

FIG. 4A. The representative plots are gated on CD8 T cells and the numbers indicate the percentage of transferred (GFP+) cells.

FIG. 4B. The percentage and absolute number (normalized to tumor volume) of transferred CD8 T cells were calculated and shown in the plots.

FIG. 4C. Correlation plot shows the relationship between tumor sizes and frequency of CD8 T cells within the tumor in each treatment group. Each data point represents an individual mouse.

FIG. 4D. The expression of CD44, KLRG-1, CXCR3 and granzyme B were compared in dual-specific and mono-specific CD8 T cells by flow cytometry. Naïve CD8 T cells (CD44$^-$) served as control.

FIG. 4E. The representative plots show the production of IFNγ and TNFα after stimulation with gp100 peptide in vitro for 6 hours.

FIG. 4F. The percentage of IFNγ producing CD8$^+$ T cells was calculated and shown in the plot. Data shown are pooled from three independent experiments.

FIG. 5A. The frequency of CD25$^+$ Foxp3$^+$ Tregs inside tumors from mice that received each treatment described in FIG. 1 is shown in the dot plots.

FIG. 5B. The percentage and absolute number of Tregs normalized with tumor volume were calculated and plotted in the graphs. FIG. 5C. Correlation plot shows the relationship between tumor sizes and frequency of Tregs inside the tumor.

FIG. 5D. The Teff/Treg ratios were calculated and plotted in the graphs.

FIG. 5E. The Teff/Treg ratios calculated and plotted in the graphs.

FIG. 5F. The frequency of CD11b$^+$Gr-1$^+$ MDSCs in tumors is shown in the dot plots.

FIG. 5G. The percentage and absolute number of CD11b$^+$ Gr-1$^+$ MDSCs normalized with tumor volume were enumerated and plotted in the graph.

FIG. 5H. The expression of iNOS was compared in CD11b$^+$Gr-1$^+$ cells from uninfected and infected tumor-bearing mice and shown in histograms.

FIG. 5I. The CD11b$^+$ cells were sorted from B16-F10 tumors treated with either i.t. injection of LM-OVA or PBS. These cells were co-cultured with activated CD8 T cells and the proliferation of T cells was assessed by $^3$H-thymidine incorporation and shown in bar graphs.

FIG. 5J. The expression of inhibitory receptors (LAG3, CTLA4, Tim3 and PD-1) was compared between dual-specific and mono-specific CD8 T cells inside tumor and plotted in histograms. Data were pooled from three independent experiments.

FIG. 6A. Surface marker expression of BMDCs was analyzed by flow cytometry and shown in the dot plot and histogram.

FIG. 6B. BMDCs pulsed with tumor cell lysates were used to generate polyclonal dual-specific CD8 T cells. Histograms show the expression of surface phenotypic markers on the activated dual-specific CD8 T cells.

FIG. 7A. Dot plots show the frequency of adoptively transferred CD8 T cells from each group in the peripheral blood ten days after treatments.

FIG. 7B. The frequency and number of adoptively transferred CD8 T cells in the tumors were enumerated and shown in scatter plots.

FIG. 7C. The association plot shows the relationship between tumor sizes and the frequency of CD8 T cells in the tumors.

FIG. 7D. The expression of PD-1, KLRG-1 and granzyme B were compared between dual-specific, mono-specific and naive CD8 T cells and shown in histograms. Results are representative of 2 independent experiments, with n>3/group. * denotes P<0.05,  denotes P<0.01, and * denotes P<0.001.

FIG. 8A. The intratumoral Tregs were identified as CD25+ Foxp3+ and shown in representative FACS pots gated on CD4+ cells.

FIG. 8B. The frequency and number of Tregs were enumerated and shown in scatter plots.

FIG. 8C. The correlation plot shows the relationship between the frequency of intratumoral Tregs and tumor sizes.

FIG. 8D. The CD8 Teff/Treg ratios and their association with tumor sizes were calculated and shown in graphs. Results are representative of 2 independent experiments, with n>3/group. ** denotes P<0.01.

FIG. 8E. The CD8 Teff/Treg ratios and their association with tumor sizes were calculated and shown in graphs. Results are representative of 2 independent experiments, with n>3/group. ** denotes P<0.01.

FIG. 9A. The frequency and absolute number of CD11b$_+$ myeloid cells from tumors were enumerated and shown in scatter plots.

FIG. 9B. The iNOS expression in CD1 lb$_+$ cells isolated from tumor bearing mice with or without i.t. LM-OVA infection was analyzed by flow cytometry at day 3 p.i. and shown in the histogram. Results are representative of 3 independent experiments, with n>3/group. * denotes P<0.05,  denotes P<0.01, and * denotes P<0.001.

DETAILED DESCRIPTION OF THE INVENTION

Figures 1A, 1B, 1C, 1D:
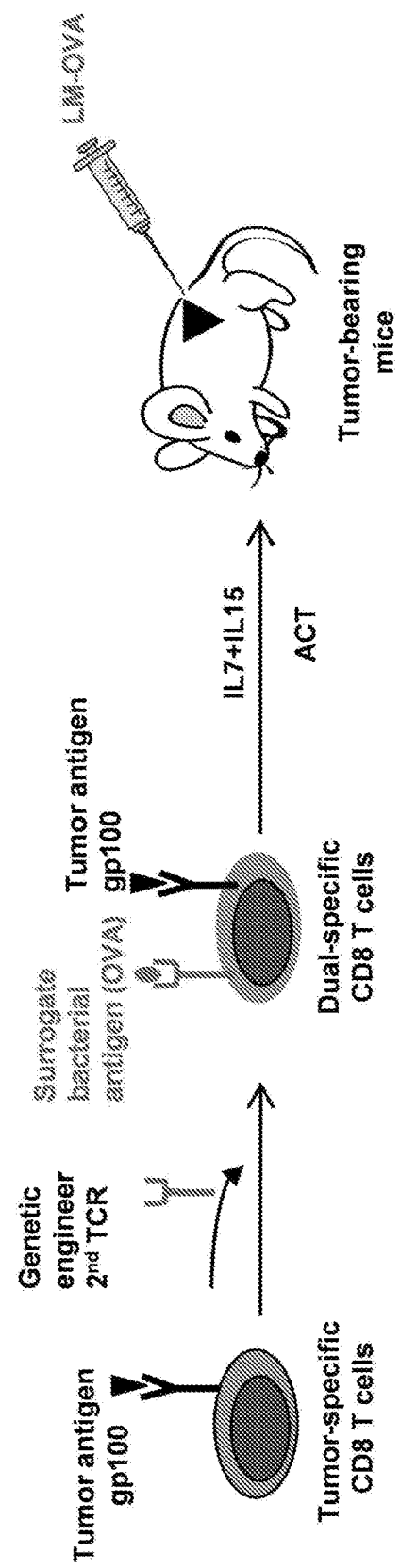
FIGS. 1A-1D indicate ReACT shows significantly enhanced antitumor efficacy.
Figures 1A, 1B, 1C, 1D:
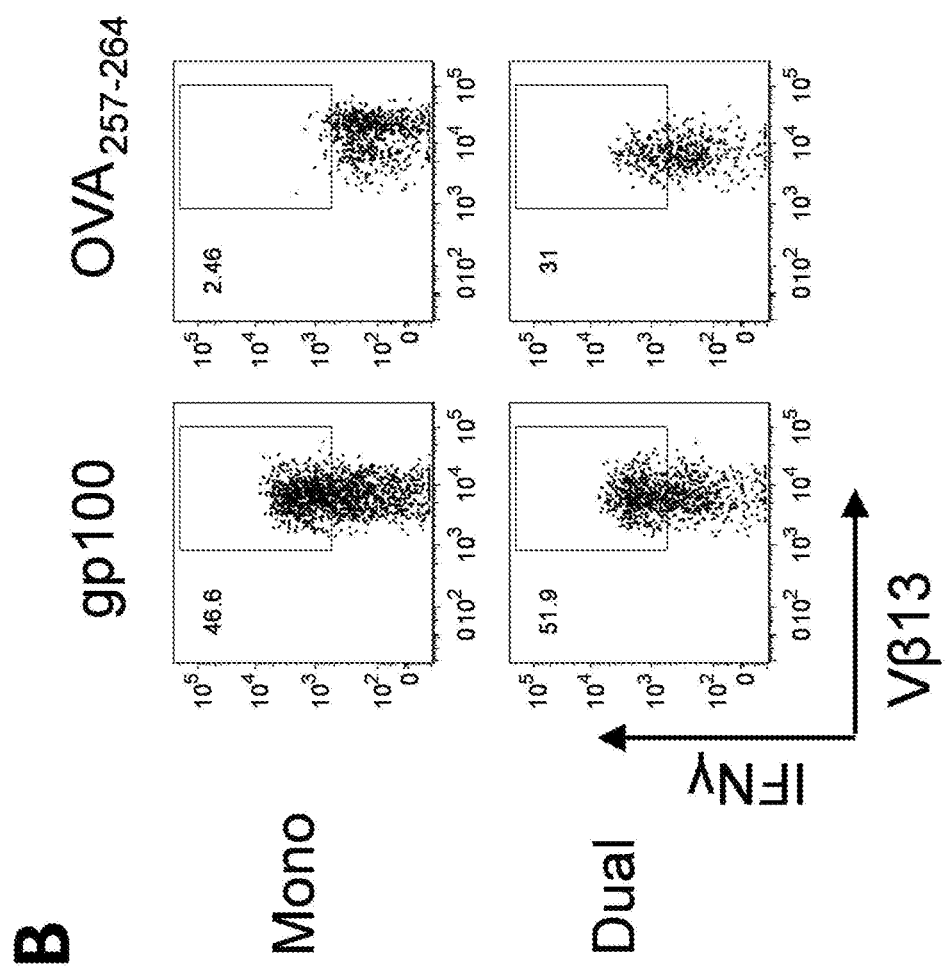
Figures 1A, 1B, 1C, 1D:
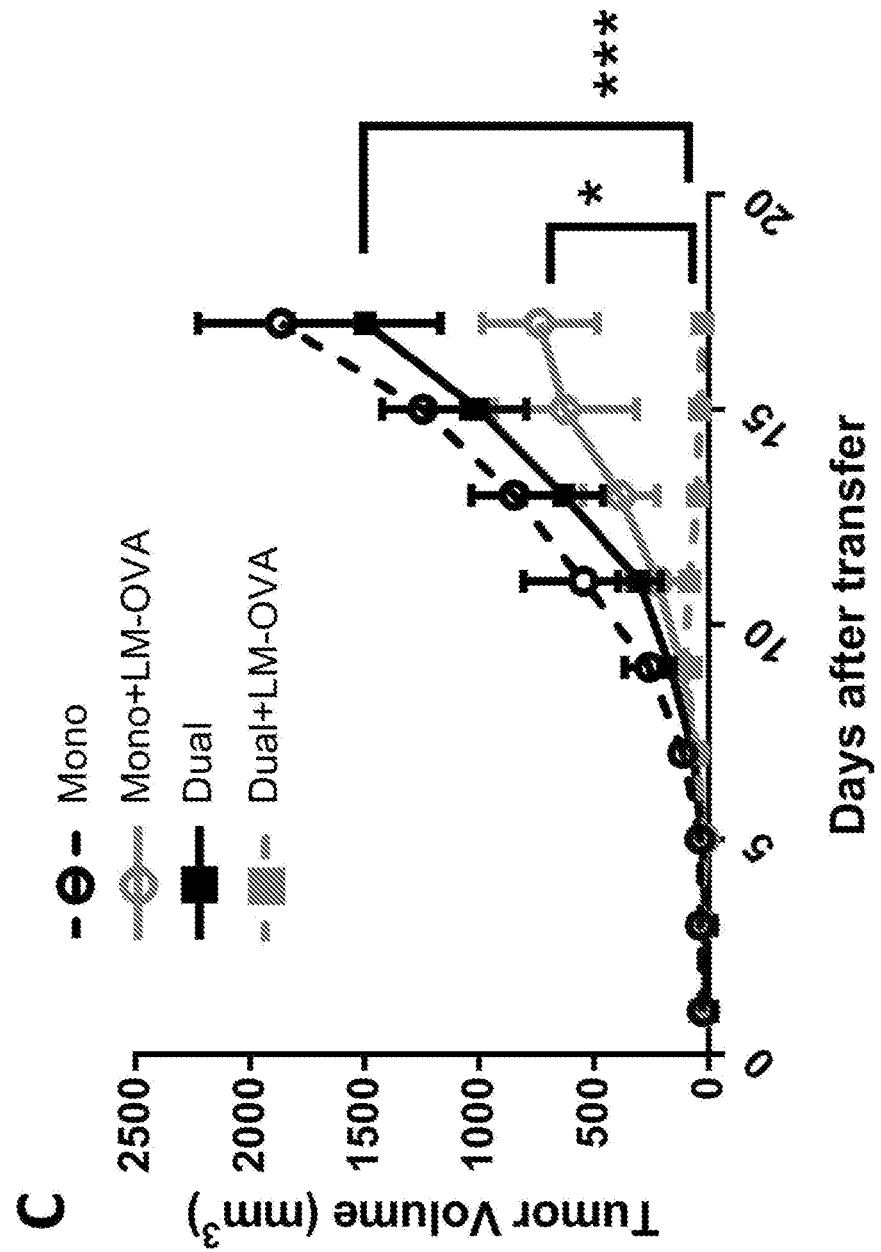
Figures 1A, 1B, 1C, 1D:
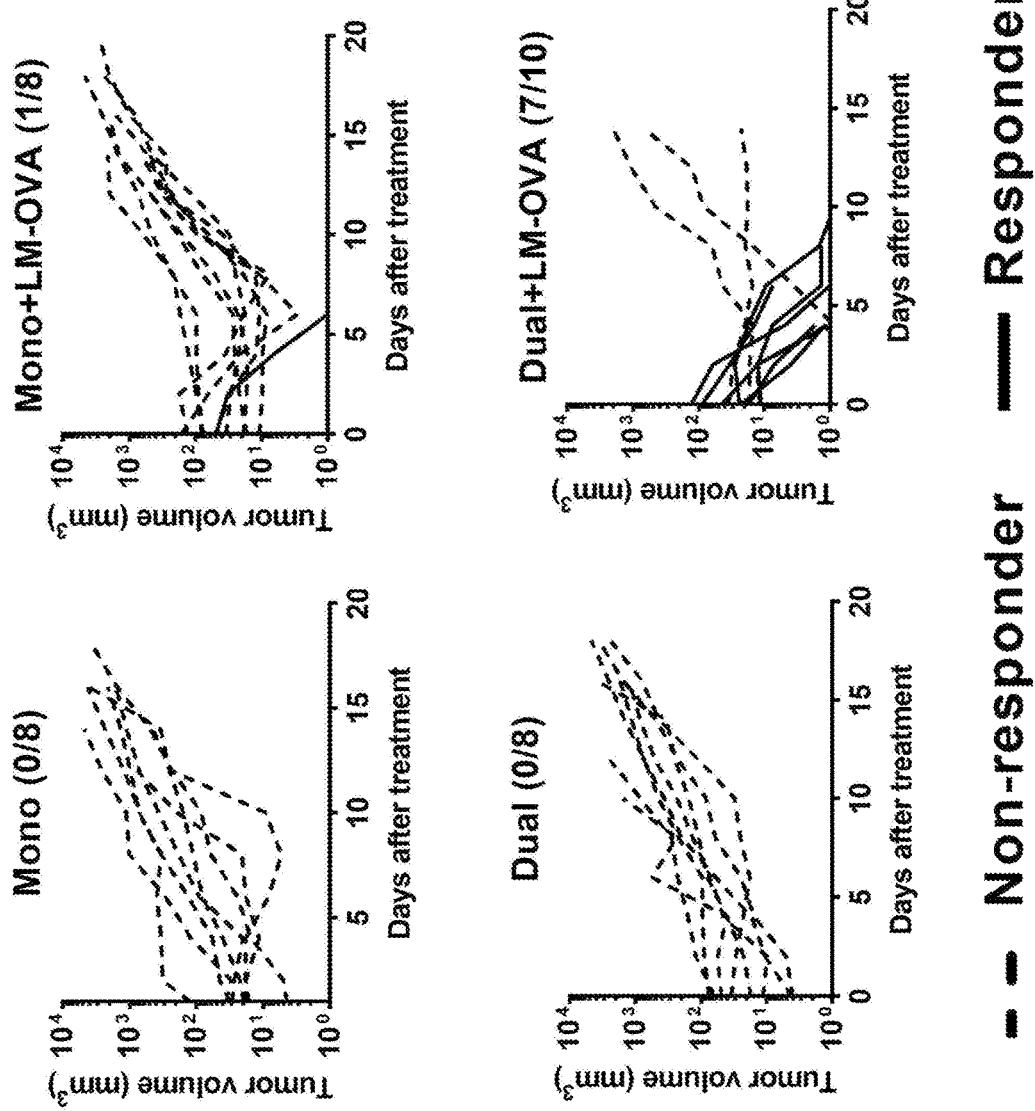

The present invention has been described in terms of one or more preferred embodiments, and it should be appreciated that many equivalents, alternatives, variations, and modifications, aside from those expressly stated, are possible and within the scope of the invention.

The present disclosure provides a purified population of autologous dual-specific lymphocytes, methods of making and methods of using these dual-specific lymphocytes to treat tumors in a patient.

Adoptive cell transfer (ACT) based immunotherapy in fighting cancer has recently attracted great interest. This approach includes engineering and expanding the tumor-infiltrating lymphocytes, which can recognize tumor associated antigens (TAAs), followed by infusing them into patients to induce a tumor specific immune response. Despite the recent success in treating hematopoietic malignancies (Maus, et al 2014), limited efficacy has been achieved in treating other solid tumor (Restifo, et al 2012).

One of the main stumbling blocks in the use of ACT is the number of transferred engineered T cells required to achieve therapeutic response is too few once injected into the patient and TILs isolated from malignant lesions readily lose their proliferative potential after ex vivo expansion with a high dose of IL-2 (Kalia et al 2010; Pipkin et al 2010).

To overcome this problem, autologous T cells are genetically engineered T cell receptor (TCR) or chimeric antigen receptor (CAR) to equip them with tumor reactivity, which has resulted in remarkable responses in hematological malignancies (Maude et al 2014). However, the heterogeneity of tumor cells makes this monoclonal T cell approach less efficient to establish durable and complete regression of most tumors. Furthermore, even high numbers of fully activated tumor-specific cytotoxic CD8+ T cells can fail to induce tumor regression due to their insufficient recruitment to tumor tissue (Ganss and Hanahan 1998, Ganss et al 2002 and Garbi et al 2004). The majority of solid tumors are stromal rich with disorganized vasculature, which creates physical barriers for efficient trafficking of therapeutic T cells to the tumor bed (Barnas, et al. 2010; Bellone et al 2013).

Lastly, another equally important major hurdle is the accumulation of immunosuppressive regulatory T cells (Tregs) and myeloid-derived suppressor cells (MDSCs)

within the tumor microenvironment (Curiel et al 2007 and Lu et al 2011), which usually leads to the progressive loss of T cell effector function. Recent studies have shown that depletion of Treg by using either cyclophosphamide (Le et al 2012) or CD25 Abs (Poehlein et al 2009), or MDSC removal by sunitinib (Ko et al 2009) restored tumor-specific T cell responses. With all these limitations, treating solid tumors such as melanoma with immunotherapy remains difficult.

The present disclosure provides a new strategy, using a population of dual-specific lymphocytes that have polyclonal specificity for tumor associated antigens and also specificity for a strong antigen in combination with immunization to the strong antigen intratumorally to target and treat solid tumors. This method we have termed Reenergized ACT (ReACT). This method uses a strong antigen (e.g. a pathogen) not only to break the immunosuppression, but also to drive the expansion and migration of tumor-specific T cells to the very site of tumor. With this combinatorial approach, we have demonstrated that ReACT enhances antitumor efficacy in comparison to either ACT or pathogen-based cancer vaccine alone in primary tumor eradication and offers long-term protection against reoccurrence in preclinical caner models. As demonstrated in the examples, the current method not only reduces tumor burden but has resulted in complete regression of the tumor after treatment.

In some embodiments, the present disclosure provides a purified population of dual-specific lymphocytes which have specificity for two or more antigens. The term "dual-specific lymphocytes" refers to lymphocytes that have specificity for at least two different antigens. The dual specific lymphocytes therefore have at least two receptors the bind to two different antigens. In some embodiments, the dual-specific lymphocytes have specificity for at least one tumor associated antigen and at least one strong antigen. In some embodiments, the dual-specific lymphocytes may be engineered to have a second receptor for a second tumor antigen and/or a second strong antigen. For example, a dual-specific lymphocyte may have specificity for one TAA and one strong antigen, alternatively may have specificity for at least two TAA (e.g. one endogenous TAA and one exogenous TAA genetically engineered into the cell) and at least one strong antigen, alternatively may have specificity for at least one TAA and at least two strong antigens, and the like. Other combinations are also contemplated of at least one TAA and at least one strong antigen.

The present disclosure provides a method of producing an autologous population of dual-specific lymphocytes that can target a plurality of tumor associated antigens and at least one strong antigen. This method comprises the steps of: (a) isolating lymphocytes from a patient; (b) purifying the tumor-specific lymphocytes from the isolated lymphocytes; (c) genetically engineering the purified lymphocytes to express a second receptor specific to a strong antigen, wherein the resulting population comprises dual-specific lymphocytes The autologous dual-specific lymphocytes produced by the methods each express a receptor for a tumor associated antigen (TAA) and are genetically engineered to express an additional receptor for a strong antigen, wherein the population of dual-specific lymphocytes target a plurality of TAAs and the strong antigen.

The term "autologous" herein refers to lymphocytes that are obtained from the patient to be treated. The term "lymphocyte" herein refers to white blood cells that elicit a cell-mediated immune response. Suitable lymphocytes that may be used include, but are not limited to, CD8+ T cells, CD4+ T cells, natural killer (NK) cells and combinations thereof. In a preferred embodiment, the lymphocytes are CD8+ T cells.

In some embodiments, the lymphocytes are tumor infiltrating lymphocytes (TILs). TILs are white blood cells that have left the bloodstream and migrated into a tumor within a patient. TILs can be a mix of different types of cells (i.e., T cells, B cells, NK cells, macrophages) in variable proportions, although T cells are normally the most prevalent.

Methods of isolating lymphocytes from a patient are known in the art. Most preferably, the lymphocytes are isolated from tumor tissue excised from the patient. To create the population of cells to use for the genetic manipulation one would harvest the tumor or a portion of the tumor from a patient as a source of lymphocytes or TILs. For example, one can plate fragments of the tumor in cell culture with cytokines to stimulate lymphocyte growth and expansion.

In some embodiments, a layer of irradiated feeder lymphocytes is used to support the culture of TILs but other methods such as the addition of conditioned media or support cocktails could be employed. One such example of cytokine conditions used to stimulate lymphocyte growth is the addition of 100 IU/ml of interleukin-2, but other cytokines, growth factors and concentrations can be empirically determined and known by one skilled in the art such as the use of interleukin-7 or interleukin-15. Cultures with strong growth will kill the tumor cells leading to cultures enriched for lymphocytes. Next, the clones of lymphocytes are expanded and tested specifically for their ability to kill the primary tumor in a coculture system. Those clones which were able to kill the tumor are selected for gene editing to create a dual-specific lymphocytes. These dual-specific lymphocytes can target not just the tumor but also the strong antigen.

From the excised tumor or tumor fragment, a heterogeneous population of lymphocytes are isolated from the patient. By heterogeneous, the lymphocyte population includes more than one lymphocyte which is specific for more than one tumor associate antigen (TAA). In other words, a population of lymphocytes (e.g. CD8+ T cells) is isolated in which the population contains more than one lymphocyte expressing TCRs that can recognize more than one different TAA. In some embodiments, the dual-specific lymphocyte recognizes at least 2 to tens of thousands of TAAs. Not to be bound by any theory, but since the T cells being activated are polyclonal, they can react to many different tumor associated antigens that are specific to the tumor from which the lymphocytes are isolated. One advantage, among others, of this method is that since the lymphocytes are isolated from the tumor of the patient, they contain a number of endogenous lymphocytes that recognize different TAAs that are specifically expressed in the tumor of that specific patient. These lymphocytes therefore are tumor-specific, patient specific heterologous population providing an advantage over cells that are engineered to only express a single TAA. These lymphocytes are genetically engineered to express a second receptor for a strong antigen.

The second receptor that recognizes a strong antigen may be a second T cell receptor (TCR) or chimeric antigen receptor (CAR). The method of expressing a second receptor in a lymphocyte can be done by standard methods known in the art (e.g. transfection or transduction). For example, a receptor gene may be transduced into the lymphocyte using methods known in the art, for example, a retroviral vector for murine transduction or a lentiviral vector for human transduction. The TCR or CAR is provided as a recombinant DNA molecule comprising all or part of the T-cell receptor nucleic acid sequence within a vector.

A CAR is transmembrane protein containing an extracellular portion containing a recognition or binding site for the strong antigen and a transmembrane and intracellular domain capable of signal transduction to activate the lymphocyte (e.g. T cell). CAR are known in the art and can be made using standard techniques. In one example, the chimeric receptor is a T-cell receptor or fragment thereof which recognize the strong antigen and activates the lymphocyte once bound to the strong antigen. For example, a suitable chimeric receptor is a chimeric containing the single chain variable region from a monoclonal antibody joined to the Fc receptor section capable of mediating T-cell receptor signal transduction. Another chimeric receptor comprises the antibody variable region joined to the cytoplasmic region of CD28 from a T cell or a similar region such as 41BB which can provide a T cell with co-stimulation signal necessary to activate the T cell. One can link the strong antigen receptor of a CAR to an internal signal amplifier such as CD28 or 41BB as would be known by one of skill in the art. Suitable methods of making genetically engineered antigen receptors, and chimeric antigen receptors are known in the art, including, for example, as detailed in Monjezi et al. *Enhanced CAR T-cell engineering using non-viral Sleeping Beauty transposition from minicircle vectors*. Leukemia. 2016 Aug. 5. doi: 10.1038/leu.2016.180; Mock et al. *Automated manufacturing of chimeric antigen receptor T cells for adoptive immunotherapy using CliniMACS prodigy*. Cytotherapy. 2016 August; 18(8):1002-11. doi: 10.1016/j.jcyt.2016.05.009; Jin et al. *Safe engineering of CART cells for adoptive cell therapy of cancer using long-term episomal gene transfer*. EMBO Mol Med. 2016 Jul. 1; 8(7):702-11. doi: 10.15252/emmm.201505869; An et al. *Construction of a new anti-CD19 chimeric antigen receptor and the anti-leukemia function study of the transduced T cells*. Oncotarget. 2016 Mar. 1; 7(9):10638-49. doi: 10.18632/oncotarget.7079; Ren et al. *Modification of cytokine-induced killer cells with chimeric antigen receptors (CARs) enhances antitumor immunity to epidermal growth factor receptor (EGFR)-positive malignancies*. Cancer Immunol Immunother. 2015 December; 64(12):1517-29. doi: 10.1007/s00262-015-1757-6; Oldham R A, Berinstein E M, and Medin J A. *Lentiviral vectors in cancer immunotherapy*. Immunotherapy. 2015; 7(3):271-84. doi: 10.2217/imt.14.108; Review; Urbanska et al. *Targeted cancer immunotherapy via combination of designer bispecific antibody and novel gene-engineered T cells*. J Transl Med. 2014 Dec. 13; 12:347. doi: 10.1186/s12967-014-0347-2, the contents of which are incorporated by reference in their entireties. A chimeric antigen receptor is expressed by a chimeric receptor gene which can be placed into a vector able to express the chimeric receptor gene. Suitable examples for the production of chimeric T-cell receptors and their corresponding genes from production can be found for example in, U.S. Pat. No. 5,830,755 and U.S. application Ser. No. 08/547,263, both of which are incorporated by reference in their entireties.

In some embodiments, the genetically engineering of the lymphocyte comprises transducing the lymphocyte with a gene encoding for the receptor to a strong antigen. By "genetic engineering" we mean the design and introduction of exogenous or foreign DNA into the lymphocyte by those methods known in the art. The term "transduction" means the introduction of exogenous or foreign DNA into the lymphocyte. Suitable methods of transducing the lymphocytes are known in the art and include, but are not limited to, retroviral transduction, adenoviral or other viral transduction methods, electroporation, transfection using lipofection, calcium phosphate, gene transfer or other procedures known to one skilled in the art, including, for example, as discussed in Sambrook et al. (1989), "Molecular Cloning. A Laboratory Manual," Cold Spring Harbor Press, Plainview, N.Y., which is incorporated by reference in its entirety. Suitable vectors and kits are commercially available and known to one skilled in the art for expressing the second receptor. Further, genetic engineering also includes any method which employs any number of enzyme systems that one could use to perform gene editing on the receptor and/or vector, and include, but are not limited to, CRISPR/Cas (Clustered regularly interspaced short palindrome repeats (CRISPRs)), CRISPR-associated Zinc-finger nucleases (ZFNs), and transcription-activator-like effector nucleases (TALENs). These are chimeric nucleases composed of programmable, sequence-specific DNA-binding modules linked to a non-specific DNA cleavage domain. Methods of genetically engineering a cell to express a second receptor are known in the art.

Suitable vectors are known in the art and include expression vectors that comprise at least one expression control element operably linked to the nucleic acid sequence. The expression control elements are inserted in the vector to control and regulate the expression of the nucleic acid sequences and are known in the art, for example promoters and/or enhancers. Suitable vectors include, but are not limited to, adenovirus, retrovirus, cytomegalovirus (CMV), MMLV, SV40, and the like. Additional preferred operational elements include, but are not limited to, leader sequences, termination codons, polyadenylation signals and any other sequences necessary for the appropriate transcription and expression of the nucleic acid. Suitable expression systems and expression vectors are known in the art and one skilled in the art is able to select an expression vector suitable for the cell chosen. It is understood that the vectors may contain additional elements beneficial for proper protein expression, and are well known in the art. In some embodiments, the vectors will include a selectable marker, e.g. ampicillin resistance and/or fluorescent protein expression (e.g. GFP/RFP), that allows for selection of the transduced and/or transformed cells.

In a non-limiting example, the vector to be used for transfection to express a receptor to a strong antigen could be produced as follows: expand peptide-specific T cells isolated from PBMCs of a healthy donor by incubating them with the pathogenic peptide in vitro. For example, for BCG, Geluk et al. identified two HLA-A*0201 restricted CD8 T cell epitopes of Ag85B (BCG derived antigen), these two peptides spanned aa 145-152 FIYAGSLS (SEQ ID NO:1) and aa 199-207 KLVANNTRL (SEQ ID NO:2). In this example, one would choose one of the two peptides to expand T cells in vitro. Next, one can isolate peptide-specific T cells by fluorescence-activated cell sorting (FACS), selecting for CD8 T cells carrying the activation marker CD45RO (marker for effector and memory T cells). DNA isolated from these T cells can be subjected to next generation sequencing to identify the most abundant variable regions of alpha and beta chain of clonal T cell receptors (TCRs). The sequencing results will indicate the dominant TCR. The dominant TCR sequences identified will be used to construct a vector that co-expresses both alpha and beta chains of the TCR, which can then be used to express the TCR in lymphocytes.

In a preferred embodiment, the lymphocytes are transfected using a retroviral or lentivral vector system, wherein the lymphocytes are incubated with retroviral or lentiviral supernatant in a concentration of about $1 \times 10^2$ to about $1 \times 10^{10}$ viral particles per ml. Preferably, lentiviral vectors are used in human subjects.

In some embodiments, the vector further comprises a selection marker that can be used to select the transduced cells.

The term "strong antigen" refers to an antigen able to induce proliferation of lymphocytes (including T cells). The strong antigen is able to induce proliferation when exposed to the lymphocytes either in vitro or in vivo. The term strong antigen may refer to a single antigen or a set of antigens. Suitable strong antigens include, but are not limited to, pathogens (e.g. viral antigens or bacterial antigens) and alloantigens. In some embodiments, the pathogen may be an attenuated form of the microorganism, any pathogen that is suitable for vaccination and clinical use in humans. Suitable strong antigens include, but are not limited to, live or attenuated bacteria, virus, human leukocyte antigen, major histocompatibility complex, a pathogenic protein or a protein or peptide fragment of any of the aforementioned.

Alloantigens are antigens derived from genetically non-identical members of the same species. Alloantigens may be tissues, cells, proteins, or peptides, e.g. HLAs.

In some embodiments, the strong antigen is an antigen from a pathogen, wherein the pathogen is selected from the group consisting of *Listeria monocytogenes, Bacillus* CalmetteGuérin, tetanus, diphtheria, adenovirus, herpes simplex virus, vaccinia virus, myxoma virus, poliovirus, vesicular stamatis virus, measles virus, Newcastle disease virus and combinations thereof. Other suitable pathogens that are in human trials and may be used in the practice of the present technology include:
   (a) Adenovirus 5 (dl1520 derivative) Squamous cell carcinoma of head and neck (approved drug in China; intratumoural);
   (b) Adenovirus 5 (PSE-E1A and E3 deleted) Prostate (I; prostatic);
   (c) Herpes simplex virus 1 (ICP34.5 defective) Glioblastoma multiforme (II; intratumoural);
   (d) Vaccinia virus (thymidine kinase knockout and expressing granulocyte-macrophage colony-stimulating factor) Advanced liver tumours (I-II; intratumoural);
   (e) Reovirus (reolysin) Superficial tumours (I; intralesional);
   (f) Newcastle disease virus (PV701) Bladder, squamous cell carcinoma of head and neck and ovarian (I-II; intravenous);
   (g) Measles virus (V protein knockout and expressing the reporter carcinoembryonic antigen or the effector sodium iodide symporter) Ovarian (I; intratumoural), glioma.

In some cases, a pathogen marker can be used in order to track, find or boost responsiveness to the pathogen. In the example shown, a portion of the ovalbumin protein was expressed as an antigen secondary to the pathogen. Specifically, OVA SIINFEKL peptide (SEQ ID NO:3) (responding to recombinant *Listeria Monocytogenes*-OVA, LM-OVA).

The methods of producing dual-specific lymphocytes of the present technology include the step of culturing the lymphocytes in vitro. During this culturing step, the lymphocytes are selected/activated and purified that are specific to one or more tumor associated antigens by methods known in the art. For example, one method to culture and purify the lymphocytes that are specific to tumor cells of the patient is to culture the lymphocytes in the presence of tumor cells isolated from the patient or to one or more tumor associated antigens. In the preferred embodiment, the lymphocytes are cultured with tissue, cells, or parts of tissue from the tumor of the patient. Otherwise, suitable tumor associated antigens to culture the cells with are known in the art and may be specific to the specific type of tumor being treated. For example, a listing of tumor antigens that can be used for culturing can be found on-line in the Peptide Database, for example, but not limited to, the TAAs such as AFP (Alpha-feto protein), ALK gene rearrangements, B-cell immuno-globulin gene rearrangement, B2M (Beta-2 microglobulin), BCR-ABL, CA 15-3 (Cancer antigen 15-3), CA 19-9 (Cancer antigen 19-9), CA-125 (Cancer antigen 125), Calcitonin, CEA (Carcino-embryonic antigen), Chromogranin A(CgA), DCP (Des-gamma-carboxy prothrombin), EGFR mutation, Estrogen and Progesterone receptors, Fibrin/Fibrinogen, Gastrin, hCG (Human chorionic gonadotropin, also called Beta-hCG), HER2/neu, JAK2 mutation, KRAS mutation, LD (Lactate dehydrogenase), Monoclonal immunoglobu-lins, PSA (Prostate specific antigen), SMRP (Soluble meso-thelin-related peptides), T-cell receptor gene rearrangement, Thyroglobulin, 21-gene signature (Oncotype DX®) and 70-gene signature (MammaPrint®), and others known in the art. A suitable method for culturing the lymphocytes can be found in van der Bruggen P, Stroobant V, Vigneron N, Vanden Eynde B. Peptide database: T cell-defined tumor antigens. Cancer Immun. 2013, which is incorporated by reference in its entirety.

The culturing step may also include a step of culturally expanding the tumor cells to increase the number of tumor specific lymphocytes that are able to be transferred back into a patient. Suitable methods for expanding the in vitro cultured lymphocytes are known in the art. In one embodiment, the specific expanding step amplifies a subpopulation of T cells whose endogenous T cells are directed to a plurality of tumor associated antigens from the tumor of the patient. This produces a heterogeneous population of autologous lymphocytes (e.g. CD8+ T cells) that can recognize a plurality of tumor associated antigens specific to the patient. These expanded heterogeneous population of lymphocytes are then further transduced with the second receptor (e.g. an exogenous TCR or chimeric antigen receptor) to produce the dual-specific lymphocytes.

In some embodiments of the method, the genetically-engineered dual-specific lymphocytes are cultured in the presence of both the tumor associated antigens (or tissue or cells from the tumor of the patient) and the strong antigen to increase the number of cells reactive to both the TAA and the strong antigen. In other words, the dual-specific lympho-cytes are stimulated with the strong antigen and/or a plurality of TAAs in culture to proliferate. In some embodiments, the lymphocytes, for example CD8+ T cells are cultured with IL-2 to increase the number of dual-specific lymphocytes in the culture.

In some embodiments, the lymphocytes are activated with the strong antigen to result in proliferation of the dual-specific lymphocytes. In some embodiments, the lymphocytes are exposed to the strong antigen for greater than one hour, in some embodiments for at least 24 hours. The lymphocytes are preferably exposed to the strong antigen continuously for this time. Suitably, pathogenic antigens are exposed for at least 1 hour to the lymphocytes, including at least 2 hours, at least 3 hours, at least 4 hours, at least 5 hours, at least 6 hours, at least 10 hours, at least 12 hours, at least 14 hours, at least 16 hours, at least 18 hours, at least 20 hours, at least 24 hours, and includes any amount of time in between. Suitably, alloantigens are exposed to the lymphocytes for at least 24 hours, alternatively at least 30 hours, alternatively at least 48 hours. Suitable amounts of strong antigen to expose the dual-specific lymphocytes will depend on the strong antigen, and are able to be determined by one skilled in the art. For example, the strong antigen may be provided in a concentration of about 0.1 to about 1 mM for proteins, peptides or cellular components. For infectious or inactivated viral particles, they can be provided at a ratio of from 1-1000 viral particles per cell in culture. Similarly, the number of allogenic cells that may be used can be from 1 to 100 per lymphocyte in culture. In some embodiments, the strong antigen is combined with one or more TAAs, including, in some embodiments, the inclusion of tissue or cells from the tumor extracted from the patient.

As used herein, the term plurality means two or more.

As used herein the term patient and subject can be used interchangeably. The patient is suitably a mammal, more preferably a human. In some embodiments, the compositions and methods may be used to treat a mammal, for example, a human, a chimpanzee, a mouse, a rat, a dog, a cat, a horse or other livestock. In the most preferably embodiment, the method is used to treat a human.

The present disclosure provides methods of treating a patient with a tumor. The method comprises administering to the patient an effective amount of the autologous dual-specific lymphocytes described herein or autologous population of dual-specific lymphocytes made by the methods described herein and injecting the patient with a strong antigen, and preferably injecting the strong antigen intratumorally. Pathogens have natural predilictions or tropisms for infection and replication in certain areas of the body. Influenza infects and damages the respiratory tract primarily but the central nervous system only secondarily or in rare cases. Poliovirus infects and damages the central nervous system primarily but the respiratory system only secondarily. Using the knowledge of a pathogens natural tropism, one of skill in the art could select a strong antigen from a pathogen that had tropism for the location of the tumor to be treated. For example, if one wanted to treat a lung tumor, one might use as the strong antigen of choice a strong antigen from influenza and then use a strategy of injecting or intranasally delivering an influenza vaccine. Though the preferred method of local delivery in many cases will be injection, other mechanisms of delivering the strong antigen to the site of the tumor could be used such as intranasal delivery, gavage, lavage, or topical delivery.

By "treating" or "treatment" we mean the management and care of a subject for the purpose of combating and reducing the tumor. Treating includes the administration of a dual-specific lymphocytes of the present invention to reduce, inhibit, ameliorate and/or improve the onset of the symptoms or complications, alleviating the symptoms or complications of the tumor, or eliminating the tumor. Specifically, treatment results in the reduction in tumor load or volume in the patient, and in some instances, leads to regression and elimination of the tumor or tumor cells. As used herein, the term "treatment" is not necessarily meant to imply cure or complete abolition of the tumor. Treatment may refer to the inhibiting or slowing of the progression of the tumor, reducing the incidence of tumor, reducing metastasis of the tumor, or preventing additional tumor growth. In some embodiments, treatment results in complete regression of the tumor.

By "ameliorate," "amelioration," "improvement" or the like we mean a detectable improvement or a detectable change consistent with improvement occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range about between any two of these values. Such improvement or change may be observed in treated subjects as compared to subjects not treated with the dual-specific lymphocytes and immunization with a strong antigen of the present invention, where the untreated subjects have, or are subject to developing, the same or similar tumor.

In some embodiments, the injecting step (in other words, the in vivo immunization step) of the strong antigen into the tumor serves to activate the adoptively transferred dual-specific lymphocytes (e.g. CD8+ T cells) and to further home or target the transferred lymphocytes to the tumor. Not to be bound by any theory, it is believed that the injection of the strong antigen to the tumor cells overcomes the immunosuppression of the tumor environment and results in a larger amount of the transferred dual-specific lymphocytes (e.g. CD8+ T cells) being recruited to the tumor which leads to increase tumor killing and tumor cell death.

In some embodiments, the method comprises administering an effective amount of the compositions described herein comprising a population of autologous dual-specific lymphocytes and a pharmaceutically acceptable carrier and injecting/immunizing the patient with the strong antigen.

In the preferred embodiment, the compositions or dual-specific lymphocytes are administered intravenously into the patient. In some embodiments, other methods of administration are contemplated, for example, intra-arterially, intratumorally, parenterally, and the like.

The injecting of the strong antigen may be administered co-currently with the administration (adoptive transfer) of the dual-specific lymphocytes or can be done sequentially. In some embodiments, a second injection of the strong antigen is performed into the tumor. In other embodiments, multiple injections of the strong antigen or multiple deliveries of the genetically altered patient immune cells over many months or years could be beneficial. A physician would monitor risk profiles and tumor burden to empirically determine a treatment schedule for a given patient.

A pharmaceutical composition comprising: a population of autologous dual-specific lymphocytes reactive to at least one tumor associated antigen and containing a genetically engineered receptor reactive with a strong antigen a pharmaceutically acceptable carrier. The dual-specific lymphocytes are selected to be reactive with a plurality of tumor associated antigens specific to a tumor.

By "pharmaceutically acceptable carrier" we mean any and all solvents, dispersion media, antibacterial and antifungal agents, isotonic agents, solutions or media and the like that are physiologically compatible and do not result in harm to the dual-specific lymphocytes during preparation, storage or administration. The pharmaceutical compositions may optionally include one or more additional ingredients depending on the mode of administration and the dual-specific lymphocytes or strong antigen to be administered to maintain the activity of the dual-specific lymphocytes or strong antigen during storage, preparation and administration. Suitably, in some embodiments, the pharmaceutical composition may contain additives such as pH-adjusting additives, anti-microbial preservatives, stabilizers and the like. Preferably, the carrier is suitable for intravenous, parenteral, intraperitoneal, or intramuscular administration. Pharmaceutically acceptable carriers include sterile aqueous solutions or dispersions, including for example, saline or phosphate buffer saline. The use of such media and agents for pharmaceutically active substances is well known in the art. Except insofar as any conventional media or agent is incompatible with the lymphocytes, use thereof in the pharmaceutical compositions of the invention is contemplated. Additional agents or therapies can also be incorporated into the compositions.

The pharmaceutical compositions described herein may be formulated with the lymphocytes in a pharmaceutical carrier in accordance with known techniques. See, e.g., Remington, The Science And Practice of Pharmacy 9th Ed. (A. R. Gennaro, ed., Mack Publishing Co., Easton, Pa., 1995). Also, the strong antigens may be formulated with a pharmaceutical carrier in accordance with known techniques for injection.

The inventor has surprisingly discovered a method to boost T cell responses to tumor by artificially engineering a T cell to respond to a second strong antigen in addition to polyclonal recognition of tumor antigens, as described in the examples. In the following example, CD8 T cells from the Pmel-1 CD8 transgenic mouse in which 95% of CD8 T cells express a T cell receptor (TCR) namely V alpha 1 and V beta 13. These T cells recognize an epitope of melanoma tumor associated antigen (TAA) gp100. Using a retroviral vector, OT-I TCR (V alpha 2 and V beta 5), which recognizes ovalbumin (OVA) residues 257-264 and produces green fluorescent protein (GFP) was transduced into the Pmel-1 CD8 T cells resulting in cells which would express three important substances which include: receptors for the gp100 tumor associated antigen; receptors for OVA which can be inoculated into the tumor to additionally target the T cells to the tumor environment and boost their responsiveness; and GFP a molecule useful in the isolation, purification and later tracking of the artificially engineered cells.

Other types of immune cells, tumor antigens, pathogens and pathogen markers may be used.

The population of dual-specific lymphocytes, compositions and methods of this disclosure can be used to treat a patient suffering from a tumor. More preferably, the tumor is a solid tumor. Suitable tumors that can be treated by the methods described herein include, but are not limited to, a tumor selected from the group consisting of a sarcoma, a carcinoma and a melanoma. Suitable solid tumors that can be treated by the method include, but are not limited to, brain and other central nervous system tumors; head and/or neck cancer; breast tumors; circulatory system tumors (e.g. heart, mediastinum and pleura, and other intrathoracic organs, vascular tumors and tumor-associated vascular tissue); excretory system tumors (e.g. kidney, renal pelvis, ureter, bladder, other and unspecified urinary organs); gastrointestinal tract tumors (e.g. esophagus, stomach, small intestine, colon, colorectal, rectosigmoid junction, rectum, anus and anal canal), tumors involving the liver and intrahepatic bile ducts, gall bladder, other and unspecified parts of biliary tract, pancreas, other and digestive organs); oral cavity; uterine cancer, ovarian cancer, penile cancer, prostate cancer, testicular cancer; respiratory tract tumors (e.g. nasal cavity and middle ear, accessory sinuses, larynx, trachea, bronchus and lung, e.g. small cell lung cancer or non-small cell lung cancer); skeletal system tumors (e.g. bone and articular cartilage of limbs, bone articular cartilage and other sites); skin tumors (e.g. malignant melanoma of the skin, non-melanoma skin cancer, basal cell carcinoma of skin, squamous cell carcinoma of skin, mesothelioma, Kaposi's sarcoma); and tumors involving other tissues. In some preferred embodiments, which may be commercially relevant include, but are not limited to, bladder cancer using BCG as strong antigen, pancreatic cancer using *listeria* as strong antigen, melanoma using vaccinia as strong antigen and lung cancer using influenza as strong antigen.

This disclosure also provides kits. The kits can be suitable for use in the methods described herein. Suitable kits include a kit for treating a tumor comprising genetically engineered autologous dual-specific lymphocytes described above and an injectable composition comprising the strong antigen.

In some embodiments, a kit for producing dual-specific lymphocytes are contemplated. In one embodiment, the kit comprises a vector encoding a receptor specific to a strong antigen able to be expressed in a cell is provided.

In another embodiment, a kit comprising: (a) a vector encoding a receptor specific to a strong antigen able to be expressed in a cell; (b) a system for transducing the vector into lymphocytes; and (c) instructions for isolating tumor infiltrating lymphocytes from a tumor of a patient and transducing them with the strong antigen receptor are provided. The cell is preferably a lymphocyte, more preferably a CD8+ T cell.

In some embodiments, kits for carrying out the methods of the present disclosure are provided. For example, a kit for producing a population of dual-specific lymphocytes, more specifically CD8+ T cells is provided. The kit provides a vector encoding a receptor specific to a strong antigen and the strong antigen. Instructions are provided that describes the method of isolated tumor-specific lymphocytes from a patient, culturing the isolated lymphocytes from the patient, transducing the lymphocytes to express the receptor for the strong antigen, and methods of using the duel specific lymphocytes for treatment of a tumor are provided. In some embodiments, the instructions further provide methods for culturally expanding and/or activating the lymphocytes.

The following non-limiting examples are included for purposes of illustration only, and are not intended to limit the scope of the range of techniques and protocols in which the compositions and methods of the present invention may find utility, as will be appreciated by one of skill in the art and can be readily implemented.

Example 1: Population of Dual-Specific CD8T Cells which Recognize a Plurality of Tumor Associated Antigen Specific for the Subject and a Bacterial Antigen and Use for Treating of Solid Tumors Immunosuppressive tumor microenvironment, insufficient migration and reduced effector function of tumor-specific T cells are the main hurdles that hamper the efficacy of immunotherapy in treating solid tumors. In this example, we combined the strength of adoptive cell transfer (ACT) and pathogen-based cancer vaccine and developed an innovative strategy, Reenergized ACT (ReACT), to treat solid tumors. ReACT uses a pathogen not only to break the immunosuppression, but also to drive the expansion and migration of tumor-specific T cells to the very site of tumor. With this combinatorial approach, we have demonstrated that ReACT enhances antitumor efficacy in comparison to either ACT or pathogen-based cancer vaccine alone in primary tumor eradication; and offers long-term protection against reoccurrence in preclinical caner models.

To overcome the hurdles of immunosuppression and induce a vigorous antitumor T cell response, we combined the strength of ACT and pathogen-based cancer vaccines with a new strategy named Reenergized ACT (ReACT). To bridge ACT with a pathogen, we genetically engineered populations of tumor-reactive CD8 T cells with a second T cell receptor (TCR) specific to a bacterial antigen to create dual-specific CD8 T cells (i.e., a single T cell capable of recognizing two antigens). This technology is based on a system developed by Kershaw and colleagues (12,13). However, our dual-specific CD8 T cells have advantages and differ from Kershaw in that we have a population of CD8 T cells which express a plurality of different TCR specific to different tumor antigens that additionally express a genetically engineered TCR specific to a strong antigen, in this Example a TCR specific for the bacteria Listeria. We then used a pathogen-based vaccine to drive the robust expansion of adoptively transferred bacteria- and tumor- (dual) specific T cells, recruit them to the tumor site, and concomitantly reverse immunosuppression in the tumor microenvironment. This combined approach has demonstrated robust efficacy in primary tumor eradication and long-term protection against recurrence in preclinical cancer models. Not to be bound by any theories, but it is our belief that our engineered dual-specific CD8 T cells provides a superior immune response to the tumor as opposed to ACT using dual-specific CD8 T cells that are genetically engineered to express a specific tumor antigen which may not react to all tumor cells, leaving some tumor cells that do not express that specific tumor antigen or express low levels of the specific tumor antigen to expand and replace the targeted tumor cells.

Results

ReACT Enhances Antitumor Efficacy

First, we used a well-established mouse B16-F10 melanoma model (14) to test the antitumor efficacy of ReACT. To generate dual-specific CD8 T cells, we started with Pmel-1 CD8 T cells, which express a TCR (Vα1 and Vβ13) that recognizes the gp100 epitope of murine melanoma (14). These cells were then genetically engineered to express OT-I TCR (Vα2 and Vβ5) by retroviral transduction in vitro (FIG. 1A). OT-I recognizes ovalbumin (OVA) residues 257-264, which served as a surrogate bacterial antigen expressed in a recombinant LM-OVA. We chose Listeria as a model organism because it is amenable to clinical use, and attenuated Listeria, like many other pathogen-based cancer vaccines, has shown promising antitumor effects in multiple cancer models in humans (ClinicalTrails.gov) and mice (9). To validate dual-specificity, control (empty vector transduced; referred to as mono-specific CD8 T cells henceforth) and OT-I-TCR transduced (referred to as dual-specific CD8 T cells henceforth) Pmel-1 cells were stimulated by antigenic peptides. Mono-specific CD8 T cells produced IFNγ after stimulation with gp100 but not $OVA_{257-264}$ peptide (FIG. 1B). In contrast, dual-specific CD8 T cells responded to both gp100 and $OVA_{257-264}$ peptides (FIG. 1B).

To test the ability of transduced mono-specific or dual-specific CD8 T cells to control melanoma in a therapeutic setting, a small number of cells ($5\times10^5$/mouse) were adoptively transferred into C57BL/6 mice with established subcutaneous B16-F10 melanoma tumors. Consistent with previously published data (14), both ACT regimens failed to prevent the tumor growth (FIG. 1C). However, when dual-specific CD8 T cells were administered in combination with a low dose of LM-OVA (ReACT), there was significant tumor regression in all mice and the majority of mice (7 out of 10) had complete eradication (FIGS. 1C-1D). Notably, antitumor effects required that mice were treated with both dual-specific T cells and LM-OVA as tumor growth was only slightly and transiently suppressed in mice that received mono-specific CD8 T cells and LM-OVA (FIGS. 1C-1D). Together, these results validate the feasibility of our approach and clearly show that ReACT leads to significantly enhanced antitumor efficacy.

The Adjuvant Effect of Listeria

Figures 2A, 2B:
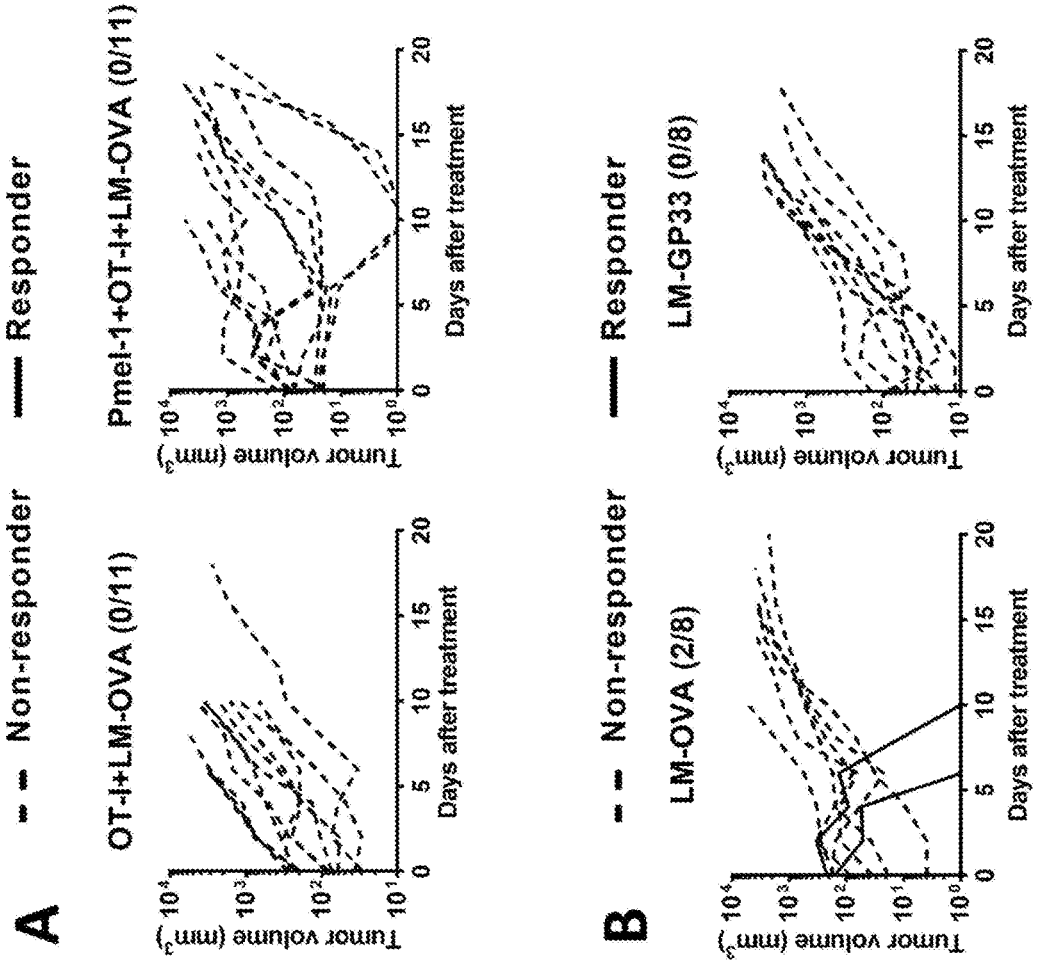
FIGS. 2A-2B shows the adjuvant effect of Listeria and the antitumor effect of LM-OVA as a cancer vaccine.

It is possible that ReACT mediated tumor eradication was due to a bystander anti-bacterial effect from the dual-specific CD8 T cells. To test this possibility, we first transferred OT-I (OVA/bacteria-specific, non-transduced) CD8 T cells either alone or with Pmel-1 (tumor-specific) CD8 T cells into B16-F10 melanoma tumor bearing mice, and then intratumorally administered LM-OVA. Regardless of the robust expansion of OT-I cells in response to LM-OVA infection and their migration to tumors, no obvious therapeutic benefit was seen in the OT-I+LM-OVA group as compared to FIG. 1D (FIG. 2A and data not shown). In the same vein, bystander OT-I response to LM-OVA only conferred transient adjuvant effects and failed to eradicate tumors even in the presence of Pmel-1 cells (FIG. 2A and data not shown). These results together with the data shown in FIG. 1 demonstrated that LM-OVA infection either with mono-specific T cells alone (Pmel-1 or OT-I) or mixed mono-specific T cells (Pmel-1 and OT-I) was insufficient to eradicate tumors. Without expansion of adoptively transferred tumor-specific CD8 T cells, LM-OVA shows limited adjuvant effects in tumor control.

The Antitumor Effect of LM-OVA as a Cancer Vaccine

Recombinant Listeria expressing TAAs can serve as cancer vaccines to treat solid tumors (9). To test if a LM-based vaccine could confer similar tumor control as seen by ReACT, we compared two recombinant stains of Listeria, LM-OVA (expressing LCMV glycoprotein 33-41 residues) and LM-GP33 (irrelevant control GP33 peptide) in the B16-OVA melanoma tumor model. To test proof-of-principle and for simplicity, we used $OVA_{257-264}$ as a surrogate tumor antigen as reported previously (15). We administrated LM-OVA and LM-GP33 i.t. to C57BL/6 mice with established B16-OVA melanoma and followed the tumor progression over time. Consistent with previous published work (16), LM-OVA led to a greater tumor control and 25% eradication when compared with LM-GP33 treated mice (FIG. 2B). Nonetheless, this approach did not render robust tumor eradication as seen in ReACT treated mice (FIG. 1D). Taken together, our data suggest that combinatorial treatment with ACT and a pathogen-based cancer vaccine leads to much greater tumor control than either treatment alone.

Polyclonal ReACT Eradicates Tumor and Generates Long-Term Protection

Figures 3A, 3B, 3C, 3D:
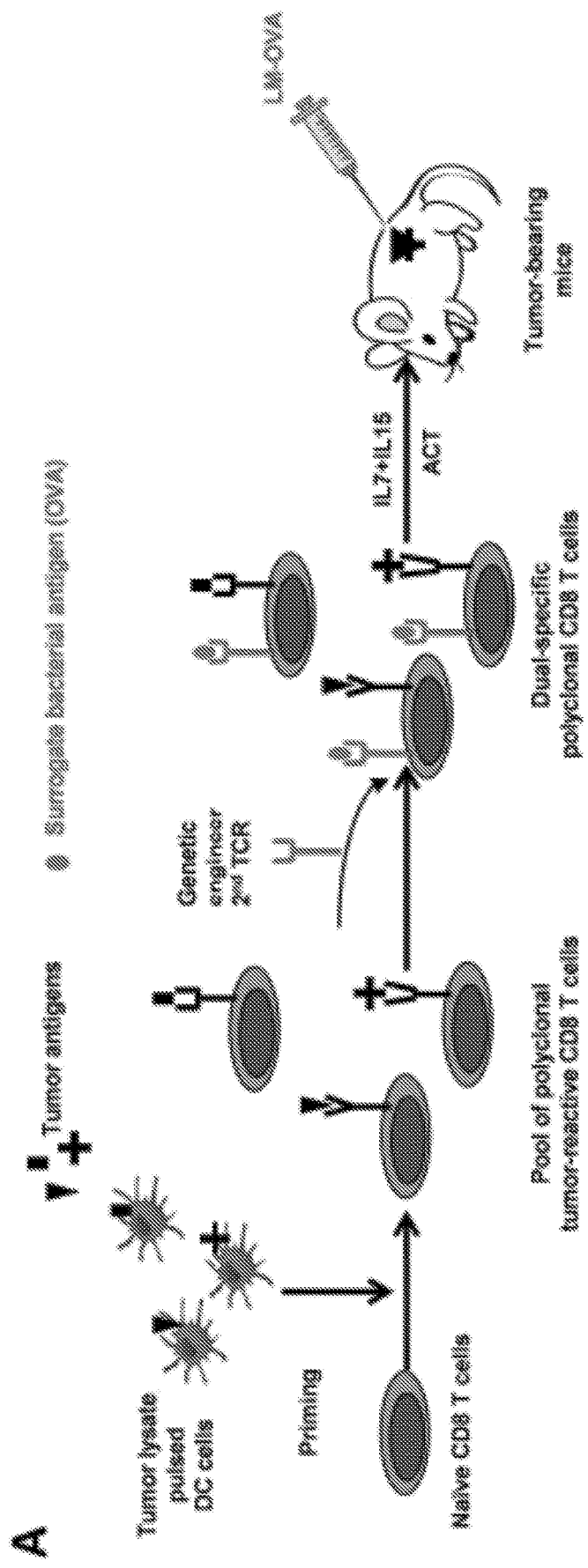
FIGS. 3A-3D show Polyclonal ReACT confers efficient tumor control and generates long-term protection.
Figures 3A, 3B, 3C, 3D:
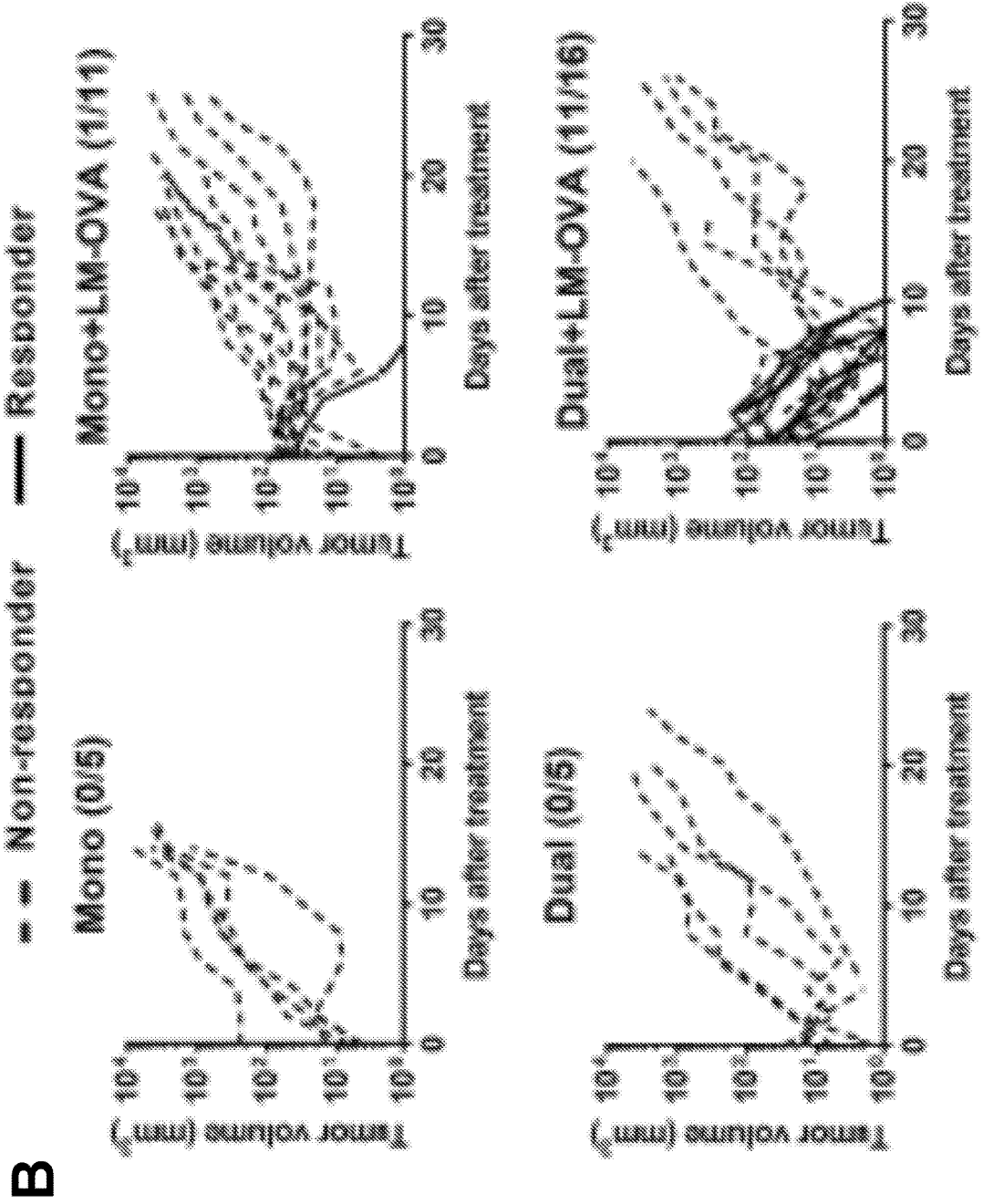
Figures 3A, 3B, 3C, 3D:
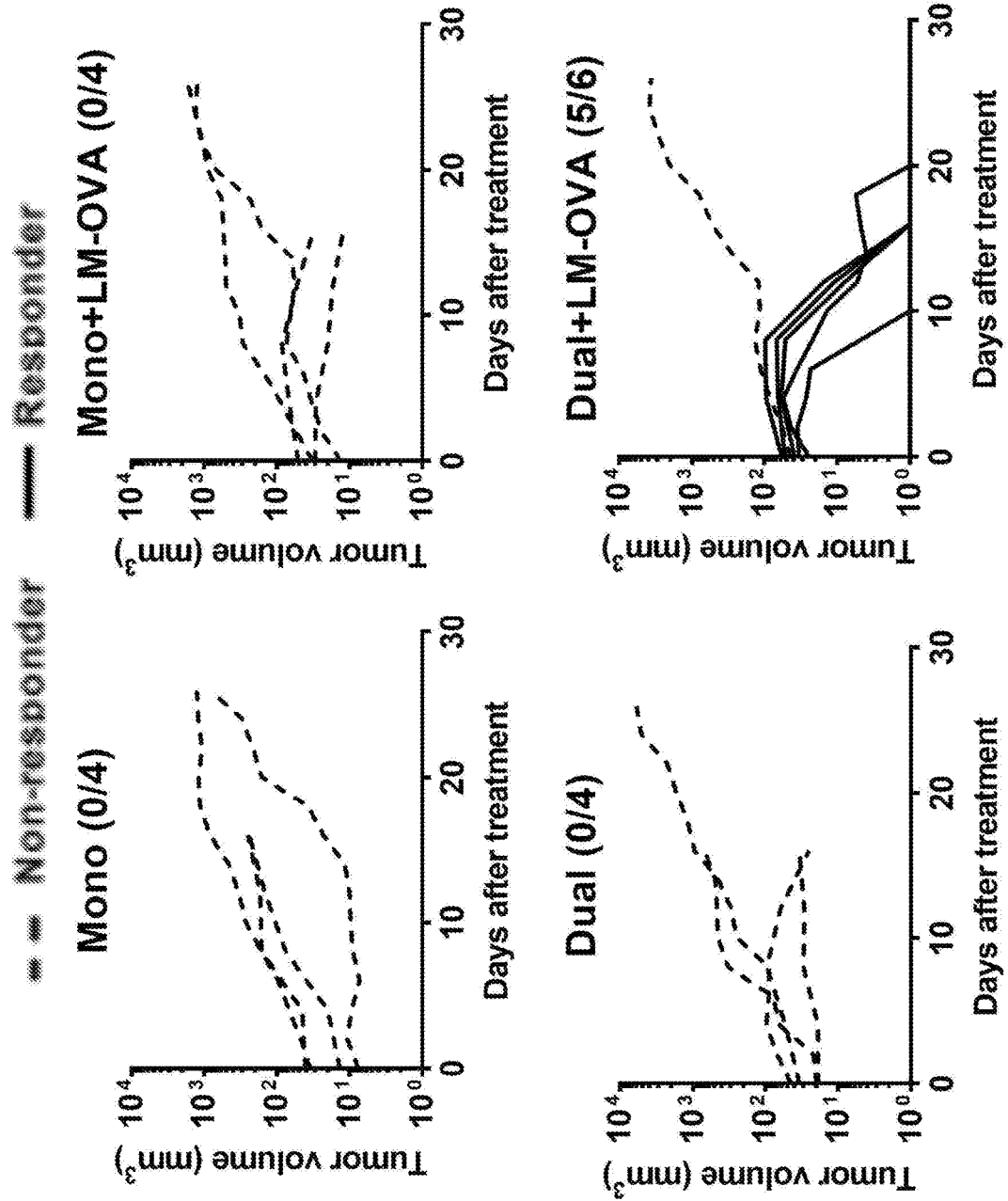
Figures 3A, 3B, 3C, 3D:
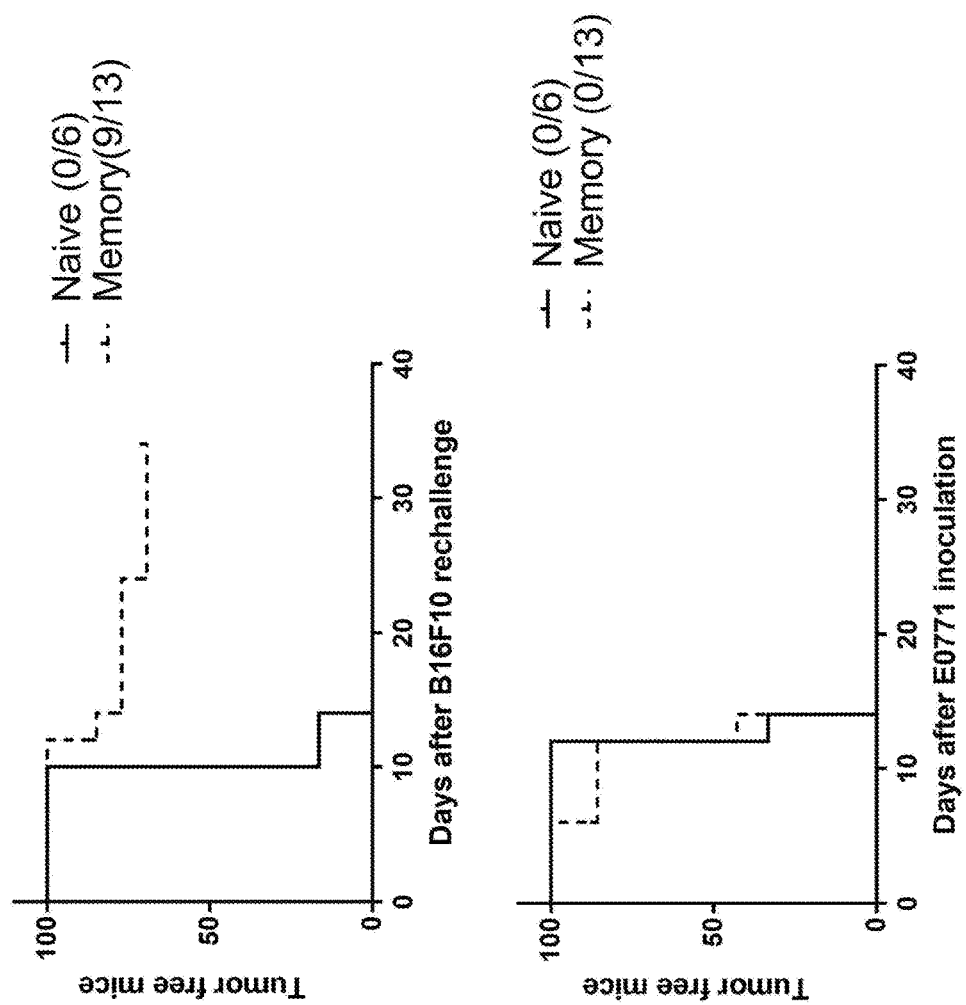
Figures 6A, 6B:
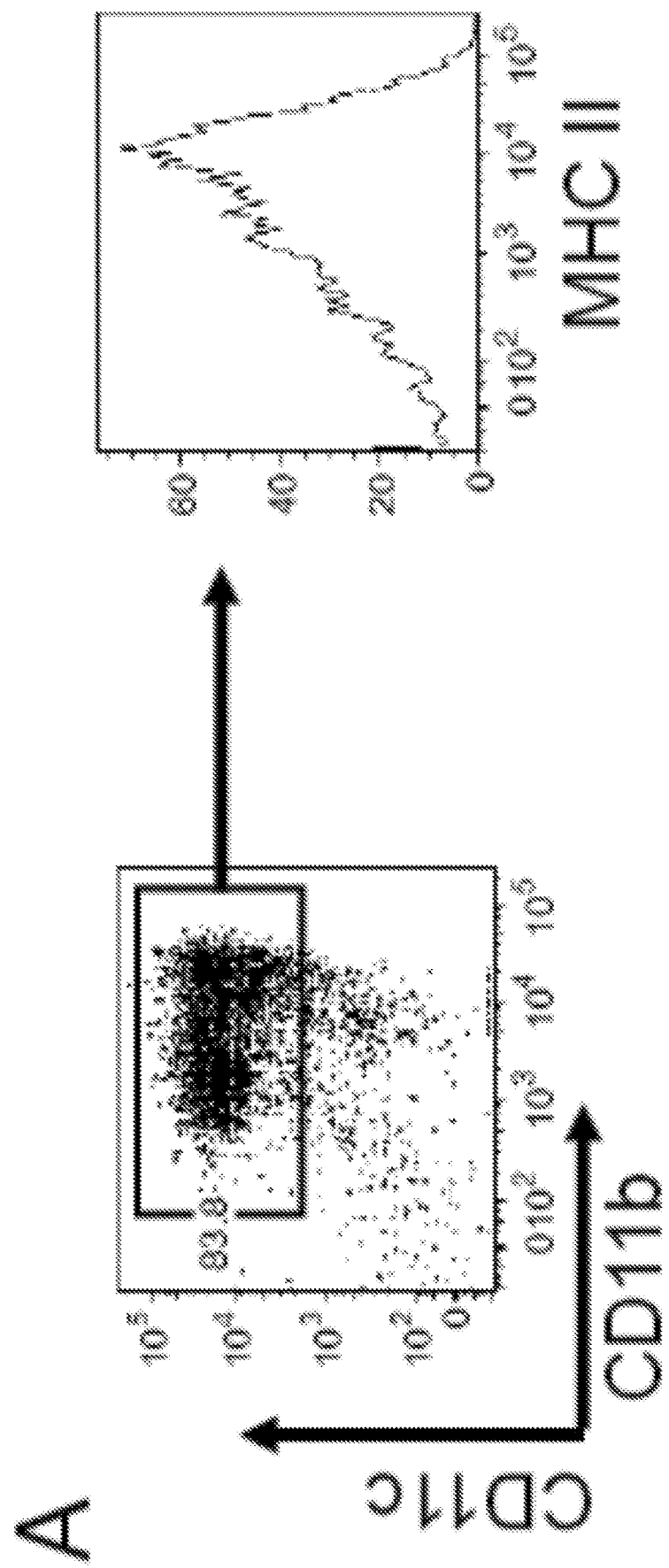
FIGS. 6A-6B show the phenotypes of bone marrow derived dendritic cells (BMDCs) and polyclonal dual-specific CD8 T cells.
Figures 6A, 6B:
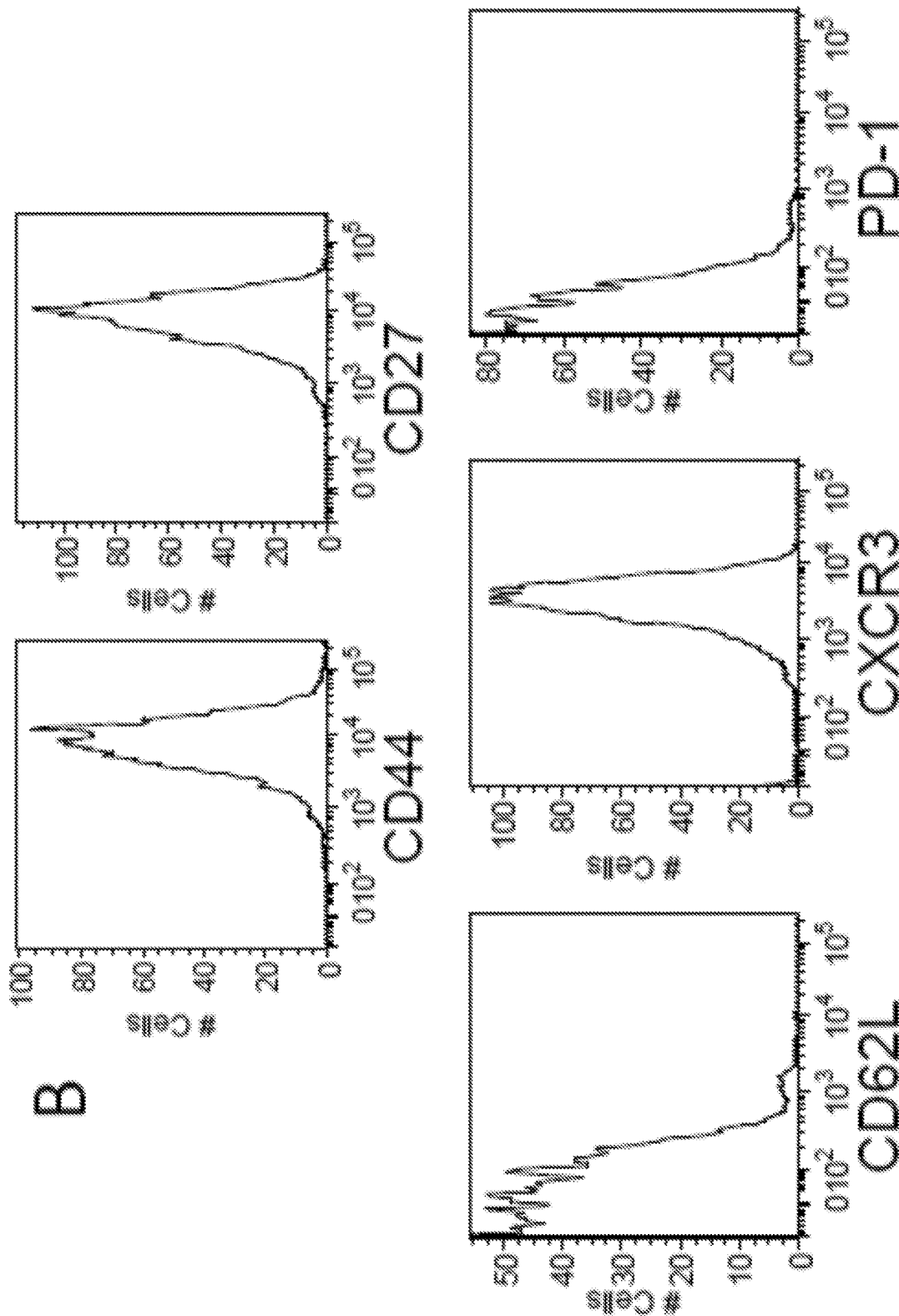

Given the lack of well-defined TAAs for most human tumors, and the advantages of using naturally occurring tumor-infiltrating lymphocytes (TILs) that recognize multiple TAAs to treat cancer patients (2), we further tested proof-of-principle by generating polyclonal CD8 T cells that target one bacterial antigen and multiple tumor antigens (FIG. 3A). For simplicity, we used B16-F10 cell lysate pulsed DCs to stimulate naïve CD8 T cells to differentiate them into effector cytotoxic T cells (CTLs) that recognize various B16-F10 derived tumor antigens as shown previously (17). These cells were then genetically engineered to express the OT-I TCR and are referred to as polyclonal dual-specific CD8 T cells (FIG. 3A and FIGS. 6A-6B).

In line with the preceding observations, transfer of neither mono-specific nor dual-specific polyclonal CD8 T cells alone generated therapeutic responses against tumor growth in the absence of LM-OVA infection (FIG. 3B). The combination of polyclonal mono-specific CD8 T cells with LM-OVA infection only resulted in tumor elimination in 1 of 11 mice (FIG. 3B). Strikingly, combined polyclonal dual-specific CD8 T cells and LM-OVA infection (ReACT) led to complete tumor eradication in the majority of mice (11 of 16) (FIG. 3B). Similar results were obtained in the E0771 breast cancer model (FIG. 3C), demonstrating that this therapy could potentially be applied to various types of solid tumors.

To test if this combined therapy could generate immunological memory that protects the hosts from tumor recurrence, we challenged mice that had eradicated primary melanoma (B16-F10) tumors with a lower dose of B16-F10 cells on the left flank, and with a previously unencountered cancer line (E0771 breast cancer cells) on the right flank. The majority of these mice (7 out of 10) were resistant to B16-F10, whereas none rejected the E0771 (FIG. 3D). As expected, naïve mice did not reject either B16-F10 or E0771 tumors (FIG. 3D). These data illustrate that the polyclonal ReACT approach not only provides an enhanced immune response to eradicate primary tumor, but also establishes long-term protective immunity that prevents tumor relapse.

ReACT Increases CD8 T Cell Expansion, Function and Tumor-Targeted Migration

Figures 4A, 4B, 4C, 4D, 4E, 4F:
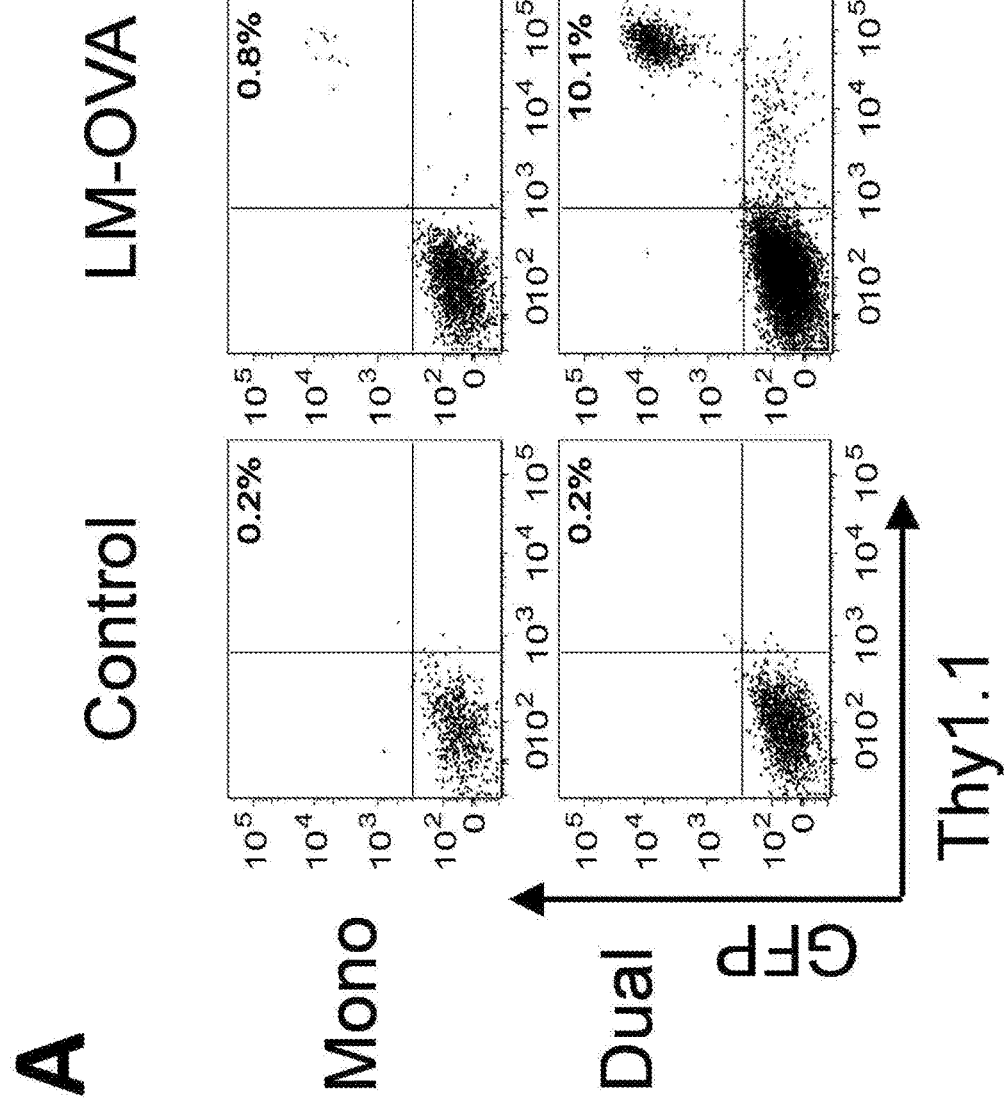
FIGS. 4A-4F show ReACT markedly increases tumor-specific CD8 T cell expansion, function and tumor-targeted migration. C57BL/6 mice received various combinations of treatments described in FIG. 1. Ten days later, mice were euthanized to harvest tumor infiltrating immune cells for flow cytometric analysis.
Figures 4A, 4B, 4C, 4D, 4E, 4F:
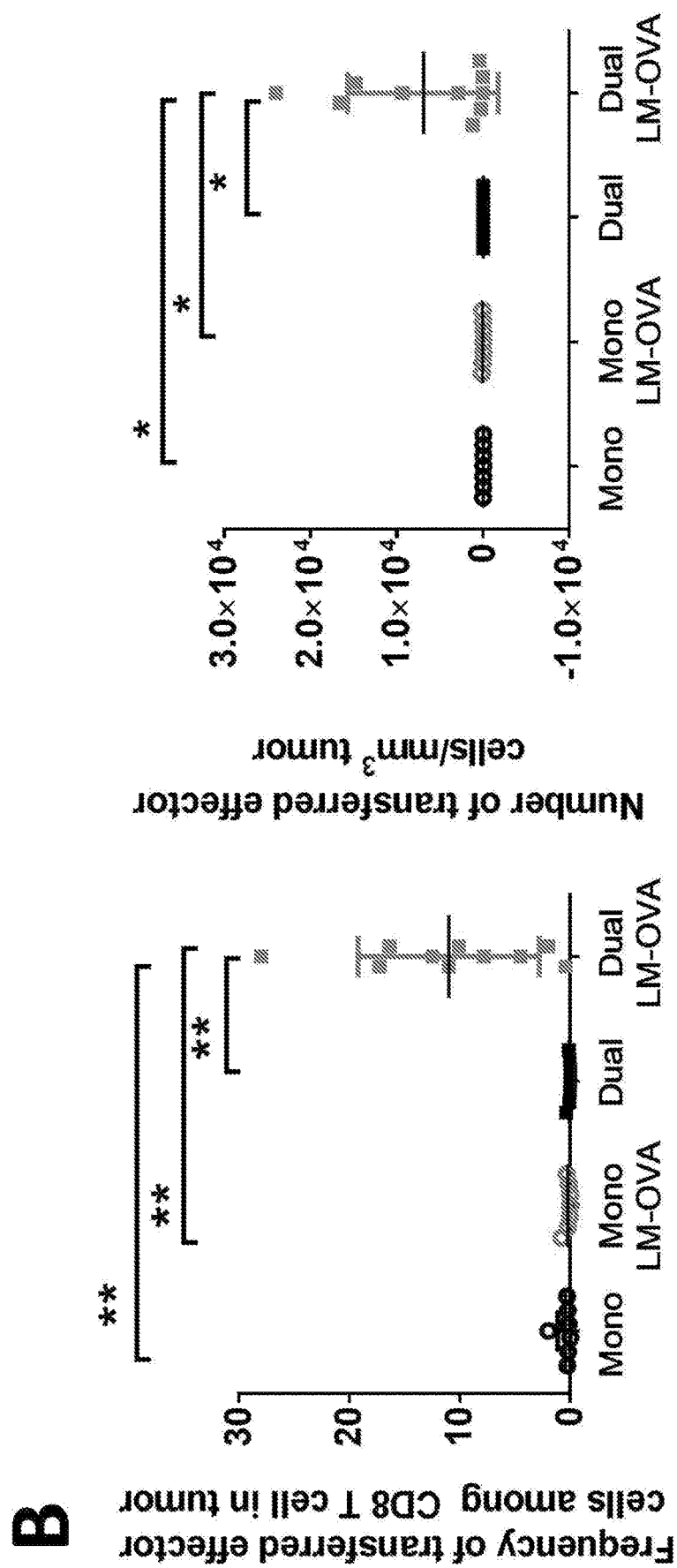
Figures 4A, 4B, 4C, 4D, 4E, 4F:
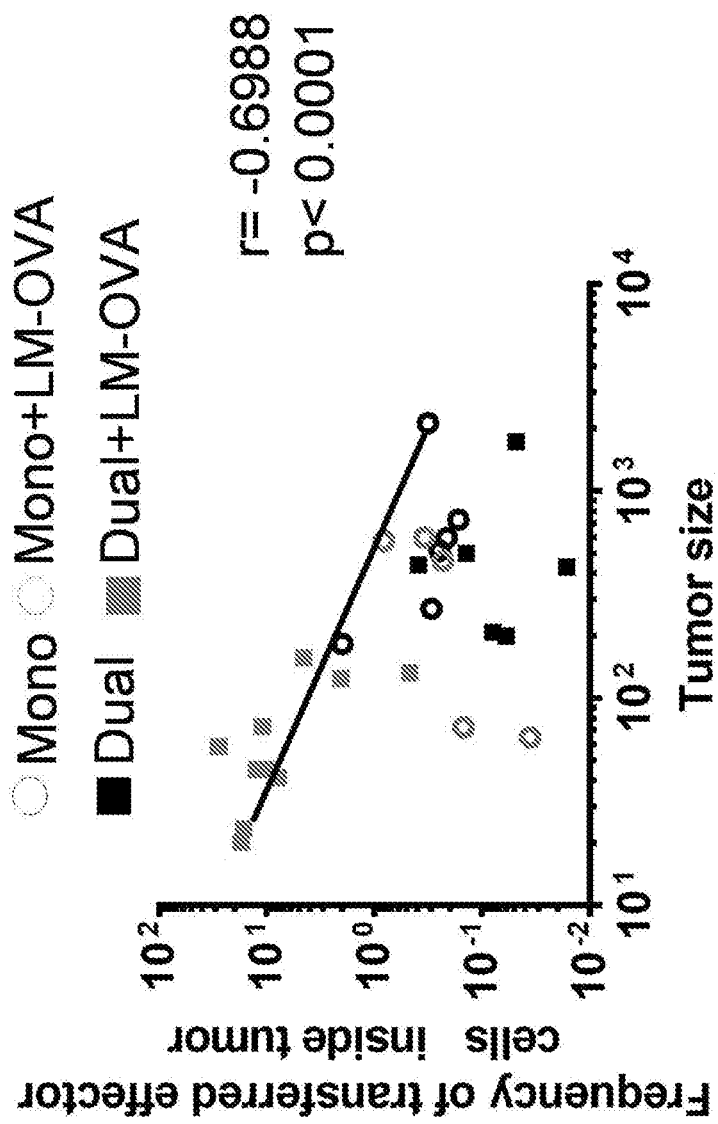
Figures 4A, 4B, 4C, 4D, 4E, 4F:
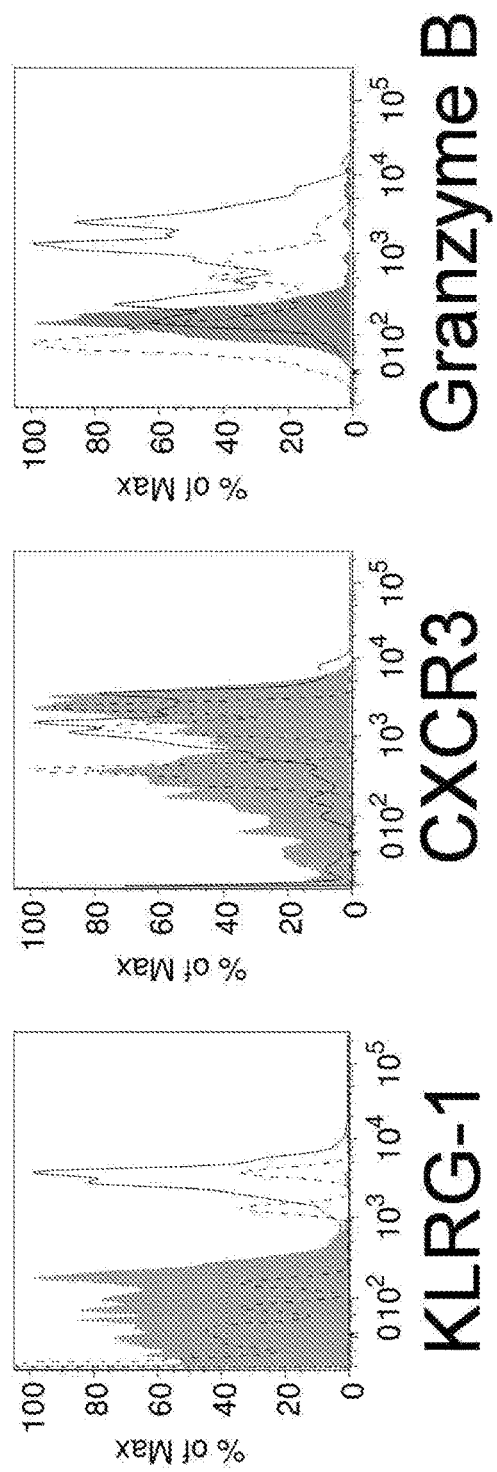
Figures 4A, 4B, 4C, 4D, 4E, 4F:
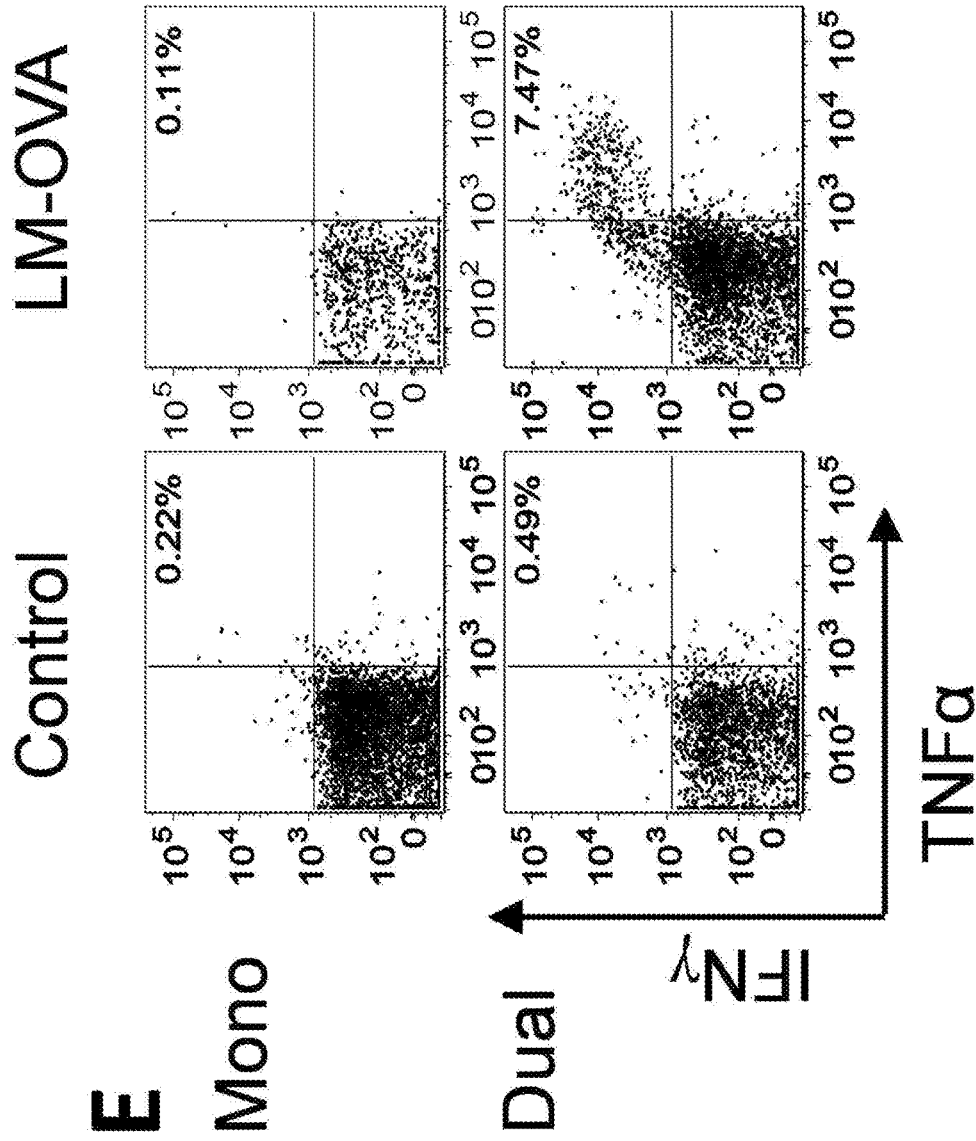
Figures 4A, 4B, 4C, 4D, 4E, 4F:
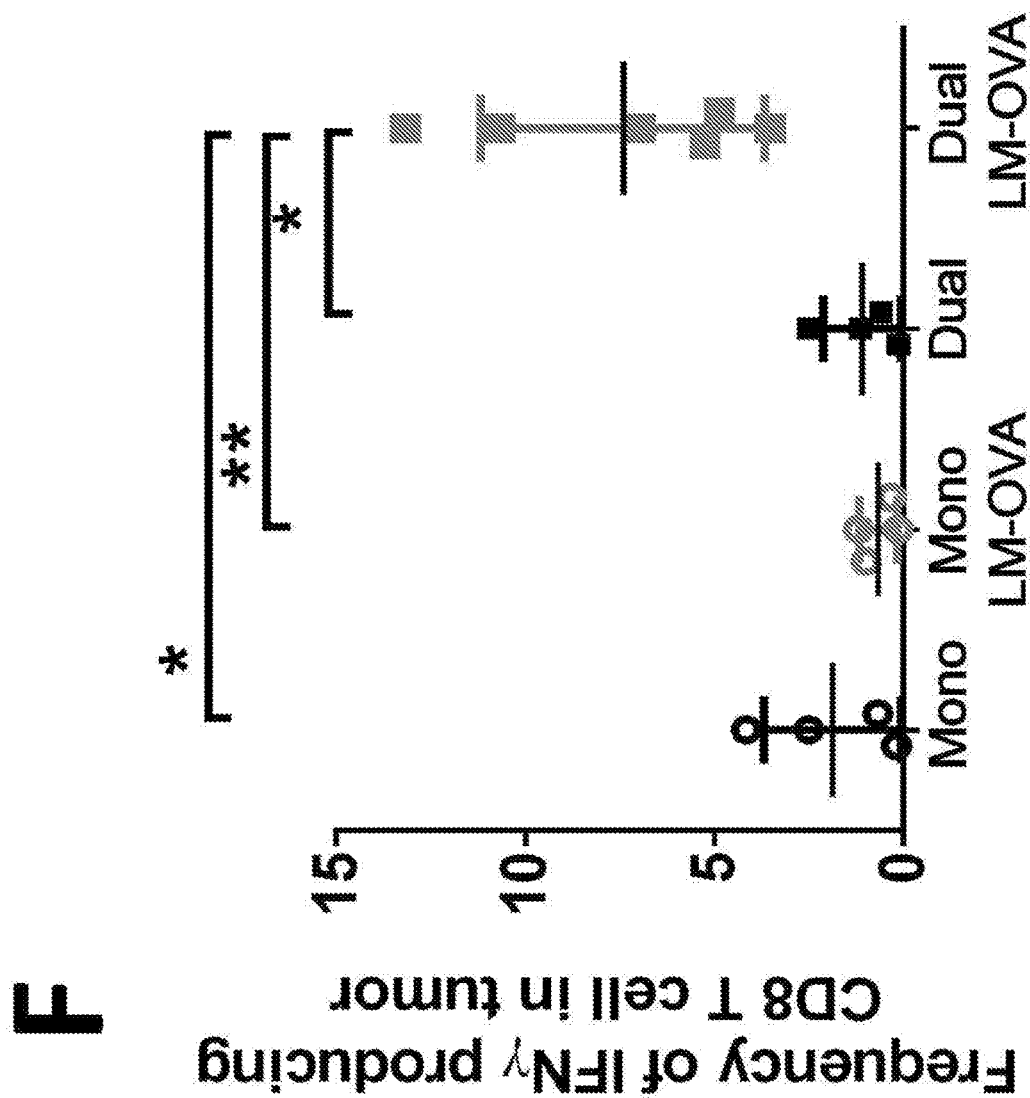
Figures 7A, 7B, 7C, 7D:
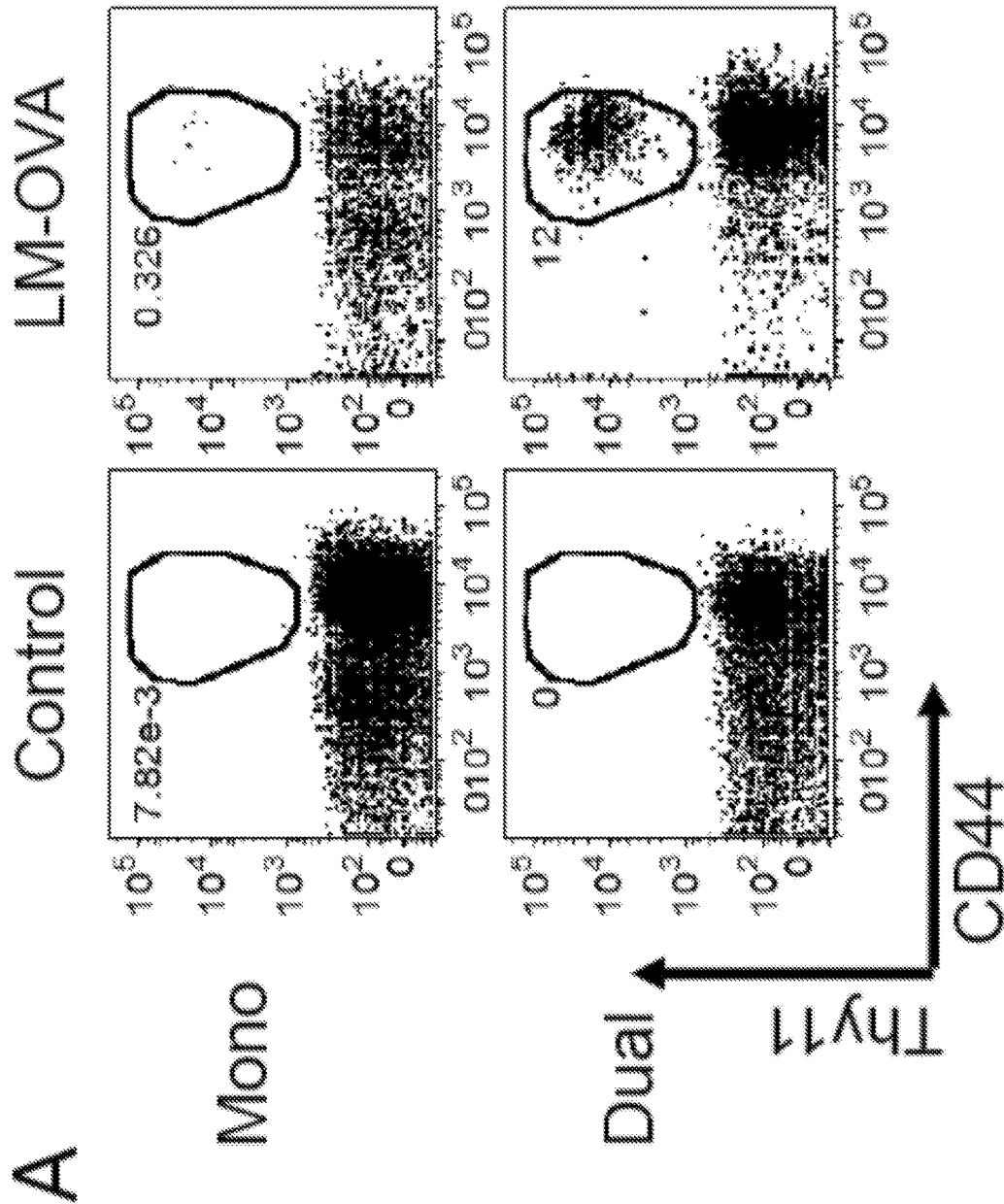
FIGS. 7A-7D show polyclonal ReACT increases tumor-specific CD8 T cell expansion and function. Four groups of B16-F10 tumor bearing mice received different treatment regimens including: polyclonal mono-specific CD8 T cell transfer (5×10$^5$/mouse) with or without LM-OVA infection and polyclonal dual-specific CD8 T cell transfer (5×10$^5$/mouse) with or without LM-OVA infection.
Figures 7A, 7B, 7C, 7D:
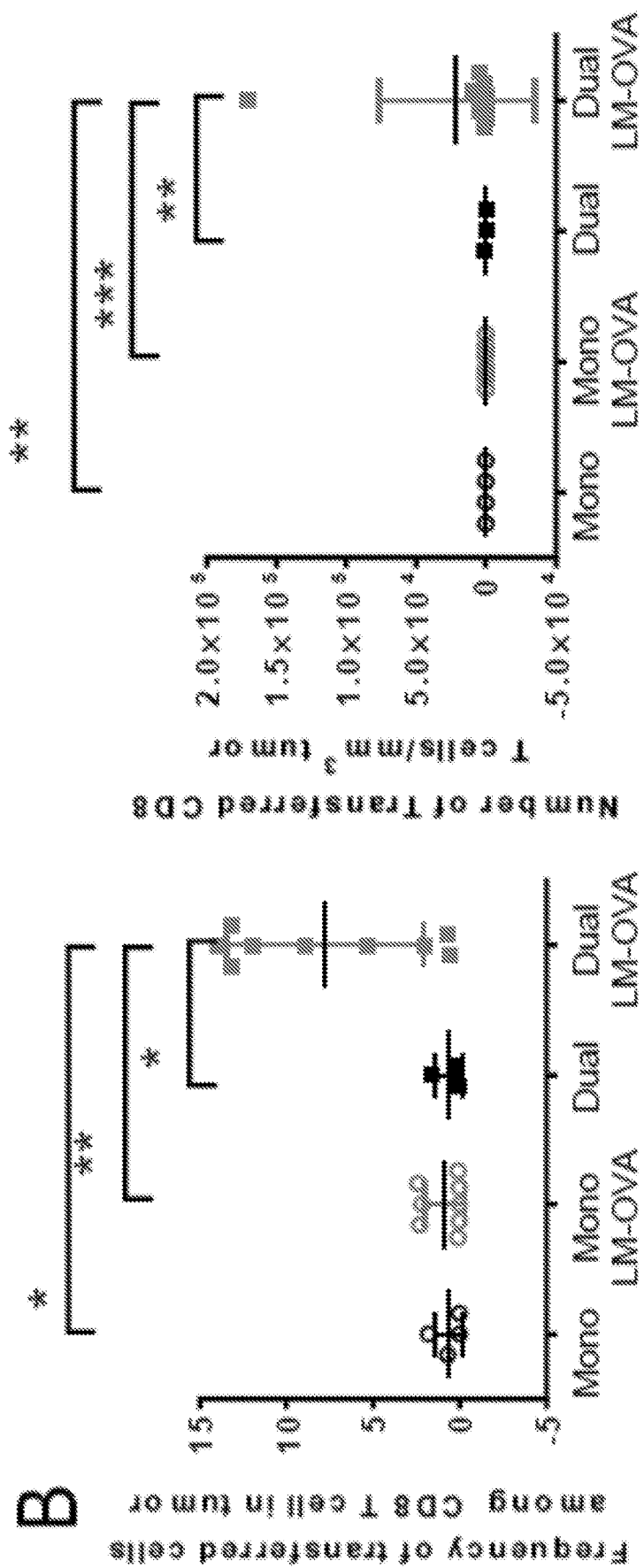
Figures 7A, 7B, 7C, 7D:
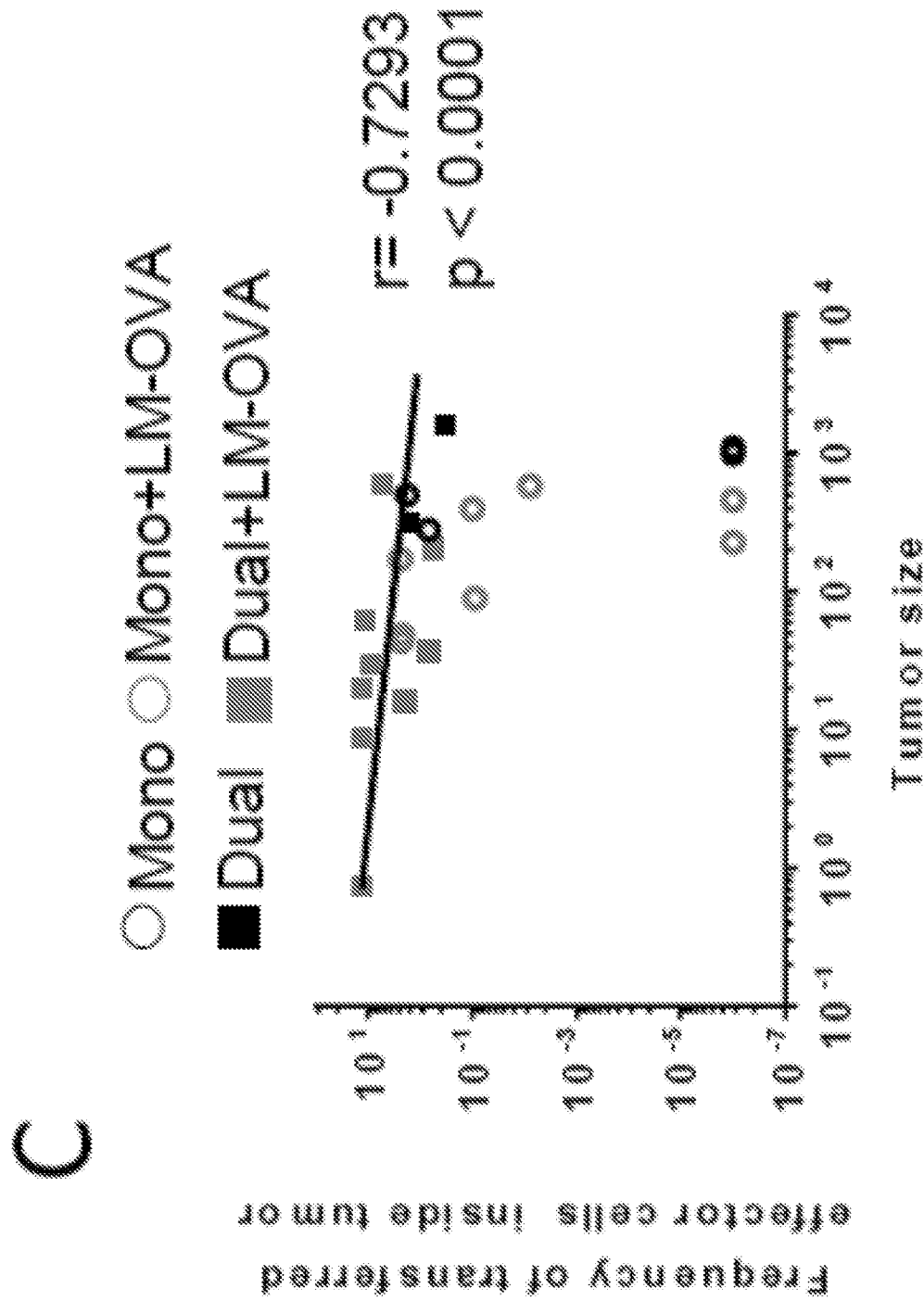
Figures 7A, 7B, 7C, 7D:
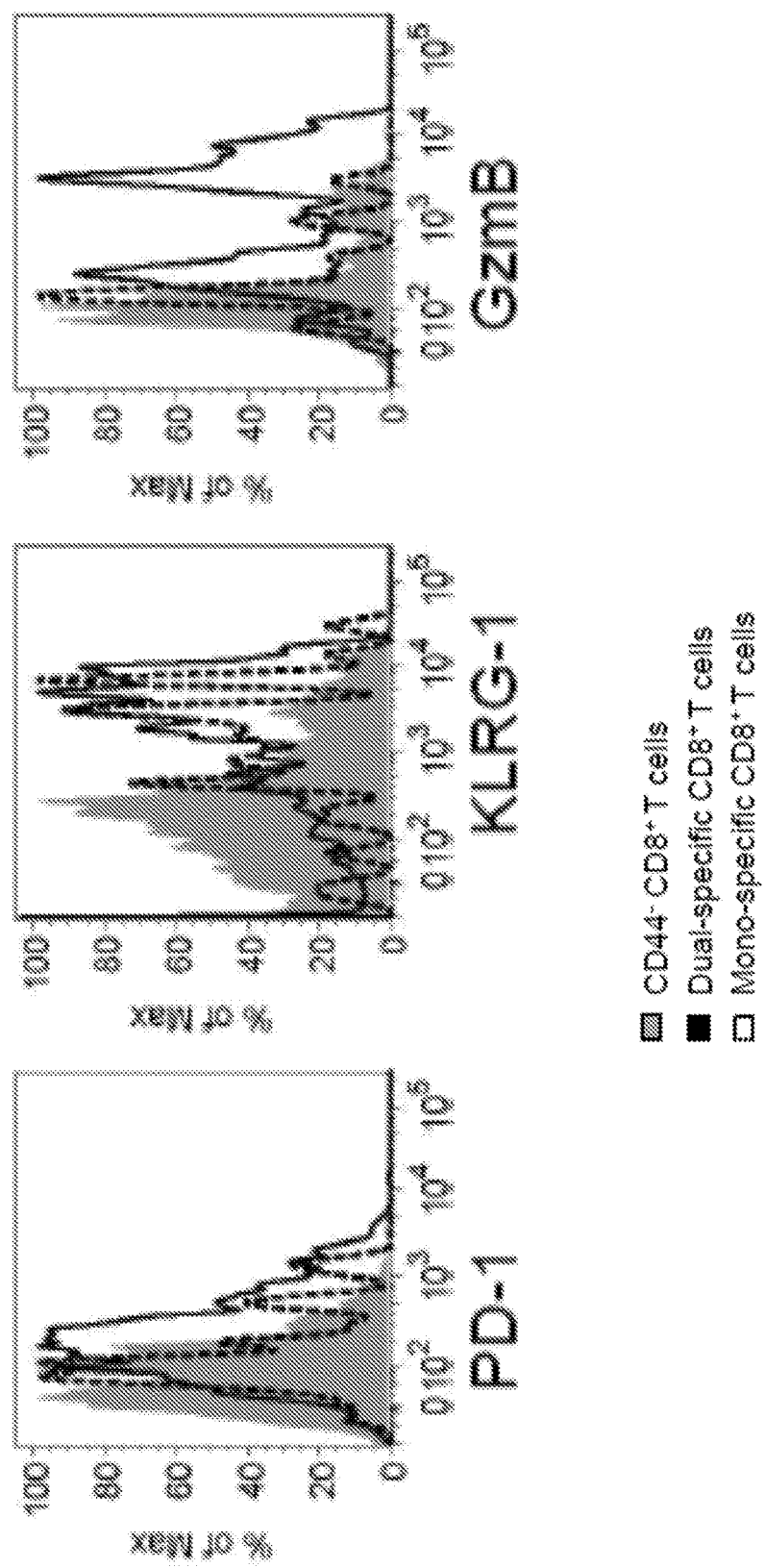

The remarkable antitumor effect of this combined strategy prompted us to study the tumor-specific CD8 T cell responses. Without preconditioning or additional adjuvants, very low frequencies and numbers of transferred CD8 T cells were detected in the tumors from mice that only received mono- or dual-specific CD8 T cell transfer alone, as reported previously (14) (FIGS. 4A-4B and FIGS. 7A-7B). This is not surprising given that the number of transferred cells was low and in vivo expansion following ACT was lacking. Interestingly, the intratumoral LM-OVA infection slightly increased the mono-specific CD8 T cell infiltrating tumors, which is likely in response to the chemotactic inflammation. More strikingly, a significant amount of transferred CD8 T cells were detected in tumors of mice that received bacterial infection combined with dual-specific CD8 T cell adoptive transfer (FIGS. 4A-4B and FIGS. 7A-7B). Importantly, frequencies of CD8 T cells recruited to tumors inversely correlated with tumor size in all treatment groups (FIG. 4C and FIG. 7C). Furthermore, the dual-specific CD8 T cells displayed an activated phenotype ($CD44^{hi}$, $KLRG-1^{hi}$ and granzyme $B^{hi}$) (FIG. 4D and FIG. 7D), accompanied by high expression of the chemokine receptor CXCR3, which has been shown to contribute to improved T cell migration to tumors (18). More strikingly, we observed a significant number of multi-potent CD8 T cells producing both IFNγ and TNFα in only mice receiving the combined treatment (FIGS. 3E-3F). Together, these results suggest that the dual-specific CD8 T cells in response to bacterial infection robustly expand, acquire effector function and migrate to the site of tumor, which in turn results in enhanced tumor control.

ReACT Reverses the Immunosuppressive TME and Recruits CD8 T Cells to the Tumor

Figures 5A, 5B, 5C, 5D, 5E, 5F, 5G, 5H, 5I, 5J:
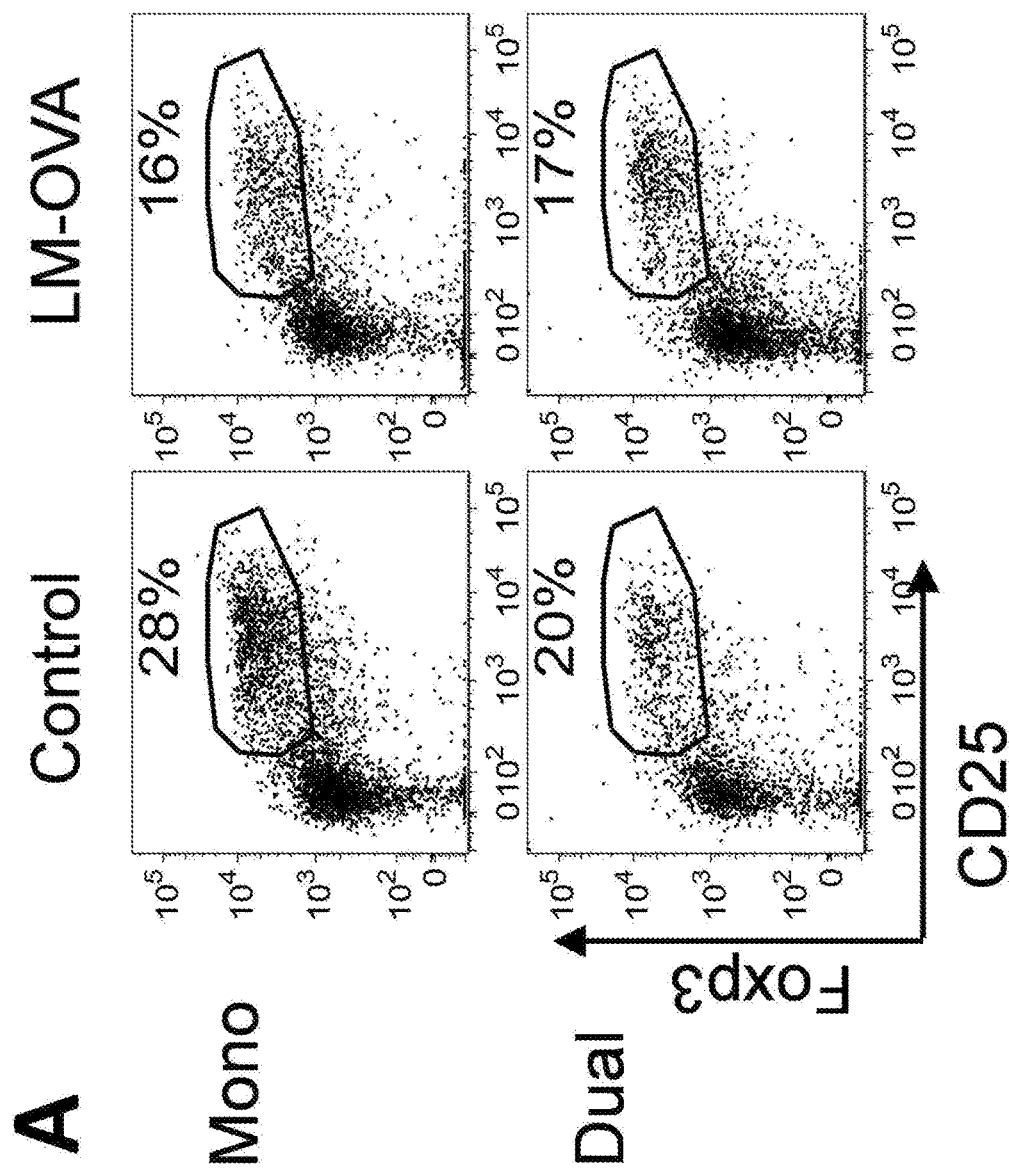
FIGS. 5A-5J show ReACT alters the tumor immunosuppressive microenvironment and tumor-specific CD8 T cell phenotypes.
Figures 5A, 5B, 5C, 5D, 5E, 5F, 5G, 5H, 5I, 5J:
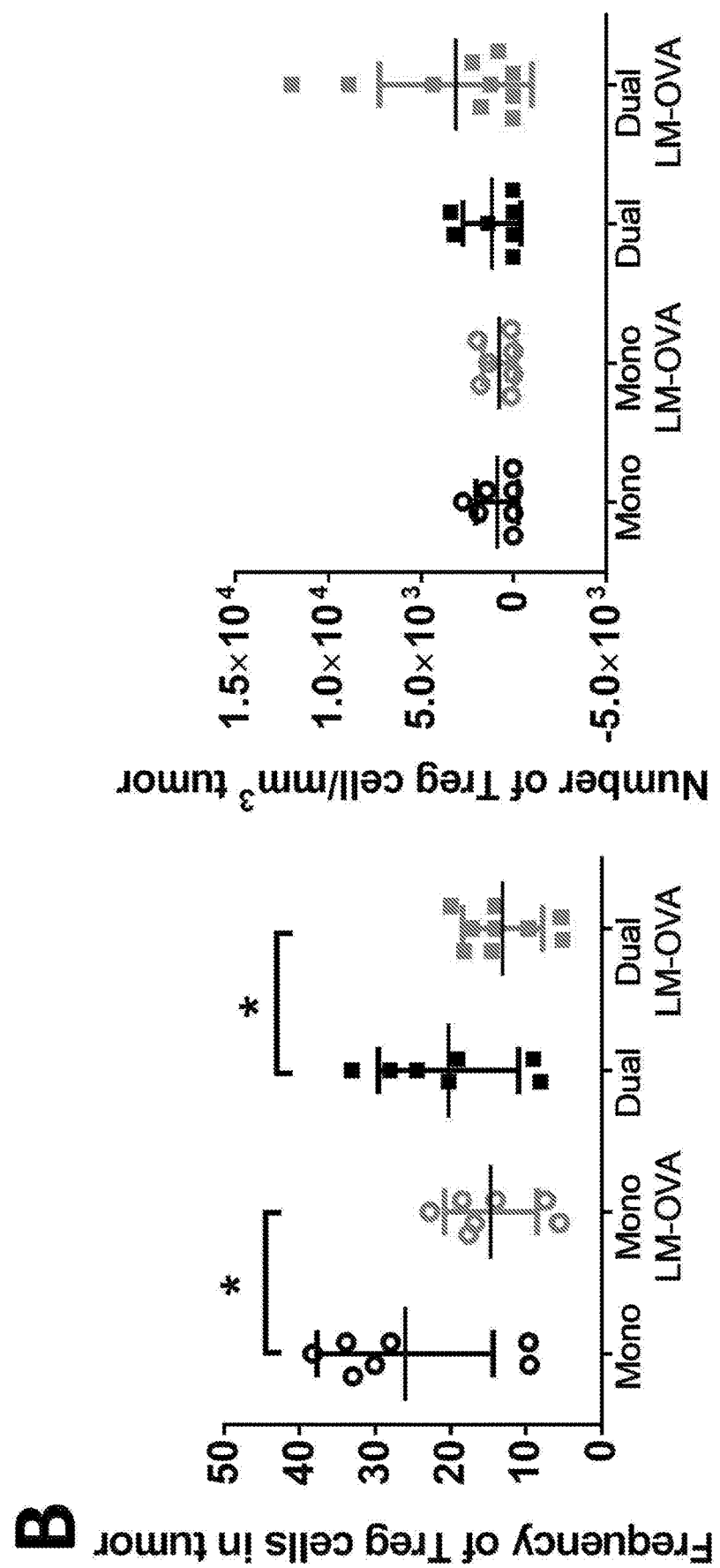
Figures 5A, 5B, 5C, 5D, 5E, 5F, 5G, 5H, 5I, 5J:
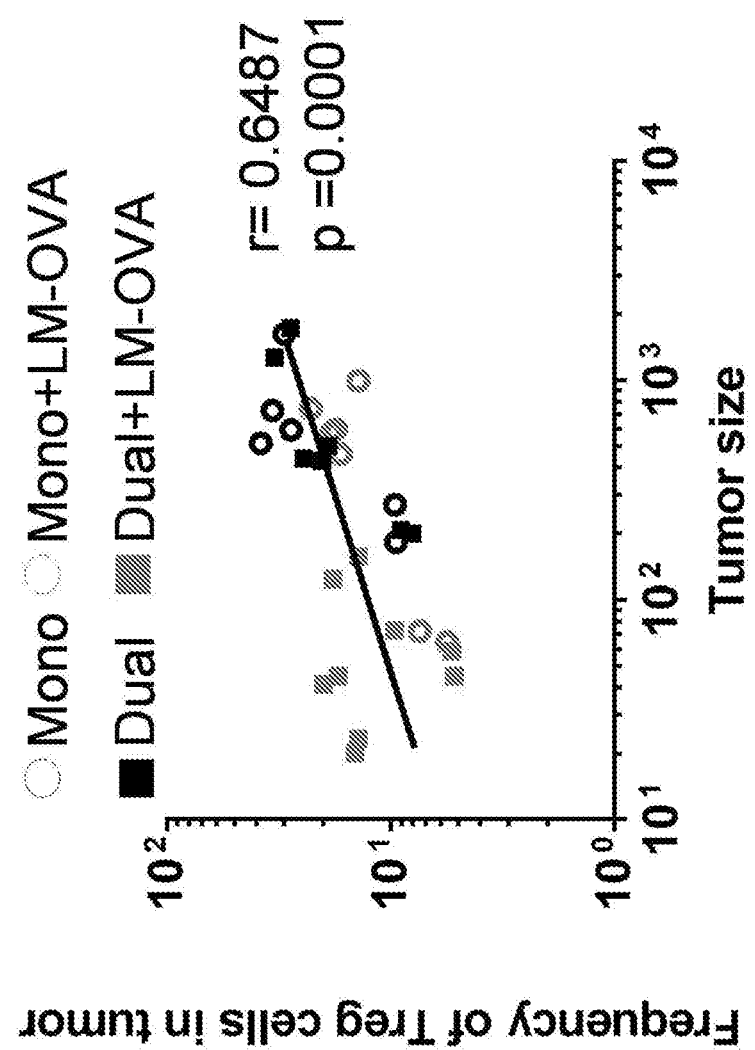
Figures 5A, 5B, 5C, 5D, 5E, 5F, 5G, 5H, 5I, 5J:
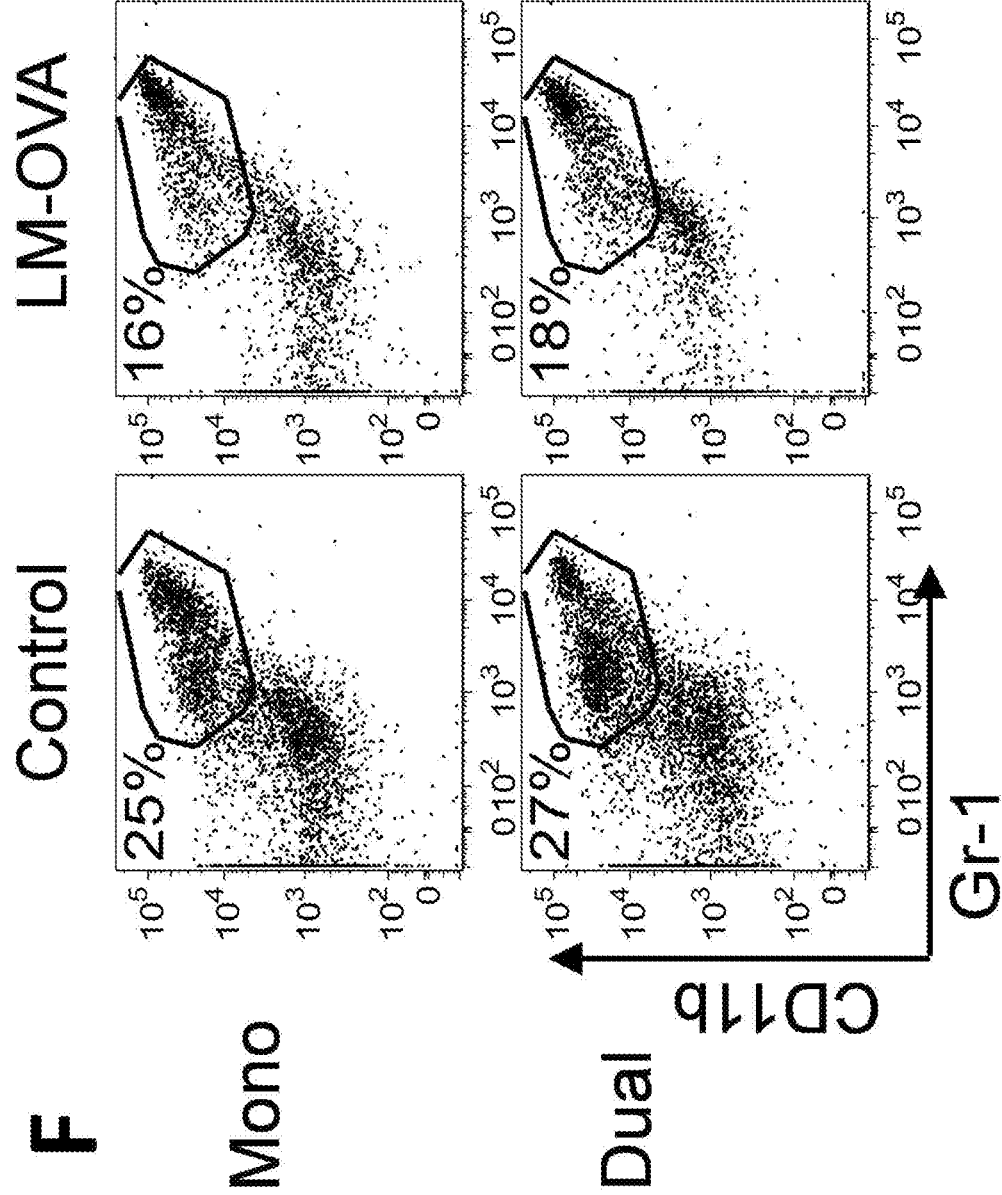
Figures 5A, 5B, 5C, 5D, 5E, 5F, 5G, 5H, 5I, 5J:
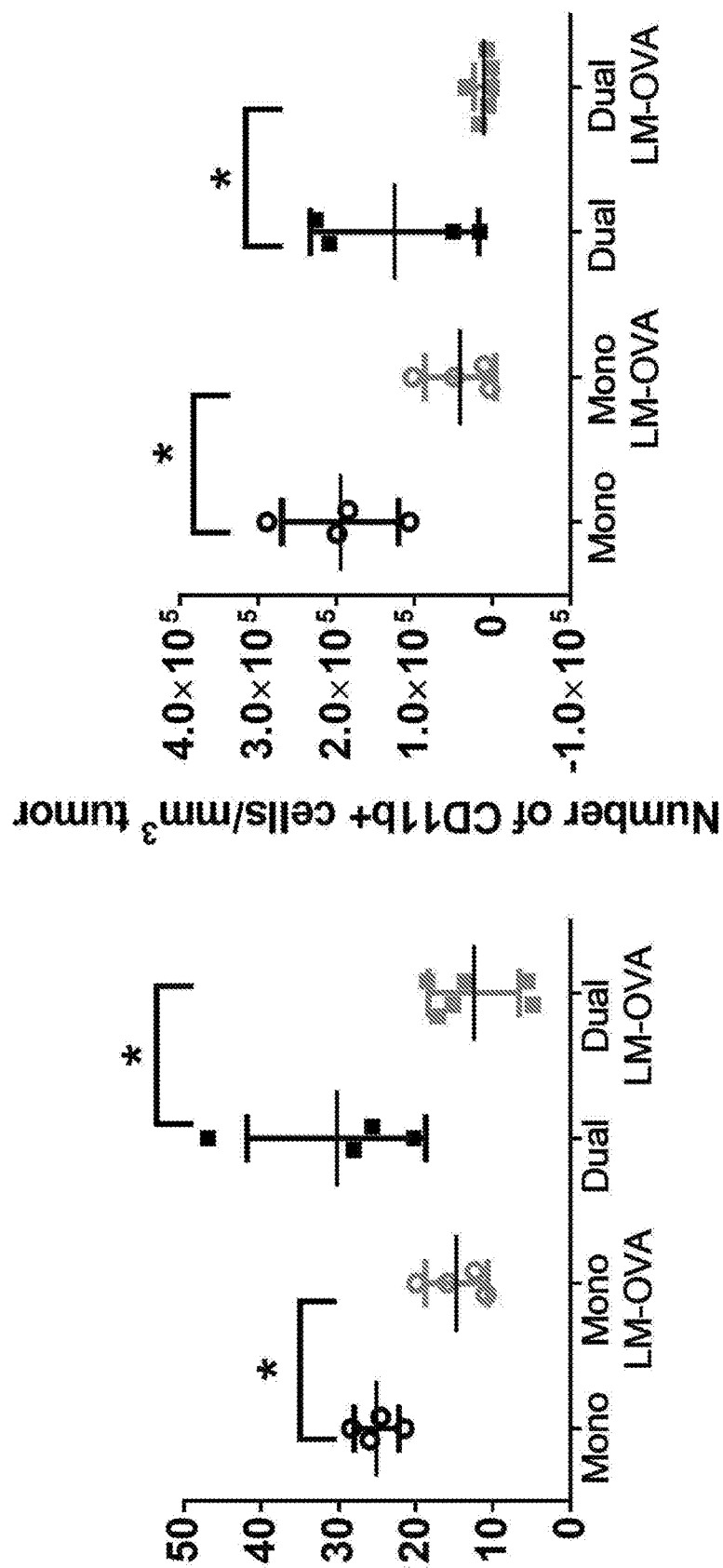
Figures 5A, 5B, 5C, 5D, 5E, 5F, 5G, 5H, 5I, 5J:
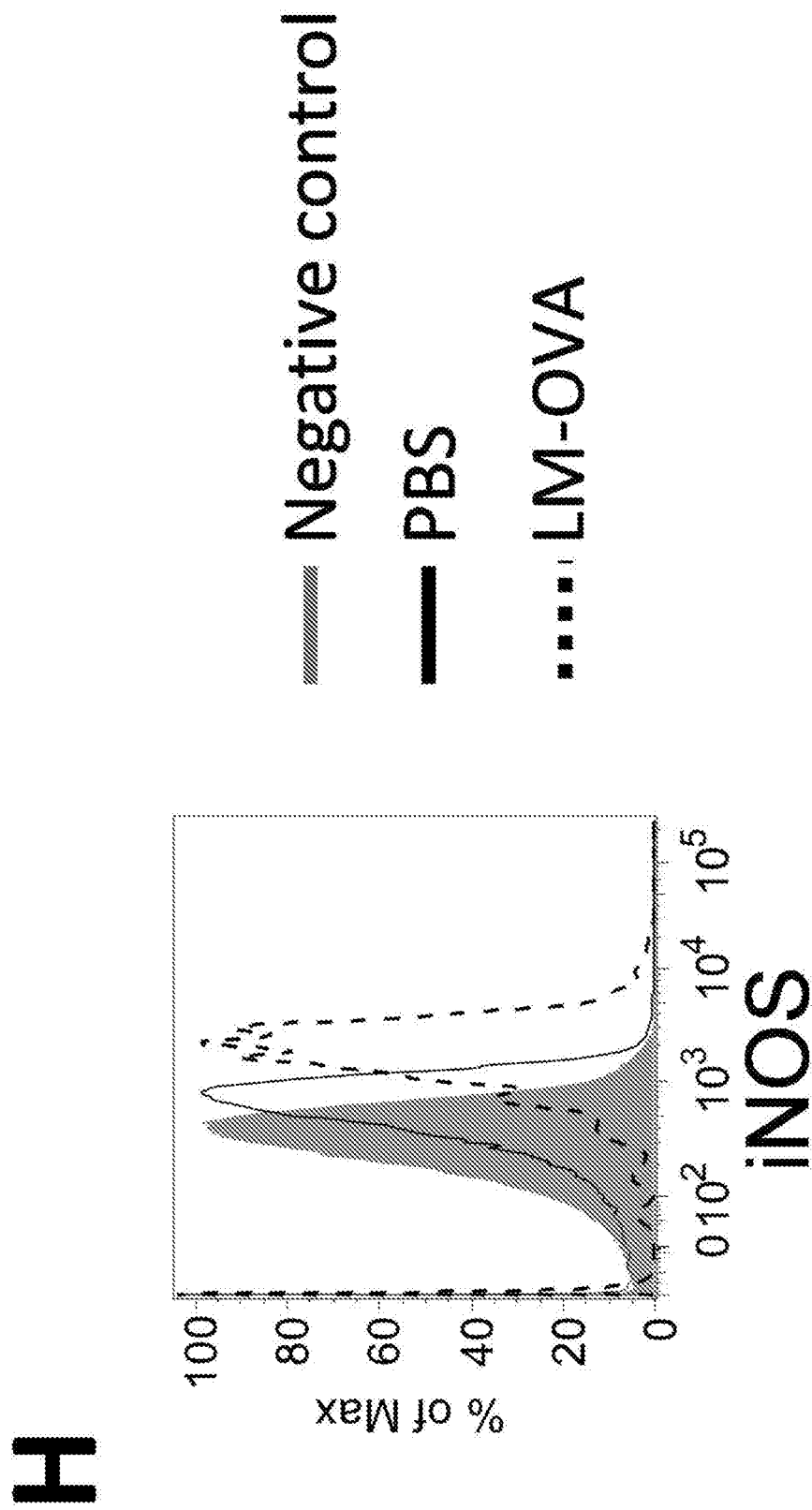
Figures 5A, 5B, 5C, 5D, 5E, 5F, 5G, 5H, 5I, 5J:
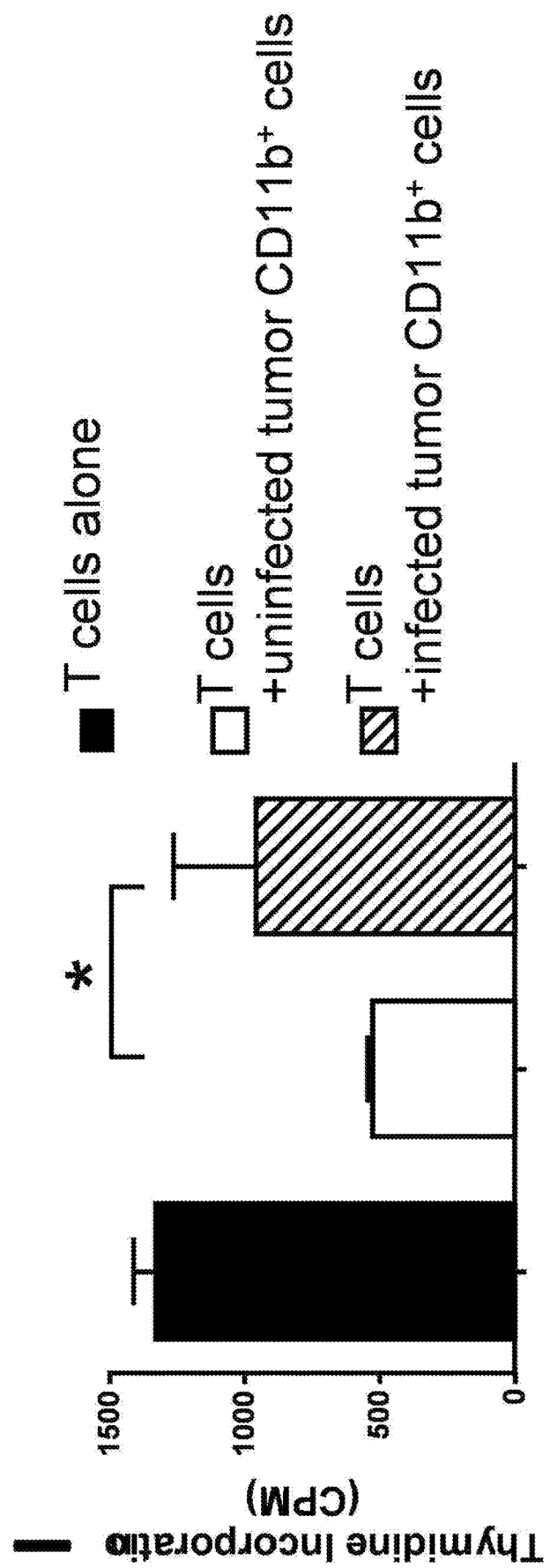
Figures 5A, 5B, 5C, 5D, 5E, 5F, 5G, 5H, 5I, 5J:
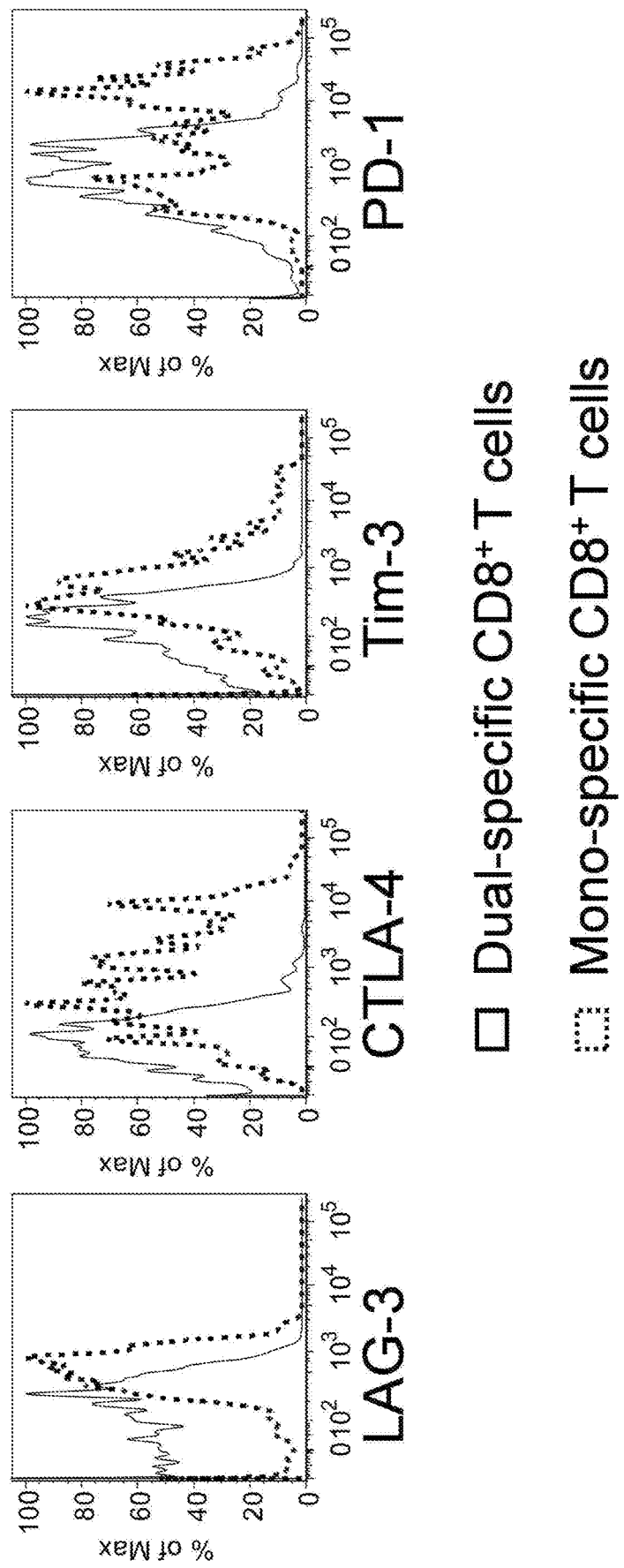
Figures 8A, 8B, 8C, 8D, 8E:
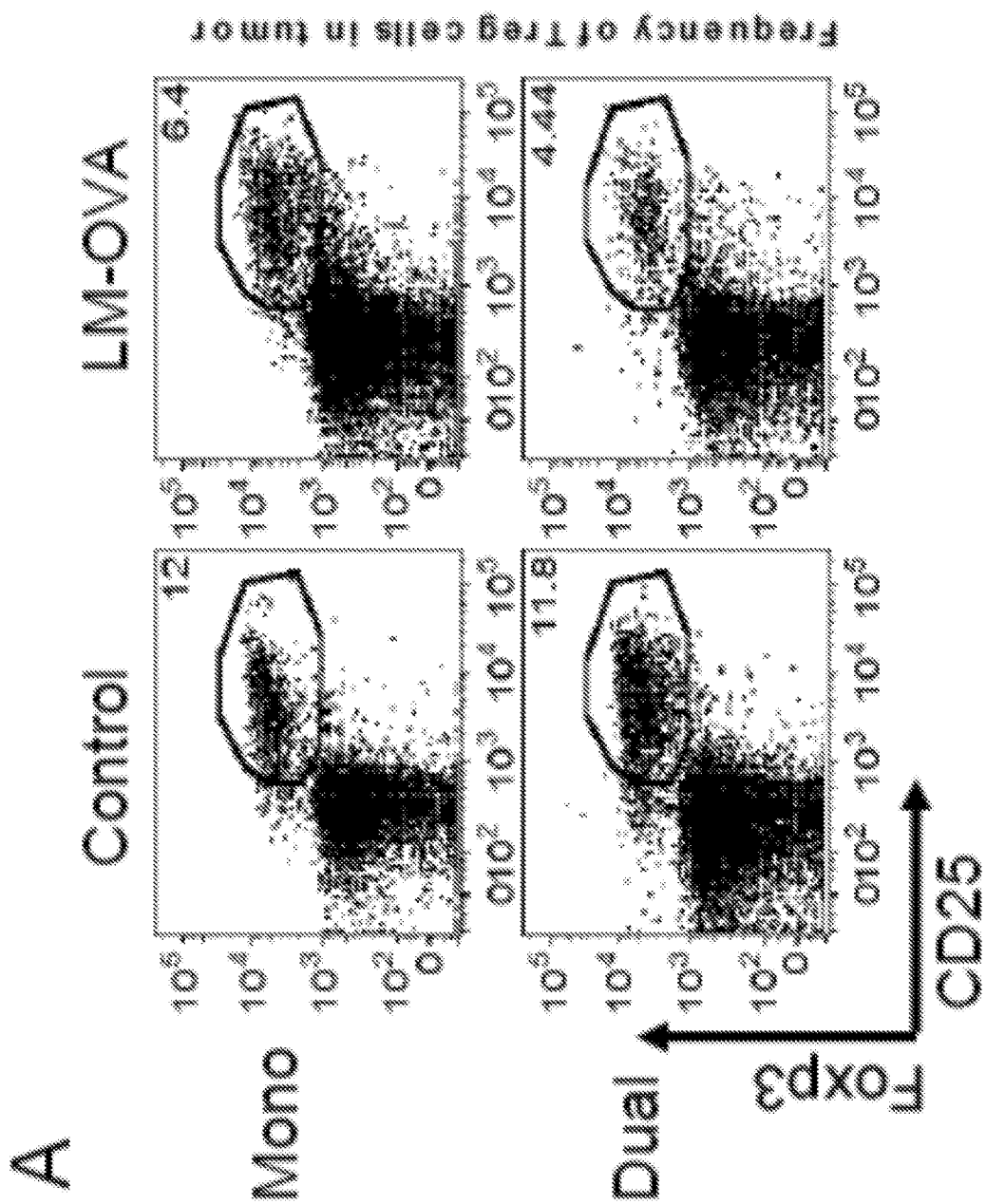
FIGS. 8A-8E show polyclonal ReACT reduces Treg cells and increases effector/Treg ratios in the tumors. Tumor bearing mice received various combinations of therapy as described in Supplemental FIG. 2.
Figures 8A, 8B, 8C, 8D, 8E:
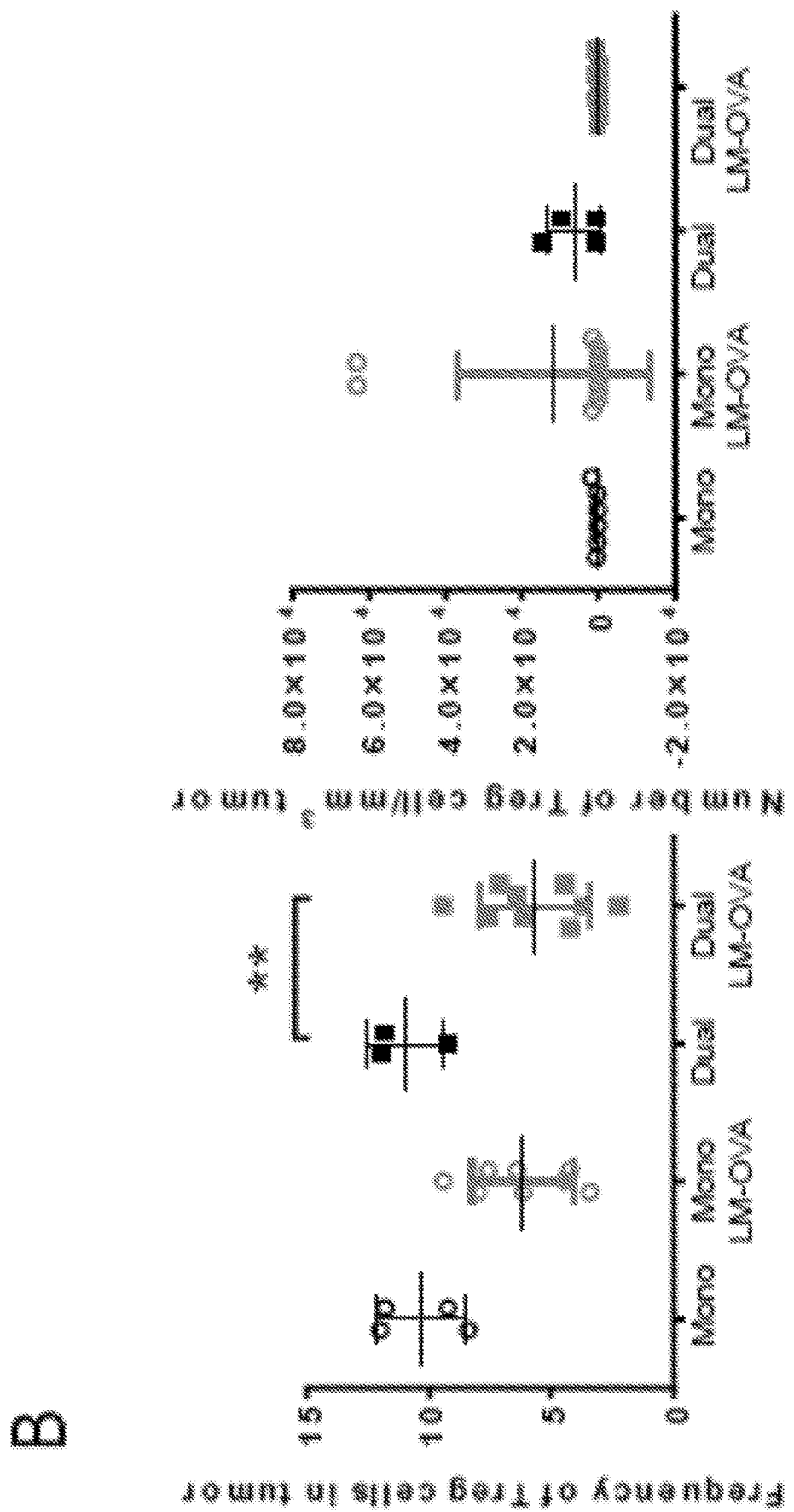
Figures 8A, 8B, 8C, 8D, 8E:
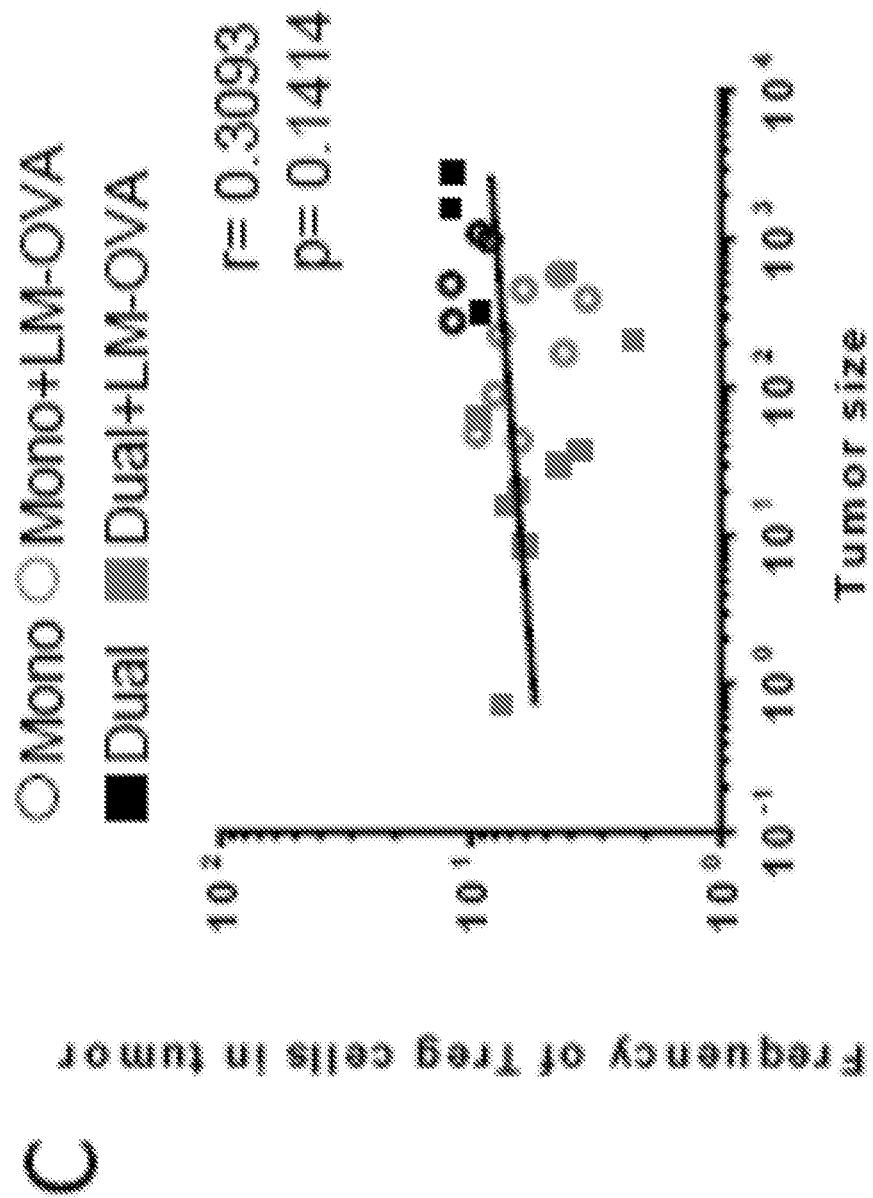
Figures 8A, 8B, 8C, 8D, 8E:
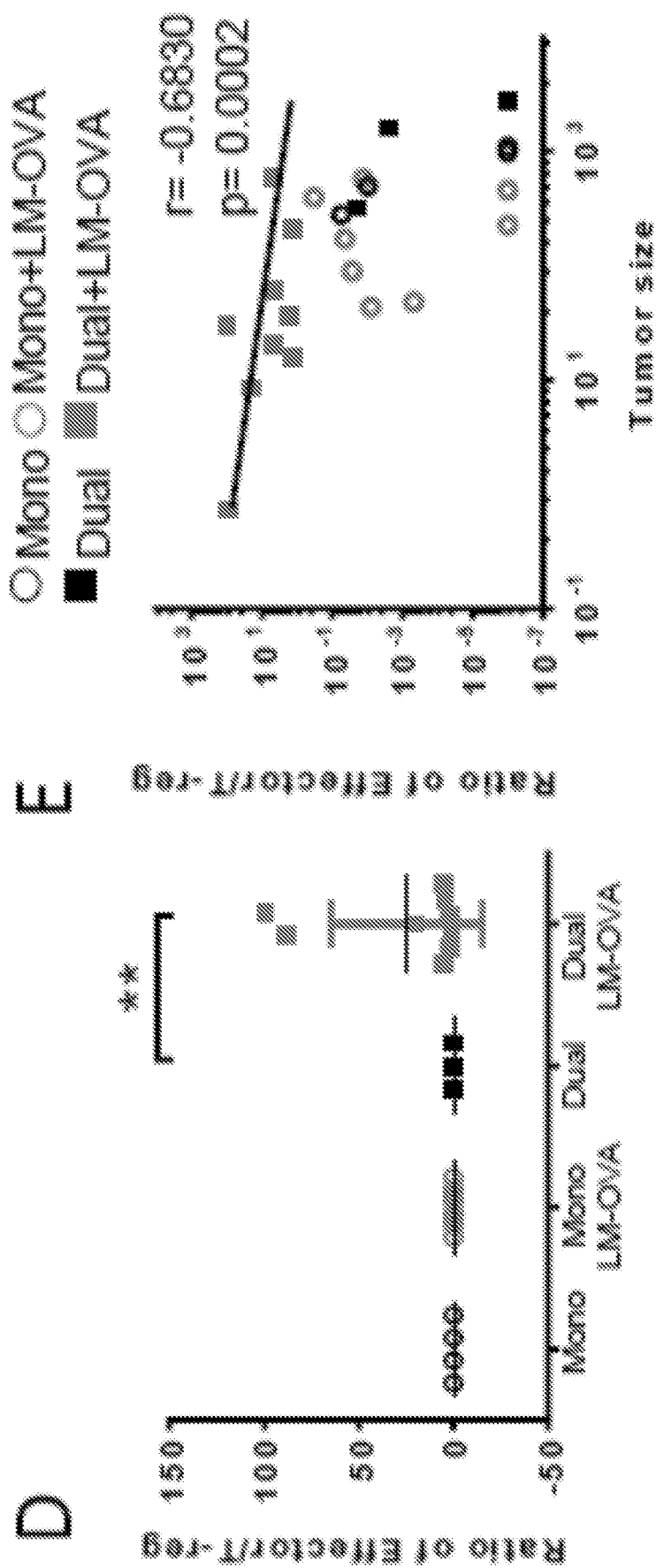

To assess whether our approach could alter the TME to synergistically improve the tumor-specific CD8 T cell response, we examined two major immunosuppressive cells inside the tumor, Tregs and myeloid derived suppressive cells (MDSCs). The intratumoral LM-OVA infection significantly reduced the frequency of $CD4^+$ $CD25^+$ $Foxp3^+$ Tregs regardless of the type of CD8 T cells transferred (mono- or dual-specific) (FIGS. 5A-5B and FIGS. 8A-8B). Notably, the frequency of Tregs in all treated mice positively correlated with tumor size (FIG. 5C and FIG. 8C). Interestingly, the effector/Treg ratio only increased in mice that received dual-specific CD8 T cells (FIG. 5D and FIG. 8D), owing to the robust expansion of effector cells as shown in FIGS. 5A-5B and FIGS. 7A-7B. Furthermore, the effector/Treg ratio inversely correlated with tumor size (FIG. 5E and FIG. 8E). Together, this shows that the ratio between effector CD8 T cells and Tregs is a critical factor that determines the final outcomes of different treatments.

Figures 9A, 9B:
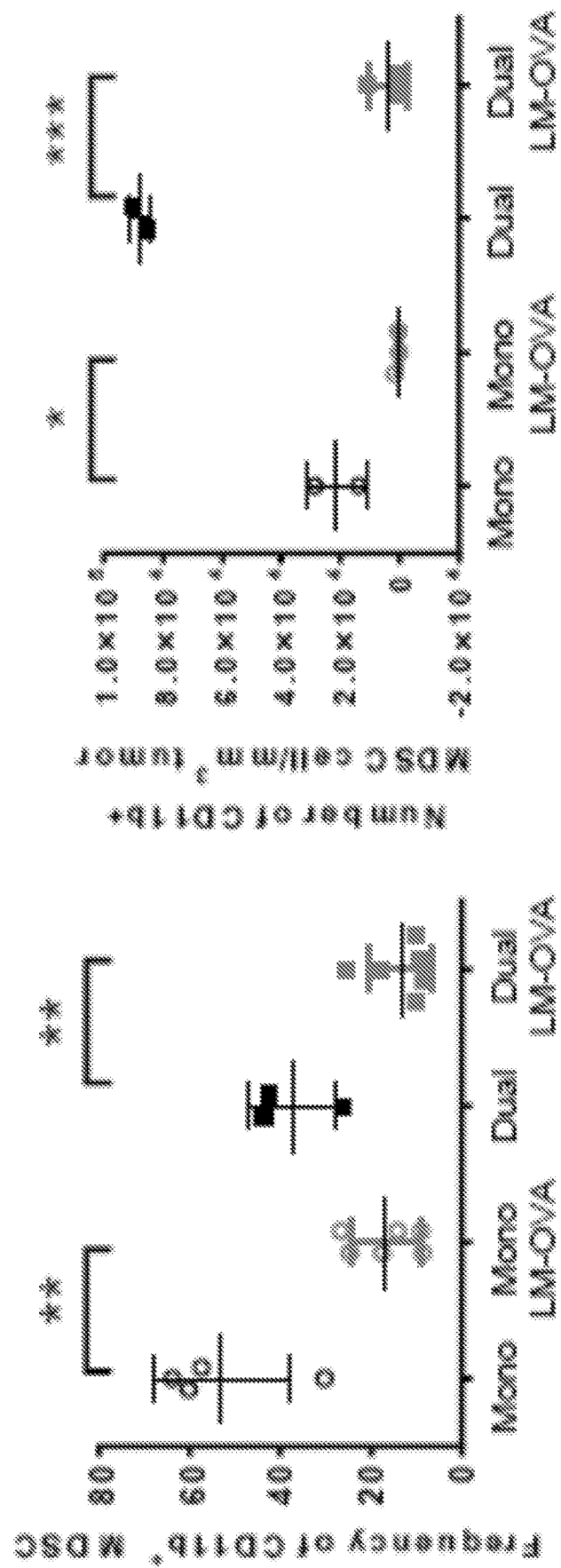
FIGS. 9A-9B show polyclonal ReACT reduces CD11b$_+$ cells in the tumors and alters their phenotype. Tumor bearing mice received various combinations of therapy as described in Supplemental FIG. 2.
Figures 9A, 9B:
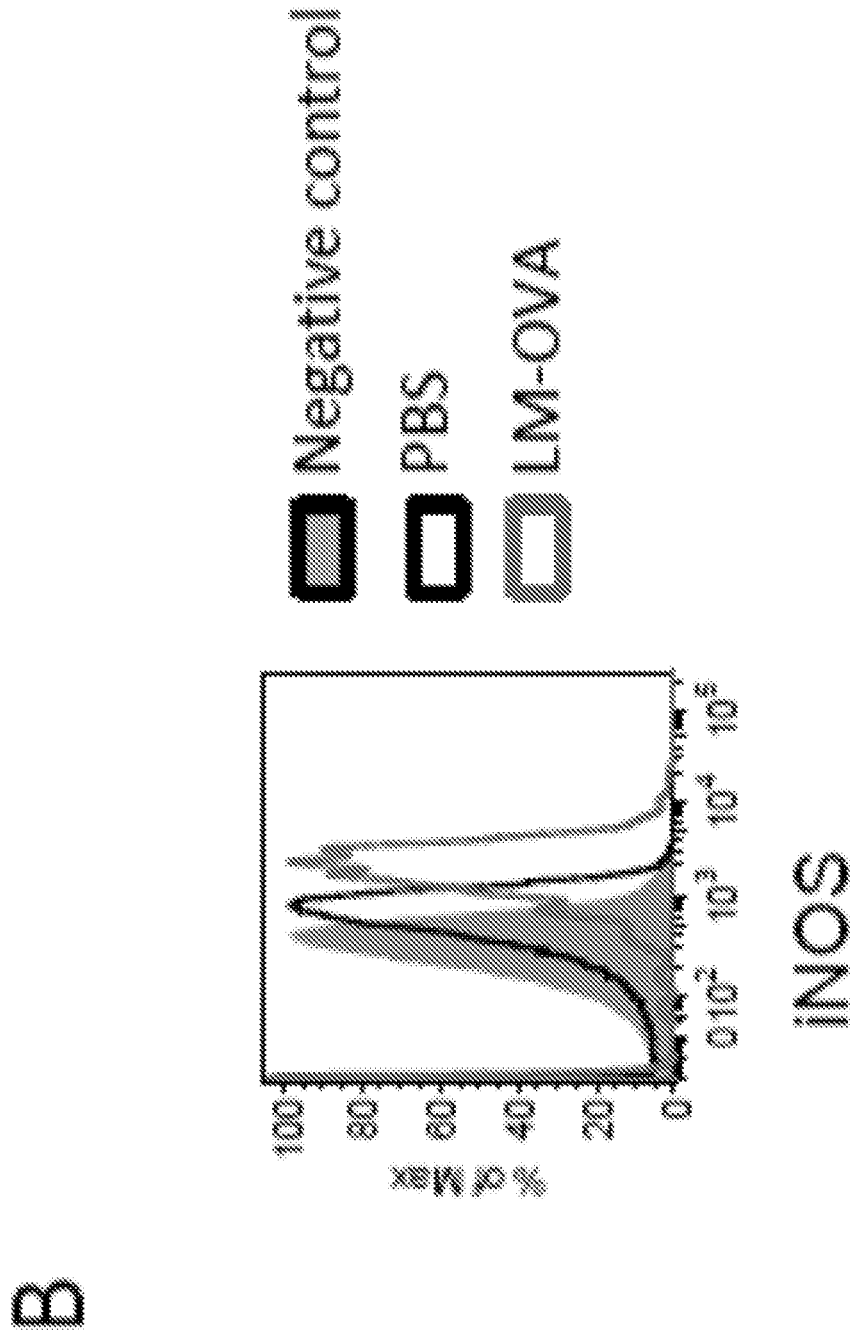

Another important type of suppressive cell, $CD11b^+Gr1^+$ MDSCs, were also significantly reduced by LM-OVA infection (FIGS. 5F-5G and FIG. 9A). This is consistent with previous findings that Listeria can directly infect MDSCs (19), which likely makes them susceptible to cytotoxic T cell mediated killing. Furthermore, Listeria infection can convert MDSCs into immune stimulatory cells (19,20). By the same token, we observed that the intratumoral Listeria infection caused elevated iNOS expression in $CD11b^+Gr1^+$ cells (FIG. 5F and FIG. 9B). To further test if this phenotypic change correlated with decreased immunosuppression, we isolated $CD11b^+$ cells from LM-OVA infected tumors and co-cultured them with in vitro activated CD8 T cells. Indeed, $CD11b^+$ cells from LM-OVA infected tumors were less suppressive to T cell proliferation than $CD11b^+$ cells from uninfected tumors (FIG. 5I), suggesting that Listeria infection diminishes the immunosuppressive function of myeloid cells and improves antitumor effector function of CD8 T cells.

More intriguingly, dual-specific CD8 T cells used in ReACT expressed lower levels of several inhibitory receptors (LAG-3, CTLA-4, Tim3 and PD-1) compared to mono-specific CD8 T cells (FIG. 5J), suggesting that these reenergized CD8 T cells might be bestowed with enhanced antitumor function and less exhausted phenotypes. These results collectively demonstrate that intratumoral bacterial infection can largely reverse the immunosuppression in the TME (9,19) and recruit dual-specific CD8 T cells with greater antitumor properties to the site of tumor.

Discussion

Both adoptive cell transfer of genetically engineered T cells and pathogen-based cancer vaccines are promising strategies to treat cancer. However, adoptively transferred T cells migrate inefficiently to the tumor and readily lose effector function in the immunosuppressive TME. Pathogen-based vaccines can reverse immunosuppression in the tumor, but are less efficient at inducing tumor-specific CD8 T cells with adequate magnitude and clonal types to confer tumor eradication. In this study, we combined the strength of both approaches and developed an innovative strategy, ReACT, to treat solid tumors in a preclinical model. ReACT uses a pathogen not only to break the immunosuppressive TME, but also to drive the expansion and migration of tumor-specific T cells to the site of tumor. We have demonstrated the enhanced antitumor efficacy of this combinatorial approach in comparison to either treatment alone in primary tumor eradication. More importantly, the mice cured from ReACT also develop immunological memory that protects them from subsequent rechallenge of the same tumor.

To bridge ACT and pathogen-based cancer vaccines together, the inventor genetically-engineered tumor-specific CD8 T cells with a second TCR that recognizes a pathogenic antigen to create dual-specific T cells. Several studies have shown that augmented expansion and durability of dual-specific CD8 T cells clearly increased the antitumor activity and the overall survival of tumor bearing mice. Nonetheless, tumors were not eradicated in these applications (12,21-23). This is possibly due to inefficient migration of dual-specific T cells to the tumor and unchanged immunosuppressive tumor microenvironment, given that the pathogen was either administrated systemically (23) or not used (12,21,22). In addition, one important distinction of dual-specific T cell generation in ReACT is to give a pathogen-specific TCR to tumor reactive T cells. This is opposite from previous work that gives pathogen (EBV, CMV and Influenza virus) reactive T cells a single tumor-specific TCR (21-23). Our approach allows us to generate polyclonal dual-specific T cells targeting multiple tumor associate antigens (TAAs) to increase the ability of tumor control.

William Coley was arguably the first to practice cancer immunotherapy a century ago. Live pathogens have been used as adjuvants (such as BCG) to stimulate patients' immune systems to treat bladder cancer and melanoma for decades (10,11). Pathogen-based immunotherapies induce potent innate immune responses that break the suppressive tumor microenvironment at least in part by targeting MDSCs and Tregs (9,19). However, with limited expansion of tumor-specific T cells both in quantity and clonal types, the antitumor effects of this approach are transient and rarely able to achieve long lasting antitumor effects (9). New strategies that use recombinant bacteria such as Listeria expressing tumor antigens to treat a variety of cancers have shown promising efficacy in clinical trials (9). In this study, we show greater antitumor effects when combining pathogen-based cancer vaccine with ACT of dual-specific CD8 T cells than recombinant Listeria expressing a tumor antigen. This can be explained by a greater magnitude of clonal expansion of adoptively transferred tumor-specific CD8 T cells than that from endogenous T cells, which supports the idea that the initial T cell mediated killing crucially depends on sufficiently high doses of T cells within the tumor for successful eradication (24).

In summary, we developed a novel immunotherapy, ReACT, to treat solid tumors and validated its efficacy in proof-of-principle animal experiments. Given the broad use of both ACT and pathogen-based vaccines in cancer treatments, this combinatorial strategy holds great translational value in treating various malignancies in humans. Methods Tumor Cell Lines, Bacteria and Mice B16-F10, B16-OVA and E0771 were obtained from ATCC and cultured in high-glucose DMEM (Cellgro) supplemented with 10% FBS. C57BL/6 mice were obtained through the National Cancer Institute (NCI) grantees program (Frederick, Md.). Pmel-1 TCR transgenic mice that recognize the MHC class I ($H-2D^b$)-restricted epitope of gp100 presented on the surface of B16-F10 melanoma were purchased from Jackson Laboratories (Bar Harbor, Mass.). Recombinant Listeria monocytogenes (LM) expressing OVA (LM-OVA) and GP33 (LM-GP33) was developed by Dr. Hao Shen (University of Pennsylvania School of Medicine, Philadelphia, Pa.) and kindly provided by Dr. Susan Kaech (Yale University, New Haven, Conn.)

Tumor Induction and Rechallenge

Melanoma tumors were established by injecting $2 \times 10^5$ B16-F10 cells subcutaneously (s.c.) on one flank of the C57BL/6 mice, while breast tumors established by injecting at $3 \times 10^5$ cells near the fat pad of the fourth mammary gland in the lower abdomen. Mice that eradicated their primary B16-F10 tumors were rechallenged with $1 \times 10^5$ B16-F10 cells on the one flank and $1 \times 10^5$ E0771 cells on the fat pad of the fourth mammary gland from the opposite flank. The eradication of primary tumor was assessed by no visible and palpable tumor mass at least 6-8 weeks after the clearance of tumors following initial treatment. Age- and gender-matched naïve C57BL/6 mice were used as controls. Tumor growth was monitored by measuring with calipers every other day and tumor volume was calculated as length×(width)$^2$/2

Retroviral Transductions to Generate Dual-Specific Tumor Reactive T Cells and Adoptive T Cells Transfer To produce retroviral supernatant to express OT-I ovalbumin-specific TCR in T cells, 293T cells were transfected with either MSCV-IRES-GFP (MIG) plasmid, or MIG-OT-I vector along with the pcLEco ecotropic packaging plasmid. At the same time, the splenocytes were harvested from Pmel-1 mice and seeded in 24 well plates at $5 \times 10^6$ cells/well and cultured with 10 nM gp100 (Genscript) and 10 ng/ml IL-2 (Peprotech) for 24 hours, followed by spinning transduction with prepared retroviral supernatant. After the transduction, these cells were cultured in the original medium for another 2 days and washed with PBS. After additional 3 days of culturing in T cell media containing 10 ng/ml IL-7 and 10 ng/ml IL-15, the positively transduced cells, defined by expression green fluorescence protein (GFP), were sorted for transfer.

For experiments involving ACT, mice received $5 \times 10^5$ sorted Pmel-1$^+$ mono-specific or OT-I$^+$ Pmel-1$^+$ dual-specific CD8 T cells at least seven days after initial tumor inoculation. At the same time, these mice were injected with either $1 \times 10^4$ colony forming unit (CFU) LM-OVA or PBS i.t.

Generation of polyclonal tumor reactive CD8 T cells

Bone marrow cells were isolated from C57BL/6 mice and cultured in 10% FCS RPMI medium with 200 ng/ml Flt3L for one week. On day 7, DCs were harvested and incubated with freeze-thawed tumor lysates at a ratio of one tumor cell equivalent to one DC (i.e., 1:1) as previously described (17). After 18 hours of incubation, DCs were harvested and maturated with LPS for 4 hours. The mature DCs and purified CD8 T cells were mixed in 1:2 ratio and cultured together with low dose IL-2 (1 ng/ml) for 24 hours. Then the activated CD8 T cells were transduced and sub-cultured as described above.

Immune Cell Isolation from Solid Tumors

The dissected tumor tissues were cut into small pieces and digested with 0.7 mg/ml collagenase XI (Sigma-Aldrich) and 30 mg/ml of type IV bovine pancreatic DNase (Sigma-Aldrich) for 45 min at 37° C. The immune cells were isolated by centrifugation with Lymphocyte Cell Separation Medium (Cedarlane Labs).

MDSC Suppression Assay

As described before (25), splenic CD8 T cells were isolated using the Mouse T Cell Isolation Kit (Stem Cell Technology), seeded in 96 well plates at $2 \times 10^5$ cells/well, and stimulated with anti-CD3 (eBioscience) and anti-CD28 (eBioscience) antibodies. At the same time, the CD11b$^+$ myeloid cells were sorted from tumors by Fluorescence Activated Cell Sorting (FACS) and added to these wells at various ratios (1:16, 1:8, 1:4 and 1:2). After 48 hours incubation, $^3$H-Thymidine (1 μCr/well) was added and the incubated for 16 hours. Cells were harvested using a Packard Filtermate Harvester 96 and counted by Microbeta counter (PerkinElmer, Beaconsfield, UK).

Statistical Analysis

Graphs were generated and statistical analyses performed using GraphPad Prism version 5.02 (GraphPad Software, Inc.). The overall tumor growth in FIG. 1C was analyzed by one-way ANOVA, while the comparison of tumor free mice after secondary challenge was determined by Log-rand test. The Kruskal-Wallis with Dunn's multiple comparison test was use to compare the individual tumor growth curves from different treatment groups. The Spearman's rank correlation coefficient test was used to determine the association between the tumor sizes and cell composition in mice received different treatments. For all other comparisons, t-tests were used to determine the statistical significance. *$p<0.05$; **$p<0.01$.

REFERENCES

1. Grupp S A, Kalos M, Barrett D, Aplenc R, Porter D L, Rheingold S R, et al. Chimeric antigen receptor-modi- 1. fied T cells for acute lymphoid leukemia. The New England journal of medicine 2013; 368(16): 1509-18.
2. Rosenberg S A, Restifo N P. Adoptive cell transfer as personalized immunotherapy for human cancer. Science 2015; 348(6230):62-8.
3. Sadelain M, Brentjens R, Riviere I. The basic principles of chimeric antigen receptor design. Cancer Discov 2013; 3(4):388-98.
4. Turtle C J, Hudecek M, Jensen M C, Riddell S R. Engineered T cells for anti-cancer therapy. Curr Opin Immunol 2012; 24(5):633-9.
5. Gajewski T F, Fuertes M, Spaapen R, Zheng Y, Kline J. Molecular profiling to identify relevant immune resistance mechanisms in the tumor microenvironment. Curr Opin Immunol 2011; 23 (2):286-92.
6. Restifo N P, Dudley M E, Rosenberg S A. Adoptive immunotherapy for cancer: harnessing the T cell response. Nature reviews Immunology 2012; 12(4): 269-81.
7. Joyce J A, Fearon D T. T cell exclusion, immune privilege, and the tumor microenvironment. Science 2015; 348(6230): 74-80.
8. Gajewski T F, Schreiber H, Fu Y X. Innate and adaptive immune cells in the tumor microenvironment. Nature immunology 2013; 14(10):1014-22.
9. Wood L M, Paterson Y. Attenuated *Listeria monocytogenes*: a powerful and versatile vector for the future of tumor immunotherapy. Front Cell Infect Microbiol 2014; 4:51.
10. Redelman-Sidi G, Glickman M S, Bochner B H. The mechanism of action of BCG therapy for bladder cancer—a current perspective. Nature reviews Urology 2014; 11(3):153-62.
11. Garbe C, Eigentler T K, Keilholz U, Hauschild A, Kirkwood J M. Systematic review of medical treatment in melanoma: current status and future prospects. The oncologist 2011; 16(1):5-24.
12. Kershaw M H, Westwood J A, Hwu P. Dual-specific T cells combine proliferation and antitumor activity. Nat Biotechnol 2002; 20(12):1221-7.
13. Wang X, Riviere I. Manufacture of tumor- and virus-specific T lymphocytes for adoptive cell therapies. Cancer Gene Ther 2015; 22(2):85-94.
14. Overwijk W W, Theoret M R, Finkelstein S E, Surman D R, de Jong L A, Vyth-Dreese F A, et al. Tumor regression and autoimmunity after reversal of a functionally tolerant state of self-reactive CD8+ T cells. The Journal of experimental medicine 2003; 198(4):569-80.
15. Frassanito M A, Mayordomo J I, DeLeo R M, Storkus W J, Lotze M T, DeLeo A B. Identification of Meth A sarcoma-derived class I major histocompatibility complex-associated peptides recognized by a specific CD8+ cytotoxic T lymphocyte. Cancer research 1995; 55(1):124-8.
16. Stark F C, Sad S, Krishnan L. Intracellular bacterial vectors that induce CD8(+) T cells with similar cytolytic abilities but disparate memory phenotypes provide contrasting tumor protection. Cancer research 2009; 69(10):4327-34.
17. Liang X, Fu C, Cui W, Ober-Blobaum J L, Zahner S P, Shrikant P A, et al. beta-catenin mediates tumor-induced immunosuppression by inhibiting cross-priming of CD8(+) T cells. J Leukoc Biol 2014; 95(1):179-90.
18. Mikucki M E, Fisher D T, Matsuzaki J, Skitzki J J, Gaulin N B, Muhitch J B, et al. Non-redundant requirement for CXCR3 signalling during tumoricidal T-cell trafficking across tumour vascular checkpoints. Nat Commun 2015; 6:7458.
19. Chandra D, Jahangir A, Quispe-Tintaya W, Einstein M H, Gravekamp C. Myeloid-derived suppressor cells have a central role in attenuated *Listeria monocytogenes*-based immunotherapy against metastatic breast cancer in young and old mice. Br J Cancer 2013; 108(11):2281-90.
20. Gabrilovich D I, Ostrand-Rosenberg S, Bronte V. Coordinated regulation of myeloid cells by tumours. Nature reviews Immunology 2012; 12(4):253-68.
21. Heemskerk M H, Hoogeboom M, Hagedoorn R, Kester M G, Willemze R, Falkenburg J H. Reprogramming of virus-specific T cells into leukemia-reactive T cells using T cell receptor gene transfer. The Journal of experimental medicine 2004; 199(7):885-94.
22. Louis C U, Savoldo B, Dotti G, Pule M, Yvon E, Myers G D, et al. Antitumor activity and long-term fate of chimeric antigen receptor-positive T cells in patients with neuroblastoma. Blood 2011; 118(23):6050-6.
23. Murphy A, Westwood J A, Brown L E, Teng M W, Moeller M, Xu Y, et al. Antitumor activity of dual-specific T cells and influenza virus. Cancer Gene Ther 2007; 14(5):499-508.
24. McGray A J, Hallett R, Bernard D, Swift S L, Zhu Z, Teoderascu F, et al Immunotherapy-induced CD8+ T cells instigate immune suppression in the tumor. Mol Ther 2014; 22(1):206-18.
25. Haverkamp J M, Crist S A, Elzey B D, Cimen C, Ratliff T L. In vivo suppressive function of myeloid-derived suppressor cells is limited to the inflammatory site. Eur J Immunol 2011; 41(3):749-59.
26. Marcela V. Maus, Stephan A. Grupp, David L. Porter, Carl H. June. Antibody-modified T cells: CARs take the front seat for hematologic malignancies. Blood Apr. 2014, 123 (17) 2625-2635;
27. Vandana Kalia, Surojit Sarkar, Shruti Subramaniam, W. Nicholas Haining, Kendall A. Smith, Rafi Ahmed. Prolonged Interleukin-2Ra Expression on Virus-Specific C D8+ T Cells Favors Terminal-Effector Differentiation In Vivo Immunity, Volume 32, Issue 1, 29 Jan. 2010, Pages 91-103
28. Matthew E. Pipkinl, Jilian A. Sacks, Fernando Cruz-Guilloty 1, Mathias G. Lichtenheld, Michael J. Bevan, Anjana Rao. Interleukin-2 and Inflammation Induce Distinct Transcriptional Programs that Promote the Differentiation of Effector Cytolytic T Cells. Immunity, Volume 32, Issue 1, 29 Jan. 2010, Pages 79-90.
29. Maude, S. L., et al. Chimeric antigen receptor T cells for sustained remissions in leukemia. *The New England journal of medicine* 371, 1507-1517 (2014).
30. Ruth Ganss and Douglas Hanahan. Tumor Microenvironment Can Restrict the Effectiveness of Activated Antitumor Lymphocytes. Cancer Res Oct. 15, 1998 (58) (20) 4673-4681.
31. Ruth Ganss, Eduard Ryschich, Ernst Klar, Bernd Arnold and Gunter J. Hammerling. Combination of T-Cell Therapy and Trigger of Inflammation Induces Remodeling of the Vasculature and Tumor Eradication. Cancer Res Mar. 1, 2002 (62) (5) 1462-1470.
32. Natalio Garbi, Bernd Arnold, Siamon Gordon, Gunter J. Hammerling, and Ruth Ganss. CELLULAR IMMUNOLOGY AND IMMUNE REGULATION: CpG Motifs as Proinflammatory Factors Render Autochthonous Tumors Permissive for Infiltration and Destruction J Immunol 2004 172:5861-5869.

33. Barnas, J. L., Simpson-Abelson, M. R., Yokota, S. J., Kelleher, R. J. & Bankert, R. B. T cells and stromal fibroblasts in human tumor microenvironments represent potential therapeutic targets. *Cancer Microenviron* 3, 29-47 (2010).
34. Bellone, M. C. A. Ways to Enhance Lymphocyte Trafficking into Tumors and Fitness of
    Tumor Infiltrating Lymphocytes. *Front Oncol* 3, 231 (2013).
35. Curiel, T. J. Tregs and rethinking cancer immunotherapy. *J Clin Invest* 117, 1167-1174 (2007).
36. Tangying Lu, Rupal Ramakrishnan, Soner Altiok, Je-In Youn, Pingyan Cheng, Esteban Celis, Vladimir Pisarev, Simon Sherman, Michael B. Sporn, and Dmitry Gabrilovich. Tumor-infiltrating myeloid cells induce tumor cell resistance to cytotoxic T cells in mice. J Clin Invest. 2011; 121(10):4015-4029.
37. Dung T. Le and Elizabeth M. Jaffee. Regulatory T-cell Modulation Using Cyclophosphamide in Vaccine Approaches: A Current Perspective. Cancer Res Jul. 15, 2012 (72) (14) 3439-3444;
38. Poehlein et al. Current Molecular Medicine, Volume 9, Number 6, August 2009, pp. 673-682(10).
39. Jennifer S. Ko, Arnold H. Zea, Brian I. Rini, Joanna L. Ireland, Paul Elson, Peter Cohen, Ali Golshayan, Patricia A. Rayman, Laura Wood, Jorge Garcia, Robert Dreicer, Ronald Bukowski and James H. Finke. Sunitinib Mediates Reversal of Myeloid-Derived Suppressor Cell Accumulation in Renal Cell Carcinoma Patients. Clin Cancer Res Mar. 15, 2009 (15) (6) 2148-2157
40. Mock, Ulrike, et al. "Automated manufacturing of chimeric antigen receptor T cells for adoptive immunotherapy using CliniMACS prodigy." Cytotherapy 18.8 (2016): 1002-1011.
41. Jin, Chuan, et al. "Safe engineering of CAR T cells for adoptive cell therapy of cancer using long-term episomal gene transfer." EMBO molecular medicine (2016): e201505869.
42. An, Na, et al. "Construction of a new anti-CD19 chimeric antigen receptor and the anti-leukemia function study of the transduced T cells." Oncotarget 7.9 (2016): 10638-10649.
43. Ren, Xuequn, et al. "Modification of cytokine-induced killer cells with chimeric antigen receptors (CARs) enhances antitumor immunity to epidermal growth factor receptor (EGFR)-positive malignancies." Cancer Immunology, Immunotherapy 64.12 (2015): 1517-1529.
44. Oldham, Robyn A A, Elliot M. Berinstein, and Jeffrey A. Medin. "Lentiviral vectors in cancer immunotherapy." Immunotherapy 7.3 (2015): 271-284.
45. Urbanska, Katarzyna, et al. "Targeted cancer immunotherapy via combination of designer bispecific antibody and novel gene-engineered T cells." Journal of translational medicine 12.1 (2014): 1.
46. Remington, Joseph Price. Remington: The science and practice of pharmacy. Eds. David B. Troy, and Paul Beringer. Vol. 1. Lippincott Williams & Wilkins, 2006.

SEQUENCE LISTING STATEMENT

The application includes the sequence listing that is concurrently filed in computer readable form. This sequence listing is incorporated by reference herein.

The invention claimed is:

1. A purified population of autologous dual-specific lymphocytes which have specificity for two or more antigens, wherein a population of lymphocytes is isolated from a patient and each lymphocyte expresses an endogenous receptor for a tumor associated antigen (TAA) and is genetically engineered to express an additional receptor for a strong antigen, wherein the population of dual-specific lymphocytes target a plurality of TAAs and the strong antigen.

2. The purified populations of claim 1, wherein the strong antigen is a pathogen, a pathogenic antigen, or an alloantigen.

3. The purified population of claim 2, wherein the strong antigen is an antigen from a pathogen, wherein the pathogen is selected from the group consisting of listeria monocytogenes, Bacillus Calmette-Guérin, tetanus, diphtheria, adenovirus, herpes simplex virus, vaccinia virus, myxoma virus, poliovirus, vesicular stomatitis virus, measles virus, influenza virus, and Newcastle disease virus.

4. The composition comprising the purified population of dual-specific lymphocytes of claim 1 and a pharmaceutically acceptable carrier.

5. A method of treating a patient with a tumor comprising:
   (a) administering to the patient an effective amount of the autologous dual-specific lymphocytes of claim 1, and
   (b) injecting the patient with a strong antigen.

6. The method of claim 5, wherein the autologous dual-specific lymphocytes are injected into the patient intravenously and the strong antigen is injected intratumorally.

7. The method of claim 5, wherein the strong antigen is selected from the group consisting of a viral antigen, a bacterial antigen, and an alloantigen.

8. The method of claim 7, wherein the strong antigen is an antigen from a pathogen, wherein the pathogen is selected from the group consisting of group of listeria monocytogenes, Bacillus Calmette-Guérin, tetanus, diphtheria, adenovirus, herpes simplex virus, vaccinia virus, myxoma virus, poliovirus, vesicular stomatitis virus, measles virus, influenza virus, and Newcastle disease virus.

9. A method of producing an autologous population of dual-specific lymphocytes that can target a plurality of tumor associated antigens and at least one strong antigen, the method comprising the steps of:
   (a) isolating lymphocytes from a patient;
   (b) purifying the tumor-specific lymphocytes from the isolated lymphocytes; and
   (c) genetically engineering the purified lymphocytes to express a second receptor specific to a strong antigen, wherein the resulting population comprises dual-specific lymphocytes.

10. The method of claim 9, wherein step (c) further comprises expanding the isolated tumor-specific lymphocytes in culture.

11. The method of claim 9, wherein step (a) comprises isolating the lymphocytes from a tumor, peripheral blood or bone marrow of the patient.

12. The method of claim 9, wherein the strong antigen is selected from the group consisting of a viral antigen, a bacterial antigen, and an alloantigen.

13. The method of claim 12, wherein the strong antigen is an antigen from a pathogen, wherein the pathogen is selected from the group consisting of group of listeria monocytogenes, Bacillus Calmette-Guérin, tetanus, diphtheria, adenovirus, herpes simplex virus, vaccinia virus, myxoma virus, poliovirus, vesicular stomatitis virus, measles virus, influenza virus, and Newcastle disease virus.

14. The method of claim 9, wherein the genetically engineered receptor is a chimeric receptor.

15. The method of claim 9, wherein the lymphocytes are selected from the group consisting of CD4+T cells, CD8+T cells, and natural killer (NK) cells.

16. The method of claim 9, wherein the lymphocytes are stimulated in culture in the presence of an interleukin to stimulate growth.

17. The method of claim 16, wherein the interleukin is selected from the group consisting of IL-2, IL-7 and IL-15.

18. The method of claim 9, wherein the lymphocytes are stimulated with the strong antigen or TAA in culture to proliferate.

19. The method of claim 9, wherein the genetic engineering comprises transducing the lymphocyte with a gene encoding the receptor to the strong antigen.

* * * * *

UNITED STATES PATENT AND TRADEMARK OFFICE
CERTIFICATE OF CORRECTION

| | |
|---|---|
| PATENT NO. | : 11,965,177 B2 |
| APPLICATION NO. | : 17/160952 |
| DATED | : April 23, 2024 |
| INVENTOR(S) | : Weiguo Cui |

It is certified that error appears in the above-identified patent and that said Letters Patent is hereby corrected as shown below:

In the Specification

Column 6, Line 15, "CD1 1b$_+$" should be --CDE11b$_+$--.

Column 9, Line 31, "CART" should be --CAR T--.

Signed and Sealed this
Eighteenth Day of June, 2024

Katherine Kelly Vidal
*Director of the United States Patent and Trademark Office*

```
SEQUENCE LISTING

<160> NUMBER OF SEQ ID NOS: 3

<210> SEQ ID NO 1
<211> LENGTH: 8
<212> TYPE: PRT
<213> ORGANISM: Homo sapiens

<400> SEQUENCE: 1

Phe Ile Tyr Ala Gly Ser Leu Ser
1               5

<210> SEQ ID NO 2
<211> LENGTH: 9
<212> TYPE: PRT
<213> ORGANISM: Homo sapiens

<400> SEQUENCE: 2

Lys Leu Val Ala Asn Asn Thr Arg Leu
1               5

<210> SEQ ID NO 3
<211> LENGTH: 8
<212> TYPE: PRT
<213> ORGANISM: Homo sapiens

<400> SEQUENCE: 3

Ser Ile Ile Asn Phe Glu Lys Leu
1               5
```